（12） United States Patent
Desai et al.

(10) Patent No.: US 9,758,459 B2
(45) Date of Patent: Sep. 12, 2017

(54) ALLOSTERIC MODULATORS OF FACTOR XIA AS ANTICOAGULANT AGENTS

(71) Applicant: VIRGINIA COMMONWEALTH UNIVERSITY, Richmond, VA (US)

(72) Inventors: Umesh R. Desai, Richmond, VA (US); Rajesh Karuturi, Richmond, VA (US); Akul Mehta, Richmond, VA (US); Rami A. Al-Horani, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 78 days.

(21) Appl. No.: 14/442,100

(22) PCT Filed: Nov. 12, 2013

(86) PCT No.: PCT/US2013/069614
§ 371 (c)(1),
(2) Date: May 12, 2015

(87) PCT Pub. No.: WO2014/075045
PCT Pub. Date: May 15, 2014

(65) Prior Publication Data
US 2016/0311842 A1    Oct. 27, 2016

Related U.S. Application Data

(60) Provisional application No. 61/725,266, filed on Nov. 12, 2012, provisional application No. 61/752,107, filed on Jan. 14, 2013, provisional application No. 61/761,000, filed on Feb. 5, 2013.

(51) Int. Cl.
| | |
|---|---|
| *C07C 35/16* | (2006.01) |
| *C07H 13/08* | (2006.01) |
| *C07C 69/757* | (2006.01) |
| *C07C 309/58* | (2006.01) |
| *C07D 239/91* | (2006.01) |
| *C07D 403/12* | (2006.01) |
| *C07D 403/14* | (2006.01) |
| *C07D 405/14* | (2006.01) |

(52) U.S. Cl.
CPC ............ *C07C 35/16* (2013.01); *C07C 69/757* (2013.01); *C07C 309/58* (2013.01); *C07D 239/91* (2013.01); *C07D 403/12* (2013.01); *C07D 403/14* (2013.01); *C07D 405/14* (2013.01); *C07H 13/08* (2013.01); *C07C 2601/14* (2017.05)

(58) Field of Classification Search
None
See application file for complete search history.

(56) References Cited

U.S. PATENT DOCUMENTS

| | | |
|---|---|---|
| 5,159,069 A | 10/1992 | Hirayama et al. |
| 2006/0154915 A1 | 7/2006 | Corte et al. |
| 2012/0213701 A1 | 8/2012 | Kassis et al. |

OTHER PUBLICATIONS

Praveen, T., Das, T., Sureshan, K. M., Shashidhar, M. S., Samanta, U., Pal, D., & Chakrabarti, P. (2002). Silver (I) oxide-silver halide mediated alcoholysis of O-benzoyl-myo-inositol 1, 3, 5-orthoformates: intramolecular assistance by the sulfonyl group. Journal of the Chemical Society, Perkin Transactions 2, (2), 358-365.*
Al-Horani, R. A., Liang, A., & Desai, U. R. (2011). Designing nonsaccharide, allosteric activators of antithrombin for accelerated inhibition of factor Xa. Journal of medicinal chemistry, 54(17), 6125-6138.*
Henry et al., "Sulfated, low molecular weight lignins inhibit a select group of heparin-binding serine proteases", Biochemical and Biophysical Research Communications, Jan. 2, 2012, pp. 283-286, vol. 417, No. 1.
Keddie et al., "Development of inositol-based antagonists for the D-myo-inositol 1,4,5-trisphosphate receptor", Chemical Communications, Jan. 7, 2011, pp. 242-244, vol. 47, No. 1.

* cited by examiner

*Primary Examiner* — Shaojia Anna Jiang
*Assistant Examiner* — Dale R Miller
(74) *Attorney, Agent, or Firm* — Whitham, Curtis & Cook, P.C.

(57) ABSTRACT

Compounds which allosterically modulate and/or inhibit factor XIa activity are provided, as are methods of their use. These compounds include i) sulfated gallolyl glucosides, ii) sulfated quinazolinones, and iii) sulfated inositol analogs. The compounds used as anticoagulant agents.

4 Claims, 13 Drawing Sheets

Scheme 2. Synthesis of sulfated QAOs 7S – 20S. *a)* CuSO$_4$·5H$_2$O (1 mol%), Sodium ascorbate (5 mol%), DMF/H$_2$O (1:1), rt/overnight, 80-95%, *b)* SO$_3$·Me$_3$N, TEA, CH$_3$CN, microwave/30 min, 85-90%.

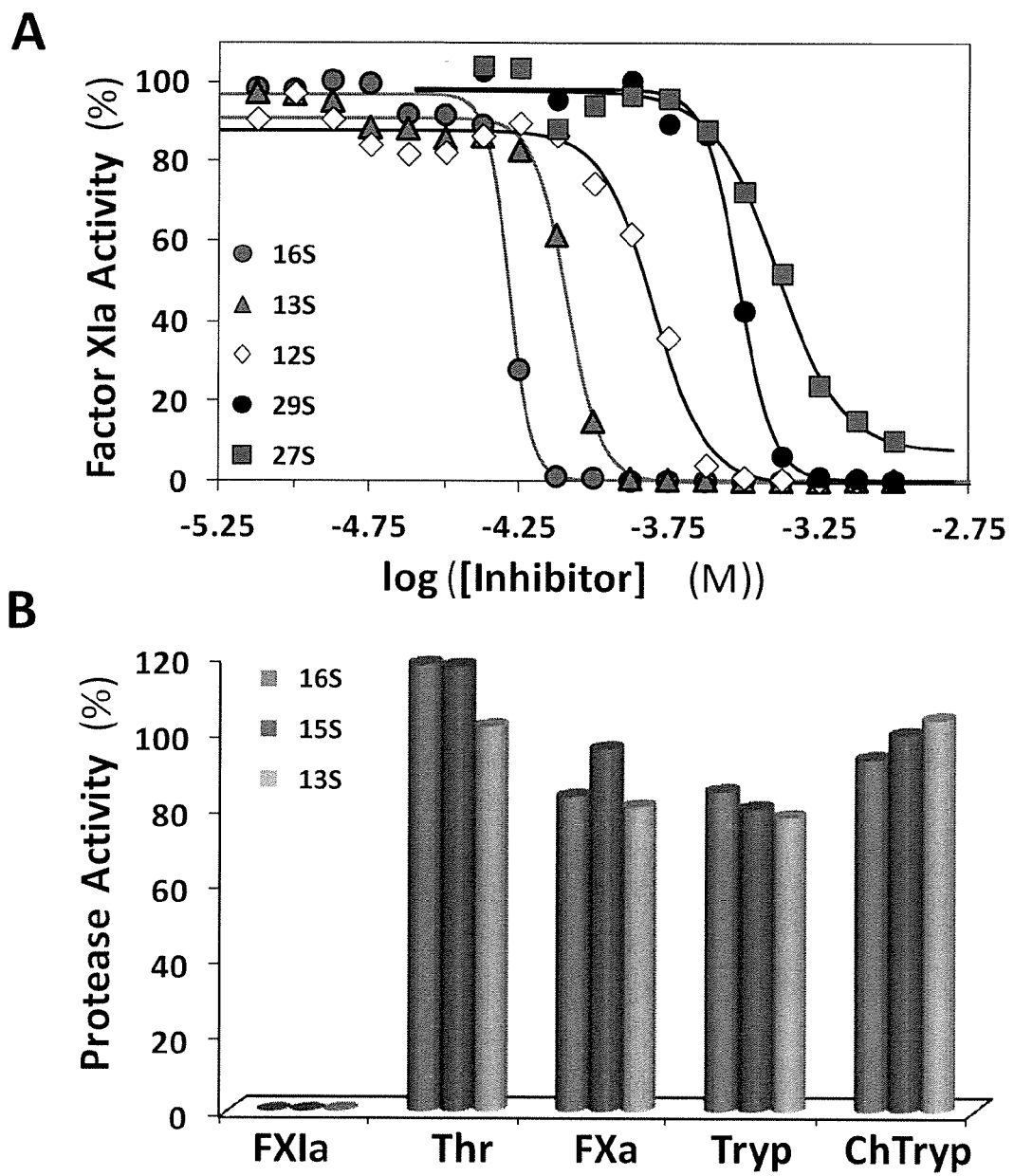
Figure 12 A and B

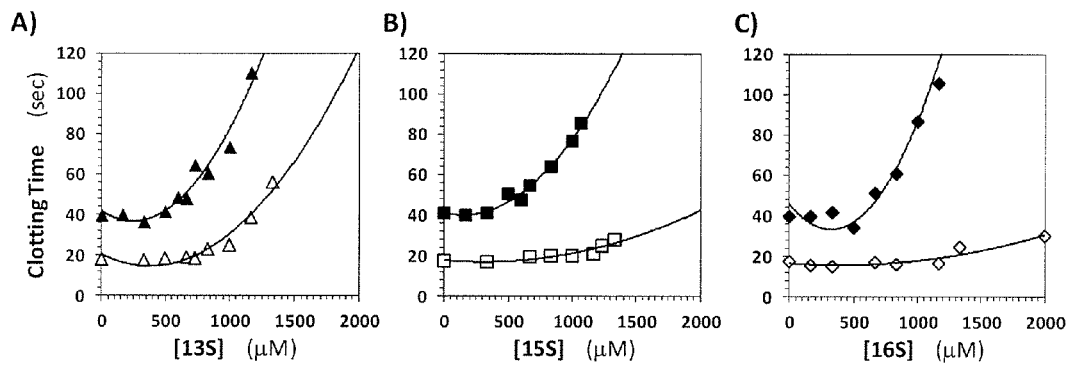
Figure 13 A-C
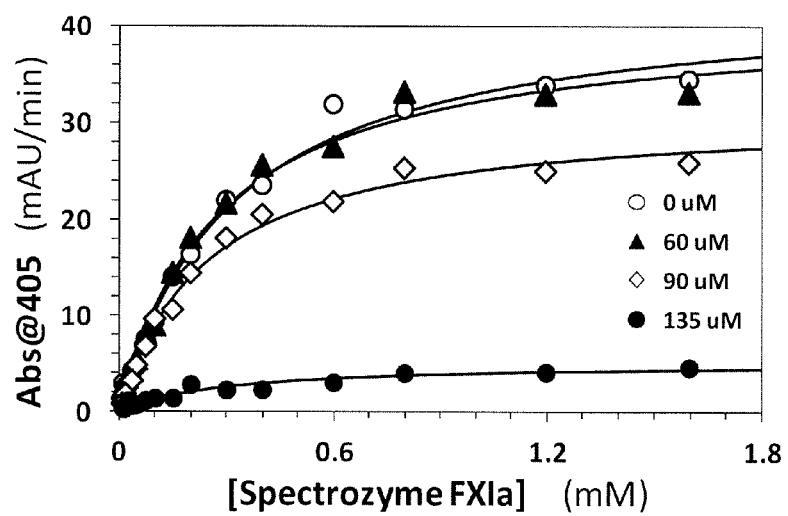
Figure 14

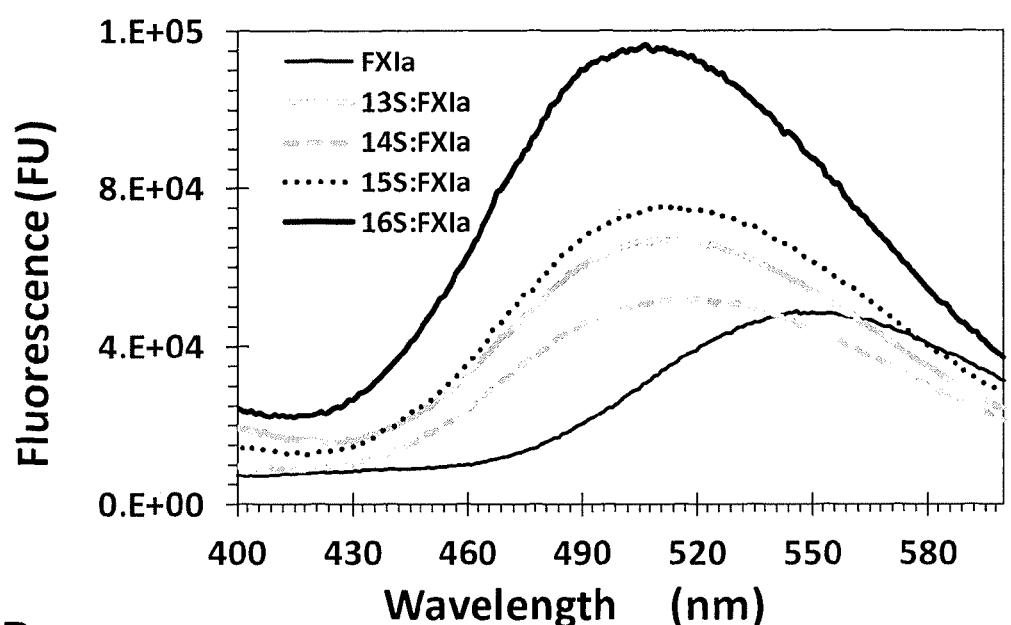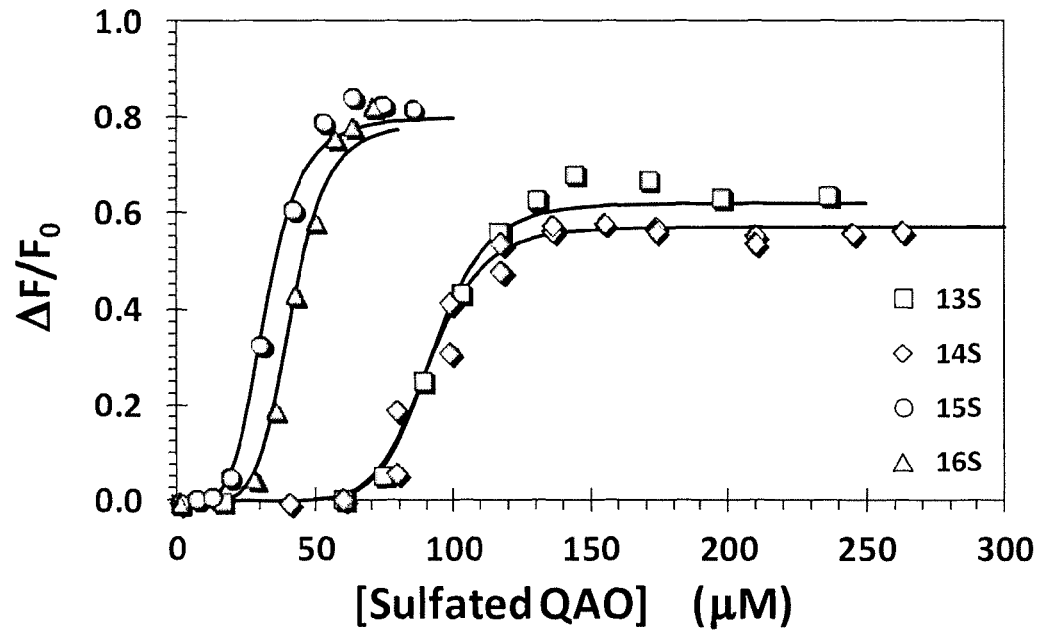
Figure 17A and B

ALLOSTERIC MODULATORS OF FACTOR XIa AS ANTICOAGULANT AGENTS

FIELD OF THE INVENTION

The invention generally relates to allosteric modulators of Factor XIa and their use as anticoagulant agents. In particular, the invention provides i) sulfated gallolyl glucosides, ii) sulfated quinazolinones, and iii) sulfated inositol analogs as inhibitors of Factor XIa.

BACKGROUND OF THE INVENTION

Blood clotting prevents excessive blood loss from tissue damage. Under normal physiological conditions, a balance is maintained between blood flow and blood clot, dysfunction of which may yield either hemorrhage or thrombosis. The coagulation cascade controls the blood status and comprises two main pathways: the intrinsic pathway (triggered by damage to blood vessel walls and the subsequent interactions with nonphysiological surfaces such as collagen, lipoproteins, or bacteria) and the extrinsic pathway (initiated by endothelial damage or hypoxia). The two pathways converge at factor Xa, which cleaves prothrombin to thrombin, which further cleaves fibrinogen to form fibrin monomers. Factor XIIIa polymerizes fibrin monomers leading to the formation of the three-dimensional network of fibrin chains in the clot. Thromboembolic diseases (e.g. deep vein thrombosis, pulmonary embolism, stroke, and myocardial infarction) are all triggered by formation of a pathological clot and are the most frequent causes of death worldwide.

Anticoagulants are prescribed to treat and prevent thromboembolic diseases, e.g. by inhibition of one or more coagulation proteins. Among all proteins in the coagulation cascade, the common pathway enzymes, thrombin and factor Xa, have been successfully targeted with inhibitors. However, a number of drawbacks related to use of the inhibitors are known. For example, the thrombocytopenia and the patient-to-patient response variation of indirect factor Xa and thrombin saccharide-based inhibitors (heparins), the narrow therapeutic window and the genetic polymorphism of warfarin, and the life-threatening high risk of bleeding of particularly indirect and direct thrombin inhibitors (heparins, bivaluridin, argatroban, dabigatran) are major concerns. The safety profile of newer oral peptidomimetic anticoagulants including dabigatran and rivaroxaban is yet to be fully established, especially in cancer patients and pregnant women. Lastly, intracranial hemorrhage is fast becoming a severe complication of oral anticoagulant therapy with a mortality rate of 67% as in the case of warfarin.

There is a need in the art to develop new efficacious yet safe anticoagulants.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

"Downstream" proteases in the coagulation cascade are more involved in the process of coagulation propagation than are "upstream" proteases, which instead initiate or amplify the clotting process. For example, it is known that inhibition of the upstream protease Factor XIa affects only coagulation amplification in a site sprcific manner, while leaving the hemostatic process intact. Accordingly, aspects of the invention provide anticoagulant agents that act by inhibiting the site-specific action of Factor XIa, thereby inhibiting the growth of blood clots while posing a minimal risk of anticoagulation side effects such as excessive bleeding, as well as methods of using the inhibitors as anticoagulant agents.

BRIEF DESCRIPTION OF THE DRAWINGS

FIGS. 12 A and B. A) Representative profiles of direct inhibition of human factor XIa (FXIa) by sulfated quinazolin-4(3H)-ones (QAO). The inhibition of FXIa was measured spectrophotometrically through a S2366 hydrolysis assay at pH 7.4 and 37° C. Solid lines represent sigmoidal fits to the data to obtain $IC_{50}$, $Y_M$, and $Y_O$ using equation 1, as described in the experimental section. B) Proteolytic activity of human thrombin (Thr), factor Xa (FXa), trypsin (Tryp) and chymotrypsin (ChTryp) by 500 µM sulfated QAO (16S, 15S, and 13S) using chromogenic substrate assay. The assays were performed using substrates appropriate for the enzyme being studied under conditions closest to the physiological condition. The ratio of the proteolytic activity of an enzyme in the presence of the sulfated QAO to that in its absence was used to determine percent activity (%).

FIG. 13A-C. Human plasma anticoagulation by sulfated QAOs 13S (shown in A), 15S (B) and 16S (C). The time to clot was measured in either activated partial thromboplastin time assay (solid symbols) or prothrombin time assay (open symbols) in the presence of varying concentrations of the three sulfated QAOs. Solid lines are trend lines, which were used to calculate the concentration of the anticoagulant that is expected to double the clotting time. Mean of two experiments are reported.

FIG. 14. Michaelis-Menten kinetics of S2366 hydrolysis by human factor XIa in the presence of sulfated QAO 14S. The initial rate of hydrolysis at various substrate concentrations was measured spectrophotometrically in pH 7.4 buffer at 37° C. Solid lines represent non-linear regressional fits to the data by the standard Michaelis-Menten equation to yield $K_M$ and $V_{MAX}$.

FIGS. 17A and B. A) Changes in the fluorescence emission spectrum of dansylated factor XIa (FXIa-DEGR) induced by the binding of sulfated QAOs. Spectra were recorded in 50 mM Tris-HCl buffer of pH 7.4 containing 150 mM NaCl and 0.1% PEG8000 at 37° C. B) Fractional change in fluorescence of FXIa-DEGR at 505 nm ($\lambda_{EX}$=345 nm) as a function of the concentration of sulfated QAOs (13S, 14S, 15S, and 16S). Solid line represents non-linear regressional fit to the data using the standard Hill equation 3 to obtain the $\Delta F_{MAX}$, Hill coefficient 'n', and $K_D$ of binding.

DETAILED DESCRIPTION

Figure 1:
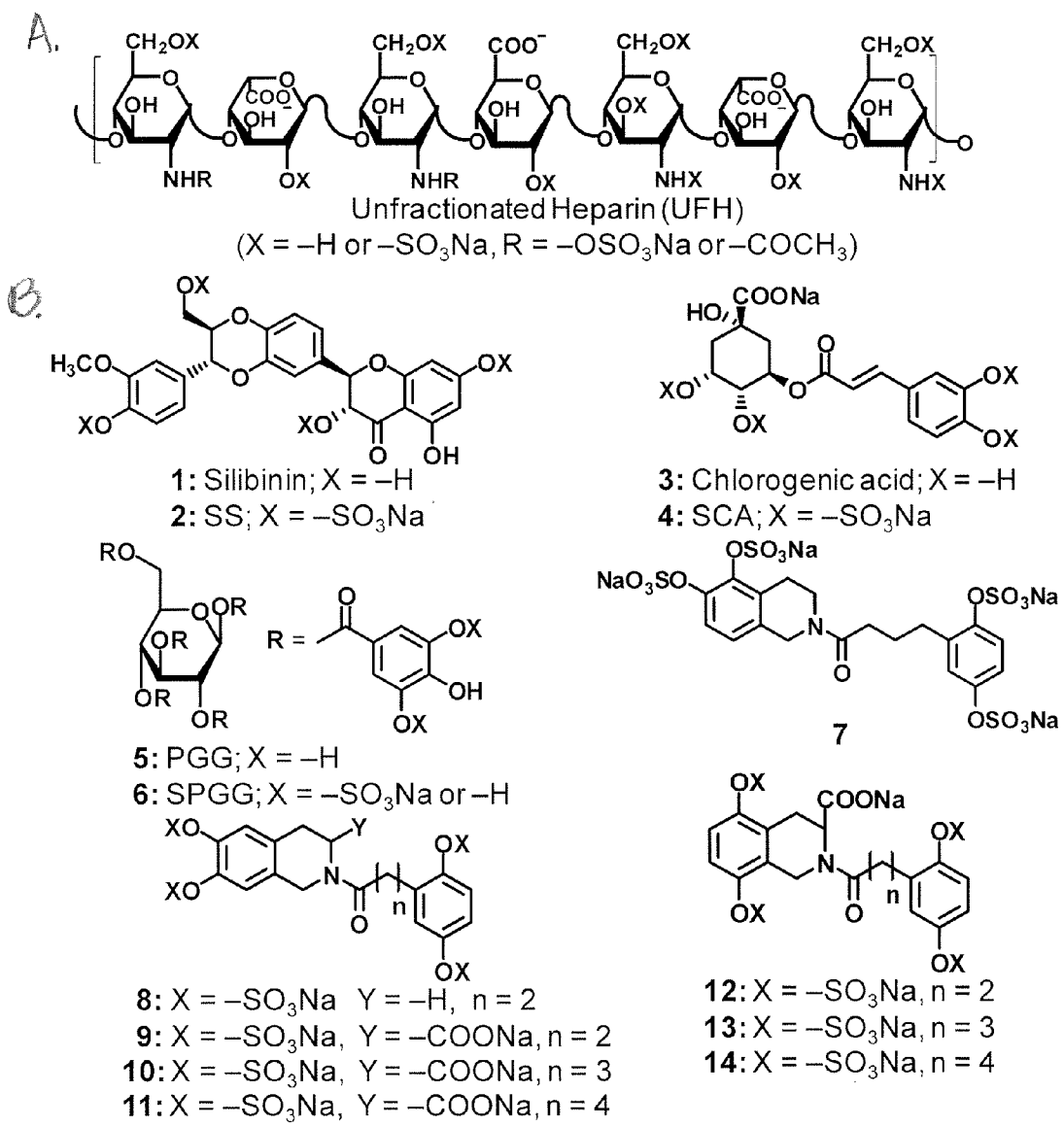
FIGS. 1A and B. Structures of heparins (A) and the polyphenolic as well as the sulfated molecules were screened against factor XIa (B). Shown in A are heparins including unfractionated heparin (UFH) (Mwt ~15,000 Da) which is highly heterogeneous and polydisperse mixtures of linear polysulfated polysaccharides. Shown in B are the chemical structures of the diversified library of small molecules which were screened against factor XIa including silibinin (1), sulfated silibinin (SS) (2), chlorogenic acid (3), sulfated chlorogenic acid (SCA) (4), pentagalloyl glucopyranoside (5), sulfated pentagalloylglucoside (SPGG) (6), and tetrahydroisoquinoline-based scaffolds (7-14).

In a first aspect of the invention, gallolyl glucosides, which are allosteric factor XIa inhibitors are provided. The gallolyl glucosides have a generic hexopyranose-based structure as depicted in Formula I:

Formula I wherein each X is independently selected from H, hydroxyl (—OH), methoxy (—OCH₃), sulfonate (—OSO₃), phosphonate (—OPO₃⁻²), carboxylate (—COO⁻) and —OR, and in a given molecule, the X groups may be the same or different. The "R" group of OR is either or where each Y and Z is independently selected from: —H, —OH, —OCH₃, —OSO₃⁻, —OPO₃⁻² and —COO⁻ (and may be the same or different). Herein, the point of attachment of an equivalent of a variable group (e.g. an equivalent of X, Y, R, etc.), is shown as a straight line beginning at one atom of the group, and ending without contacting another atom. For example, for the equivalent

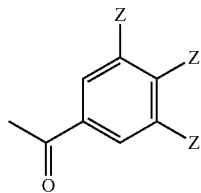

the point of attachment to the base or generic structure of Formula I is via the bond represented by the straight line that begins at the carbonyl carbon and extends to the left, without intersecting another atom. This line is indicated by an arrow in the depiction below:

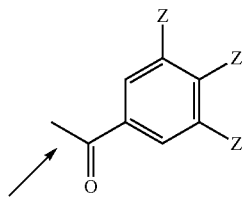

In addition, for Formula I, at least one X must be OR. Stereoisomers and pharmaceutically acceptable salts of Formula I (discussed in detail below) are also encompassed. In some aspects of the invention, the compound of Formula I has a formula as depicted in Formulas II, III, IV, V and VI:

Formula II

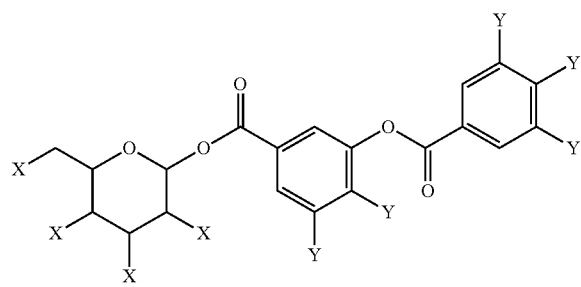

Formula III

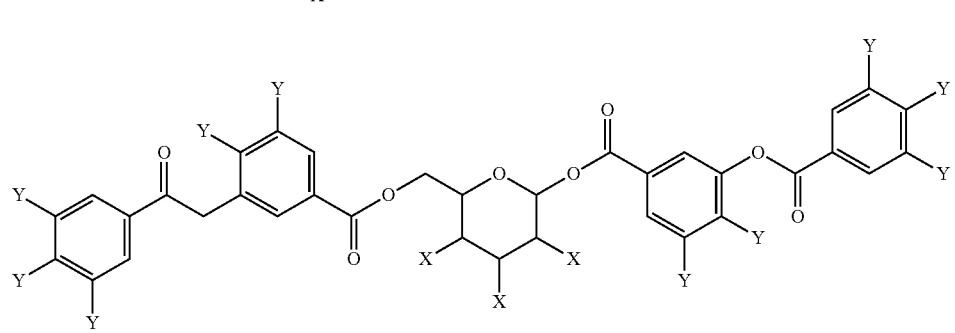

Formula IV

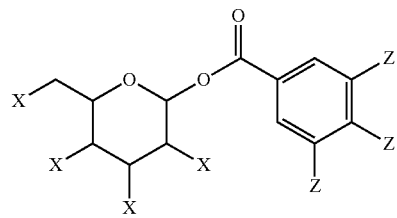

Formula V

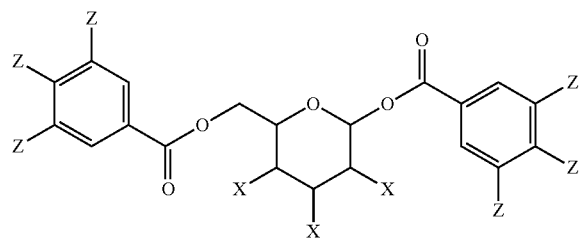

-continued

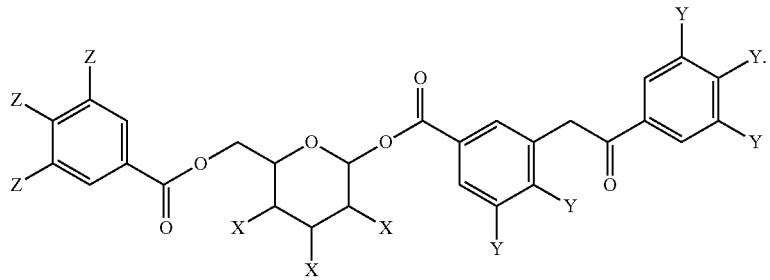

Formula VI

In some aspects, the steroisomeric form of Formula I is, for example, a hexopyranose such as glucose, galactose or mannose, depicted in order below:

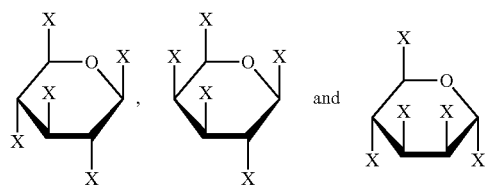

Additional exemplary gallolyl glucoside compounds are described, for example, in Example 1 below, and depicted in the schemes and Figures associated with Example 1.

In a second aspect of the invention, sulfated quinazolinone monomeric and dimeric compounds which are allosteric factor XIa inhibitors are provided. These compounds are represented by generic Formula VII:

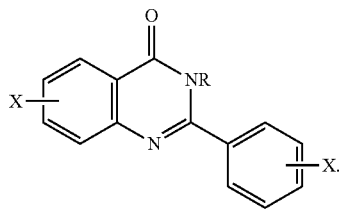

Formula VII

In Formula VII, i) each X is independently selected from —OH⁻, —OCH$_3$, —OSO$_3^-$ or —OPO$_3^{-2}$ (and may be the same or different) and ii) R═—H (for monomeric compounds) or -LY (for dimeric compounds). In the dimeric compounds, the Y of LY is, for example, one of

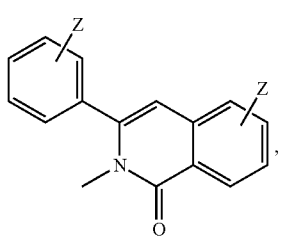

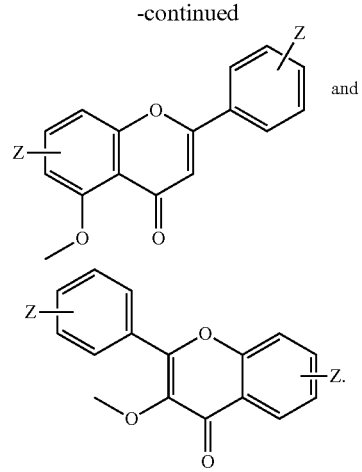

In Y substituents, each Z is independently selected from —OH, —OCH$_3$, —OSO$_3$ and —OPO$_3^{-2}$. The Z groups may be the same or different. The "L" of -LY is a linking group (linking molecule, "linker", etc.), examples of which include but are not limited to:

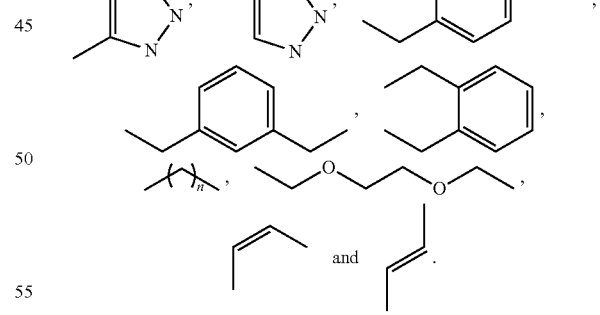

For linking group

n=1-10. For these compounds, at least one of X or Z must be —OSO$_3^-$. As with all the compounds disclosed herein, stereoisomers of the compounds and pharmaceutically acceptable salts of the compounds of Formula VII are also encompassed. Exemplary quinazolinone monomeric and dimeric compounds are described, for example, in Example 2 below, and in Figures and schemes associated with Example 2.

In a third aspect of the invention, small heparin mimetic sulfated inositol-based molecules which are allosteric factor XIa inhibitors are provided. These compounds have generic Formula XI

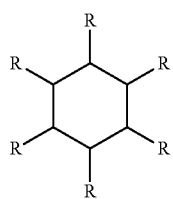

Formula XI wherein each R is independently selected from
i)

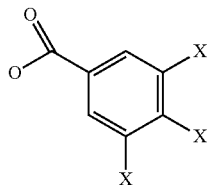

where each X is independently selected from —H, —OH, —OCH$_3$, —OSO$_3^-$, —OPO$_3^{-2}$, and —COO$^-$ (the X groups may be the same or different) and ii) Y, where each Y is independently selected from, —OH, —OSO$_3^-$, —OPO$_3^{-2}$ and —COO$^-$ (the Y groups may also be the same or different from each other, and from the X groups). For each of the inositol-based molecules, at least one R is

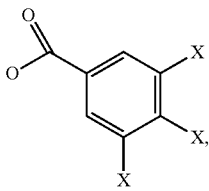

and at least one X is —OSO$_3^-$. Stereoisomers and pharmaceutically acceptable salts of the Formula XI compounds are also encompassed, and these compounds may include mono-, di-, tri-, tetra-, penta- and hexa-benzoyl inositols, as described further in Example 3.

The compounds of the invention are potent, sulfated allosteric small molecules that directly inhibit FXIa via novel allosteric mechanisms, providing high specificity for their functions. Unlike heparin, these inhibitors generally have aromatic architecture. Hydrophobic interactions are likely to be introduced by the aromatic rings, enhancing the selectivity and potency of inhibition. In addition, the inhibitors advantageously have fewer sulfate groups than heparins, thereby avoiding off-target interactions of heparins, and impeding the ability of the novel compounds to cross the blood brain barrier and placenta. Thus, intracranial bleeding is lessened or avoided as is fetal toxicity in pregnant patients, resulting in an improved safety profile.

Accordingly, the present invention provides compositions for use in treating or prophylactically preventing diseases or conditions caused by unwanted or excessive Factor XIa activity in a subject (patient) in need thereof. The compositions include one or more purified or substantially purified compounds as described herein, and a pharmacologically suitable carrier. The compositions may contain a single type of compound or mixtures of compounds, as well as various charged forms and/or sterioisomeric forms and/or pharmaceutically acceptable salts of the compounds. The preparation of such compositions is known to those of skill in the art. For example, see Remington's Pharmaceutical Sciences, Philadelphia, Pa., 19th ed. (1995).

Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of compound in the formulations may vary. However, in general, the amount is from about 1 to about 99%.

The compounds are generally administered in a pharmaceutically acceptable (physiologically compatible) carrier. Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The compound(s) may be formulated in so-called "slow release" formulations which are known in the art.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like. In some embodiments, the sulfonate, phosphonate and/or carboxylate groups on the compound are ion-paired with monovalent (e.g. $Na^+$, $K^+$, etc.), divalent (e.g. $Ca^{+2}$, $Mg^{+2}$, etc.) or postively charged nitrogen containing groups (e.g. ammonium, tetramethylammonium, tetraethylammonium, tetrabutylammonium, etc.).

"Stereoisomers" refers to isomeric molecules that have the same molecular formula and sequence of bonded atoms (constitution), but that differ in the three-dimensional orientations of their atoms in space. The steroisomers may be e.g. enantiomers, diastereomers, etc.

The compositions (preparations) of the present invention may be administered in vivo by any of the many suitable means and/or routes of administration which are known in the art, including but not limited to: by injection (e.g. intravenous, intraperitoneal, intramuscular, subcutaneous, intra-aural, intraarticular, intraartierial, by infusion, and the like), by absorption through epithelial or mucocutaneous linings (e.g., nasal, oral, vaginal, rectal, gastrointestinal mucosa, and the like), by inhalation, orally, as eye drops, via sprays, etc. Administration may be systemic or targeted to one or more particular areas, e.g. to a particular area or tissue such as the heart or lung. In certain embodiments, the mode of administration is aerosolized delivery to the lung through the mouth or nose, application of a patch on the skin, etc.

In addition, the compositions may be administered in conjunction with other treatment modalities such as substances that boost the immune system, various chemotherapeutic agents, antibiotic agents, blood pressure medications, other anticogulants, non-medicinal treatments such as bed rest, etc. Administration may be simultaneous (e.g. in a single composition, or at the same time) or may be at suitable spaced apart time intervals.

The amount of a compound that is administered is a therapeutically effective amount, e.g. an amount sufficient to attenuate, prevent or treat unwanted Factor XIa activity, e.g. to treat a thrombo-embolic or inflammatory disease mediated by coagulation activation via factor XI. The amount that is administered to a subject (patient) in need thereof is generally in the range of from about 0.001 g to about 4 g, and is usually in the range of from about 100 mg to about 1000 mg for the different classes of allosteric factor XIa inhibitors.

The invention generally relates to methods of preventing or treating a disease, disorder and/or condition that is mediated by Factor XIa activation and/or wherein inhibition of Factor XIa has a beneficial effect. The methods preferably comprise a step of administering to a subject at least one compound as disclosed herein, in an amount effective to treat or prevent the disease, disorder and/or condition. The present the compounds generally inhibit factor XI-dependent amplification of coagulation, or factor XI-dependent coagulation or the contribution of Factor XIa to coagulation by inhibiting the activation and or activity of factor XI. Thus, in one aspect, a disease, disorder and/or condition that is mediated by Factor XIa activation and/or wherein inhibition of Factor XIa has a beneficial effect is a disease, disorder and/or condition in which coagulation is involved, such as e.g., a thrombo-embolic or inflammatory disease mediated by coagulation activation via factor XI. Thus, in this embodiment the compounds of the invention may be used in a treatment for reducing or preventing thrombus formation and/or its complications (e.g. unwanted blood coagulation, or the initiation of unwanted blood coagulation), and for the prevention or treatment of disorders, diseases and conditions in which coagulation is involved. These disorders, diseases and conditions include but are not limited to e.g., (acute) myocardial infarction, ischemic stroke, cardio-embolism due to atrial fibrillation, vascular access thrombosis, deep venous thrombosis, arterial thrombosis, coronary artery thrombosis, atherosclerosis, arthritis, vasculitis, respiratory distress syndrome, pulmonary embolism, thrombo-embolism resulting from surgery such as prostate surgery, orthopaedic surgery, such as e.g., hip and knee-replacement, thrombo-embolism resulting from immobilization, thrombosis and occlusion of synthetic grafts, stents, or AV-fistula, diffuse intravascular coagulation (DIC), hemodialysis, atrial fibrillation, sepsis, septic shock, organ failure, kidney failure, toxicity induced by the in vivo administration of therapeutic proteins (e.g., cytokines or mAbs), multiple trauma, ischemia-reperfusion injuries and local undesired fibrin deposition such as e.g., fibrin deposition in the lung alveoli during adult respiratory distress. Any disease or condition assocated with or caused by thrombosis (blood clotting, coagulation, etc.) that is excessive, or unwanted, or misplaced (occurring at an undesirable location), may be prevented or treated, e.g. those caused by tissue damage due to reduced blood flow and hypoxia (oxygen deprivation), accumulation of metabolic products such as lactic acid, and/or complete deprivation of oxygen to the tissue and subsequent infarction (tissue death). Such damage may be caused at the initial location of clot formation, or at a different location if a clot breaks loose and travels through the body (an "embolism"). Such a blockage may affect a part of the body a distance from the actual site of origin, e.g. extensive damage can occur when a blood clot lodges e.g. in the heart, brain or other organ. "Thromboembolism" refers to this phenomenon. There are a number of untoward conditions that can arise, depending on the location of the thrombus and the organs affected, all of which can be prevented or treated by compounds described herein.

The methods involve administering to a subject or patient in need thereof, one or more of the compounds described herein. In some aspects, the diseases and conditions that may be prevented or treated in this manner include but are not limited to: thromboembolic diseases such as deep vein thrombosis, pulmonary embolism, stroke, myocardial infarction, disseminated intravascular coagulation, and thrombotic complications arising from cancer. The subject is generally a mammal, and may be a human, although veterinary applications of the invention are also contemplated.

Those of skill in the art will recognize that in some cases, disease symptoms may be completely eliminated by the use of the compounds. However, much advantage can accrue even if a partial lessening of symptoms is achieved, e.g. if the risk or probability of a stroke, heart attack, etc. is decreased statistically within a population; or if an individual who would have likely suffered a greater trauma or indisposition but for the use of the compounds suffers only a limited indisposition, etc.

The anticoagulant compounds described herein may also be used in e.g. medical equipment, such as test tubes, blood transfusion bags, renal dialysis equipment, various implantable medical devices (e.g. stents, implantable drug delivery devices, etc.), tubing and the like, in order to prevent or decrease the formation of blood clots. The equipment is generally that which comes into contact with blood, either in vivo or ex vivo. Accordingly, the invention also provides items of medical equipment of this type that contains, comprises and/or is at least partially covered or coated with one or more compounds of the invention. The compound(s) may be formulated in slow and/or continuous release formulations, e.g. in a stent or other item that is located within a patient while in use. The invention also provides compositions suitable for addition to such medical equipment or to samples collected in such medical equipment.

As indicated above, the present invention inter alia provides the specified compounds for use in methods of eliciting or increasing anticoagulation, i.e. of decreasing or lessening coagulation. As such, the present invention inter alia provides the specified compounds for use in methods of preventing and treating various thromboembolic diseases without limitation, e.g. deep vein thrombosis, pulmonary embolism, stroke, myocardial infarction, and the like, as listed above. For the avoidance of doubt, in this aspect the present invention may provide the specified compound for use as a medicament in the specified method. Further, the present invention may provide the specified compound as an active therapeutic ingredient in the specified method. Further, the present invention may provide the specified compound for use in a method of treatment of the human or animal body by therapy, the method comprising the specified method.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided herein, it is understood that each intervening value between the lower and upper limit of the range, including tenths of the unit of the values, and any other stated or intervening value in that stated range, is encompassed within the invention, unless the context clearly dictates otherwise. In the case of values that are less than 100, or less than 10, and particularly less that 1, each intervening value, to the hundredth of the unit are included, unless the context clearly dictates otherwise For example, "from about 1 to about 2" includes at a minimum 1, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95 and 2.0. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. In addition, the term "about" when used in reference to a value, refers to values that are larger and smaller than the value, within a range of about one-half the value of the integer. For example, "about 1" refers to at least 0.5, 0.6, 0.7, 0.8, 0.9, 1, 1.1, 1.2, 1.3, 1.4, and 1.5, as well as to smaller divisions as described above (e.g. 0.55, 0.65, 0.75, and so on), an indicated by the context; whereas "about 100" refers to at least 50, 60, 70, 80, 90, 100, 110, 120, 130, 140 and 150, including intervening values, e.g. to the tenth of a unit as described above.

Unless defined otherwise, all technical and scientific terms used herein have the same meaning as commonly understood by one of ordinary skill in the art to which this invention belongs. Any methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Before exemplary embodiments of the present invention are described in greater detail in the Examples below, it is to be understood and will be apparent to those of skill in the art upon reading this disclosure, that each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. It is also to be understood that this invention is not limited to particular embodiments described, as such may, of course, vary. Further, the terminology used herein is for the purpose of describing particular embodiments only, and is not intended to be limiting.

EXAMPLES

Example 1

Sulfated Pentagalloylglucoside is a Potent, Allosteric, and Selective Inhibitor of Factor XIa (FXIa)

Human FXIa is a plasma serine protease that is considerably different from other coagulation proteases. Factor XIa is a dimeric, vitamin K-independent protease that activates factor IX so as to eventually result in a burst of thrombin generation and formation of a blood clot. FXIa is a disulfide-linked homodimer, in which each monomer consists of 607 amino acid residues that form four apple domains A1 through A4 and a trypsin-like catalytic domain. The apple domains of FXI recognize factor IX (FIX), heparin/heparan sulfate, platelet glycoprotein GPIb, and other ligands to facilitate proteolytic function of FXIa and introduce a physiologic response. FXIa activation of FIX results in accelerated thrombin generation, which results in clot formation, while GPIb binding probably contributes to localization of fibrin formation at the site of injury.[1,2]

A heparin-binding site (HBS) is present on the A3 domain of both the zymogen and the protease, and has been shown to contribute to serpin inhibition of FXIa through a template-mediated process.[3,4] Interestingly, FXIa also displays another HBS in its catalytic domain,[5] which binds the sulfated polysaccharide and other polyanions with approximately 100-fold higher affinity than the A3 site.[5,6] The HBS of the catalytic domain contributes less to template-mediated inhibition and more to allosteric or charge neutralization-based inhibition of FXIa by serpins.[7]

We reasoned that targeting the HBS of FXIa using small, designed molecule(s) would yield an effective inhibitor of this important intrinsic pathway enzyme that may be devoid of the major bleeding consequences noted with thrombin and factor Xa inhibitors. Such an inhibitor would function through an allosteric mechanism offering significant advantages in comparison to the traditional active site inhibitors. For example, an allosteric inhibitor is expected to be more selective than an orthosteric inhibitor because the active sites of coagulation enzymes are rather similar (each prefers a P-1 arginine) resulting in difficulties of selectivity. Allosteric sites, on the other hand, are much less conserved and structurally significantly different resulting in higher selectivity.

A key challenge in the design of these inhibitors has been achieving a combination of reasonable selectivity and potency against FXIa. Because coagulation enzymes are trypsin-like proteases, which prefer an arginine or an arginine-like P-1 group, selectivity has to rely on small differences in the binding pocket arising from the many loops surrounding the active site. In this respect, perhaps the only active site relatively easy to target is that of thrombin, which is constrained by the 60-loop.

In light of the observation that no allosteric inhibitors of FXIa have been reported so far and the promise of higher selectivity that an allosteric binding site presents, we screened a focused library of sulfated small molecule scaffolds belonging to the flavonoid, tetrahydroisoquinoline, cinammic acid, and gallic acid series (FIG. 1). The non-saccharide library was developed to mimic sulfated glycosaminoglycan (GAG) structures and contains several scaffolds chosen to yield good structural diversity. Only one molecule from this library, i.e., sulfated pentagalloylglucoside (SPGG) (6), was found to inhibit FXIa in vitro and ex vivo. SPGG can be synthesized in few steps and is an aromatic GAG mimetic with several sulfate groups. Most importantly, SPGG was found to selectively inhibit FXIa from among several coagulation enzymes and utilized the allosteric inhibition mechanism by interacting with the HBS of the catalytic domain of FXIa, as expected on the basis of the GAG-mimicking nature.

Experimental Procedures

Chemicals, Reagents, and Proteins. Anhydrous $CH_2Cl_2$, THF, $CH_3CN$, DMF, methanol, acetone and HPLC grade solvents (acetonitrile and formic acid) were purchased from Sigma-Aldrich (Milwaukee, Wis.) or Fisher (Pittsburgh, Pa.) and used as such. Chemical reactions sensitive to air or moisture were carried out under nitrogen atmosphere in oven-dried glassware. Reagent solutions, unless otherwise noted, were handled under a nitrogen atmosphere using syringe techniques. n-Hexylamine for ion-pairing UPLC was from Acros Organics (Morris Plains, N.J.). Human plasma proteases including thrombin, factor Xa, FXIa, factor IXa, factor VIIa, and recombinant tissue factor were obtained from Haematologic Technologies (Essex Junction, Vt.). Recombinant human FXIa and the isolated FXIa catalytic domain (FXIa-CD), used in the Gailani laboratory, were prepared as described earlier.[7,8] Factor XIIa was purchased from Enzyme Research Laboratories (South Bend, Ind.). Bovine α-chymotrypsin and bovine trypsin were obtained from Sigma-Aldrich (St. Louis, Mo.). Stock solutions of factor XIa, thrombin, factor XIIa, trypsin, and chymotrypsin were prepared in 50 mM TrisHCl buffer, pH 7.4, containing 150 mM NaCl, 0.1% PEG8000, and 0.02% Tween®80. Stock solutions of factor Xa and factor VIIa were prepared in 20 mM TrisHCl buffer, pH 7.4, containing 100 mM NaCl, 2.5 mM CaCl, 0.1% PEG8000, and 0.02% Tween®80. Stock solution of factor IXa was prepared in 20 mM TrisHCl buffer, pH 7.4, containing 100 mM NaCl, 2.5 mM $CaCl_2$, 0.1% PEG8000, 0.02% Tween®80, and 33% v/v ethyleneglycol.

Chromogenic Substrates, Spectrozyme TH (H-D-hexahydrotyrosol-Ala-Arg-p-nitroanilide), Spectrozyme factor Xa (Methoxycarbonyl-D-cyclohexylglycyl-Gly-Arg-p-nitroanilide), Spectrozyme FXIIa (D-ctclohydrotyrosyl-glycyl-L-Arg-p-nitroanilide diacetate salt), Spectrozyme FIXa (D-leucyl-phenylglycyl-Arg-p-nitroanilide diacetate), Spectrozyme factor VIIa (Methanesulphonyl-D-cyclohexylalanyl-butyl-Arg-p-nitroanilide), and Spectrozyme CTY were obtained from American Diagnostica (Greenwich, Conn.). Factor XIa chromogenic substrate (S-2366, H-D-Val-Leu-Arg-p-nitroanilide.2HCl) and trypsin substrate (S-2222, Benzyl-Ile-Glu(γ-OH and —$OCH_3$)-Gly-Arg-p-nitroanilide.HCl) were obtained from Diapharma (West Chester, Ohio). Bovine unfractionated heparin (UFH) was purchased from Sigma-Aldrich (St. Louis, Mo.). Pooled normal human plasma for coagulation assays was purchased from Valley Biomedical (Winchester, Va.). Activated partial thromboplastin time reagent containing ellagic acid (APTT-LS), thromboplastin-D, and 25 mM $CaCl_2$ were obtained from Fisher Diagnostics (Middletown, Va.). Thromboelastograph® Coagulation Analyzer 5000 (TEG®), disposable cups and pins, and 200 mM stock $CaCl_2$ were obtained from Haemoscope Corporation (Niles, Ill.).

Purification of Chemically Synthesized Molecules. Analytical TLC was performed using UNIPLATE™ silica gel GHLF 250 um pre-coated plates (ANALTECH, Newark, Del.). Column chromatography was performed using silica gel (200-400 mesh, 60 Å) from Sigma-Aldrich. Flash chromatography was performed using Teledyne ISCO (Lincoln, Nebr.) Combiflash® RF system and disposable normal silica cartridges of 30-50μ particle size, 230-400 mesh size and 60 Å pore size. The flow rate of the mobile phase was in the range of 18 to 35 mL/min and mobile phase gradients of ethyl acetate/hexanes and $CH_2Cl_2/CH_3OH$ were used to elute unsulfated compounds.

Sulfated molecules were purified using Sephadex® G10 size exclusion chromatography. The quaternary ammonium counter ion of sulfate groups present in the molecules was exchanged for sodium ion using SP Sephadex®-Na cation exchange chromatography. Sephadex® G10 and SP Sephadex®-Na chromatographies were performed using Flex columns (KIMBLE/KONTES, Vineland, N.J.) of dimensions 170×1.5 cm and 75×1.5 cm, respectively. For regeneration of the cation exchange column, 1 L of 2 M NaCl solution was used. Water was used as eluent in both chromatographies. Five mL fractions were collected and analyzed by capillary electrophoresis (CE). CE experiments were performed using a Beckman P/ACE MDQ system (Fullerton, Calif.). Electrophoresis was performed at 25° C. and a constant voltage of 8 kV or a constant current of 75 μA using an uncoated fused silica capillary (ID 75 μm) with the total and effective lengths of 31.2 cm and 21 cm, respectively. A sequential wash of 1M HCl (10 min), water (3 min), 1M NaOH (10 min), and water (3 min) at 20 psi was used to activate the capillary. Before each run, the capillary was rinsed with the run buffer; 50 mM sodium phosphate buffer of pH=3, for 3 min at 20 psi. Sulfated compounds injected at the cathode (0.5 psi for 4 s) and detected at the anode (214 nm). The purity of each sulfated compound, as determined by CE, was greater than 95%. Chemical Synthesis of Diversified Library of Sulfated Molecules. The polyphenolic precursors of the sulfated molecules were either commercially available as silibinin (1), chlorogenic acid (3), and pentagalloyl glucopyranoside (5) or were chemically synthesized as reported earlier for polyphenolic 1,2,3,4-tetrahydroisoquinoline (THIQ) derivatives (7-14) (see FIG. 1).[10,11] Briefly, synthesis of polyphenolic THIQ derivatives was achieved in quantitative yields using Horner-Wadsworth-Emmons and Pictet-Spengler reactions followed by EDCI-mediated amidation and $BBr_3$-assisted deprotection[10]. Sulfated silibinin (SS, 2), and sulfated chlorogenic acid (SCA, 4) were synthesized by the microwave-assisted synthesis developed earlier.[11] Briefly, the polyphenolic precursors (1, 3, and 5) and trimethylamine-sulfur trioxide (5 equivalents/—OH group) were mixed in equivolume mixture of DMF and $CH_3CN$ (3 mL) in microwave tube. The reaction tube was sealed and microwaved (CEM-discover microwave synthesizer) for 0.5-2 h at 100° C. Sulfated THIQ derivatives were synthesized in an equivolume mixture of DMF and CH3CN (3 mL) containing the trimethylamine-sulfur trioxide complex (6 equivalents/—OH group) which was heated for 5 h at 80° C.

Synthesis of Sulfated Pentagalloyl Glucoside (SPGG, 6). Pentagalloyl glucopyranoside (5) (25 mg, 0.027 mmol) was sulfated in DMF:$CH_3CN$ mixture (3 mL) using trimethylamine-sulfur trioxide complex (281 mg, 2.03 mmol). The reaction mixture was microwaved at 100° C. for 2 h. The resulting crude product was cooled and concentrated in vacuum at temperature less than 35° C. It was purified as described above using the size exclusion chromatography (G-10). The sodium salt form of the isolated white fluffy SPGG solid mixture (42 mg, 63%) was generated by the sodium exchange chromatography as described above. The synthesis was repeated three times under similar conditions.

Characterization of Synthetic Compounds. Each compound was characterized using $^1H$ and $^{13}C$ NMR spectroscopy, which was performed on Bruker 400 MHz spectrometer in either $CDCl_3$, $CD_3OD$, acetone-d6, or $D_2O$. Signals, in part per million (ppm), are either relative to the internal standard (tetramethyl silane, TMS) or to the residual peak of the solvent. The NMR data are reported as chemical shift (ppm), multiplicity of signal (s=singlet, d=doublet, t=triplet, q=quartet, dd=doublet of doublet, m=multiplet), coupling constants (Hz), and integration. ESI MS of unsulfated molecules were recorded using Waters Acquity TQD MS spectrometer in positive ion mode whereas ESI MS negative mode was used for sulfated compounds. Samples were dissolved in methanol or water and infused at a rate of 20 μL/min. Mass scans were obtained, as reported earlier, for both unsulfated as well as sulfated compounds.[9,10] The NMR and MS data of polyphenolic and sulfated THIQ molecules were consistent with the reported values. We present here the data for the exemplary newly synthesized molecule 6.

Sulfated Pentagalloylglucoside (SPGG, 6). $^1H$-NMR ($D_2O$, 400 MHz): 8.11-7.40 (m, 10 H), 6.51-6.47 (m, 1 H), 6.11-6.18 (m, 1 H), 5.79-5.97 (m, 2 H), 4.85-4.60 (m, 3 H). 13C-NMR (D2O, 100 MHz): 166.39, 165.70, 165.40, 164.71, 150.62, 150.53, 147.82, 147.43, 147.17, 145.69, 145.53, 126.34, 122.42, 122.22, 122.17, 121.98, 120.97, 119.74, 118.99, 118.69, 115.32, 93.04, 74.5, 72.24, 71.59, 68.90, 63.50.

UPLC-MS Characterization of SPGG. Waters Acquity H-class UPLC system equipped with a photodiode array detector and triple quadrupole mass spectrometer was used for characterization of SPGG. A reversed-phase Waters BEH C18 column of particle size 1.7μ and 2.1×50 mm dimensions at 30+/−2° C. was used for separation of SPGG components. Solvent A consisted of 25 mM n-hexylamine in water containing 0.1% (v/v) formic acid, while solvent B consisted of 25 mM n-hexylamine in acetonitrile-water mixture (3:1 v/v) containing 0.1% (v/v) formic acid. Resolution of SPGG into distinct peaks was achieved with a flow rate of 500 μL/min and a linear gradient of 3% solvent B per min over 20 min (initial solvent B proportion was 20% v/v). The sample was first monitored for absorbance in the range of 190-400 nm and then directly introduced into the mass spectrometer. ESI-MS detection was performed in positive ion mode for which the capillary voltage was 4 kV, cone voltage was 20 V, desolvation temperature was 350° C. and nitrogen gas flow was maintained at 650 L/hr. Mass scans were collected in the range of 1000-2048 amu within 0.25 s and several of these added to enhanced signal-to-noise ratio. Direct Inhibition of Factor XIa. Direct inhibition of FXIa was measured by a chromogenic substrate hydrolysis assay, as reported earlier[12] using a microplate reader (FlexStation III, Molecular Devices) at 37° C. Generally, each well of the 96-well microplate contained 85 μL pH 7.4 buffer to which 5 μL potential FXIa inhibitor (or solvent reference) and 5 μL FXIa (0.765 nM final concentration) were sequentially added. After 10 min incubation, 5 μL factor XIa substrate (345 μM) was rapidly added and the residual FXIa activity was measured from the initial rate of increase in absorbance at 405 nm. Stocks of potential FXIa inhibitors were at least 10 mM or 550 μg/mL (SPGG) concentration and serially diluted to give twelve different aliquots in the wells. Relative residual FXIa activity at each concentration of the inhibitor was calculated from the ratio of FXIa activity in the presence and absence of the inhibitor. Logistic equation 1 was used to fit the dose-dependence of residual protease activity to obtain the potency ($IC_{50}$) and efficacy ($\Delta Y$) of inhibition. In this equation, Y is the ratio of residual factor XIa activity in the presence of inhibitor to that in its absence (fractional residual activity), $Y_M$ and $Y_O$ are the maximum and minimum possible values of the fractional residual proteinase activity, $IC_{50}$ is the concentration of the inhibitor that results in 50% inhibition of enzyme activity, and HS is the Hill slope. Nonlinear curve fitting resulted in $Y_M$, $Y_O$, $IC_{50}$ and HS values.

$$Y = Y_o + \frac{Y_M - Y_o}{1 + 10^{(\log[I]_o - \log IC_{50})(HS)}} \quad \text{Eq. 1}$$

SPGG Inhibition of FXIa Activation of FIX. Plasma FIX (500 nM) was incubated with human FXIa (3 nM) in 50 mM Hepes buffer, pH 7.4, containing 125 mM NaCl, 5 mM $CaCl_2$, and 0.1 mg/mL bovine serum albumin at 24° C. At various incubation times, 7 µL aliquots were removed, mixed with 7 µL of reducing sample buffer (233 mM Tris-HCl, 138 mM SDS, 19% glycerol, 10% 2-mercaptoethanol, 0.01% bromophenol blue, pH 6.8), fractionated on 12% polyacrylamide-SDS gels, and then transferred to nitrocellulose. The primary antibody was goat anti-human FIX polyclonal IgG (Enzyme Research Laboratories, South Bend, Tenn.), and the secondary antibody was horseradish peroxidase-conjugated anti-goat IgG. Detection was by chemiluminescence. The relative positions of FIX and FIXαβ bands were confirmed using Western blots of known standards for each protein.

Inhibition of Proteases of the Coagulation and Digestive Systems by SPGG. The inhibition potential of SPGG against coagulation enzymes including thrombin, factor VIIa, factor IXa, factor Xa, and factor XIIa, and digestive enzymes including trypsin and chymotrypsin was evaluated using chromogenic substrate hydrolysis assays reported in the literature.[12] These assays were performed using substrates and conditions appropriate for the enzyme being studied. For selectivity analysis, at least six serially diluted concentrations of 73.3 mg/mL SPGG were utilized and the fractional residual enzyme activity was measured at each concentration. The inhibition profile was determined over a range of inhibitor concentrations to determine the $IC_{50}$ of the enzyme-inhibitor complex. The $K_M$ of the substrate for its enzyme was used to identify the concentration of the substrate to be used for inhibition studies. The concentrations of enzymes and substrates in microplate cells were: 6 nM and 50 µM for thrombin; 1.09 nM and 125 µM for factor Xa; 5 nM and 125 µM for factor XIIa; 89 nM and 850 µM for factor IXa; 8 nM and 1000 µM for factor VIIa (along with 40 nM recombinant tissue factor); 72.5 ng/mL and 80 µM for bovine trypsin; and 500 ng/mL and 240 µM for bovine chymotrypsin.

Michaelis-Menten Kinetics of Substrate Hydrolysis by Factor XIa in Presence of SPGG. The initial rate of S-2366 hydrolysis by either wild-type FXIa (3 nM) or FXIa catalytic domain (6 nM) was obtained from the linear increase in absorbance at 405 nM corresponding to less than 10% consumption of the chromogenic substrate. The initial rate was measured as a function of various concentrations of the substrate (0-2 mM) in the presence of fixed concentration of SPGG (0-50 µg/mL) in 50 mM Tris-HCl buffer, pH 7.6, containing 150 mM NaCl, 0.1 mg/mL bovine serum albumin and 5 mM $CaCl_2$. Active site concentrations for preparations of FXIa were determined by titrations with human antithrombin in an S-2366 cleavage assay. The reaction was monitored using a SpectraMax 340 microtiter plate reader (Molecular Devices Corp., Sunnyvale, Calif.) with a reaction volume of 100 µL and path length of 3 mm. Each assay was performed in triplicate. The concentration of S-2366 was measured using an absorption coefficient of 8,266 M-1cm-1 at $\lambda_{342}$ nm, while the free p-nitroaniline concentration was calculated using an absorption coefficient of 9,933 M $cm^{-1}$ at $\lambda_{405}$ nm. The data was fitted using the standard Michaelis-Menten equation to determine the $K_M$ and $V_{MAX}$.

Results

Library of Polyphenolic and Sulfated Molecules. At the outset, the fundamental idea in discovering allosteric FXIa inhibitors was to screen GAG mimetics that potentially bind the HBS and induce an inhibitory conformational change in the active site. Considering the size of the HBS on FXIa, we studied silibinin (1) and its sulfated derivative (2), chlorogenic acid (3) and its sulfated derivative (4), pentagalloylglucoside (5) and its sulfated derivative (6), and a library of THIQ derivatives (7-14). These structures contain significantly diverse structures, especially in terms of placement of multiple sulfate groups that could be expected to mimic heparin's interaction with FXIa.

Sulfated silibinin (SS, 2), sulfated chlorogenic acid (SCA, 4), and sulfated pentagalloylglucoside (SPGG, 6) were synthesized by the microwave-assisted sulfation strategy,[11] while sulfated THIQ derivatives were synthesized by sulfation by heating the reaction mixture for 5 hrs at 80° C.[17] In either case, sulfation was high yielding (>60%). Each sulfated molecule was homogeneous, i.e., containing a single sulfated species, as assessed by capillary electrophoresis and detailed $^1H$ NMR, $^{13}C$ NMR and ESI-MS techniques, except for SPGG, which showed partially sulfated species as described below.

Structure Determination of SPGG. The capillary electrophoretic profile of SPGG in reverse polarity mode displayed a complex, ill-resolved pattern indicating the presence of partially sulfated components (not shown). To identify the proportion and structure of these components, we resorted to reversed-phase ion-pairing UPLC, a technique that has found good utility in resolving highly sulfated GAGs and related molecules. In this technique, an ion-pairing agent, such as n-hexylamine, is introduced in the mobile phase so as to replace sodium cations present on each sulfate group and impart considerable hydrophobicity to the molecule. Resolution arises from the different hydrophobicities of the constituents that contain varying number of n-hexylamine groups. The UPLC profile of SPGG showed the presence of six major nearly baseline resolved peaks, labeled p1 through p6 in FIG. 2, each of which was found to further contain multiple peaks.

The ESI-MS profile of each peak, observed between 1000 and 2048 m/z range, was found to contain a doubly charged molecular ion with a general formula of $[(PGG+n\times SO_3-HXA-n\times H)+2\times HXA]^{2+}$, where n is the number of sulfonate ($SO_3$)-hexylammonium (HXA) ion-pairs present in the molecule (not shown). For example, peaks p3, p4 and p5 displayed molecular ions at 1388.43, 1478.99 and 1569.60 m/z, respectively, corresponding to doubly charged SPGG species containing 9, 10 and 11 sulfate groups with 11, 12 and 13 n-hexylamines, respectively, as ion-pairs. A similar behavior was observed for peaks p1, p2 and p6, which corresponded to SPGG species with 7, 8 and 12 sulfate groups, respectively. In addition to the molecular ions, the MS also displayed several other ions corresponding to the loss of one or more hexylamine-paired sulfonate groups further confirming the identity of the parent sulfated species.

Figure 2:
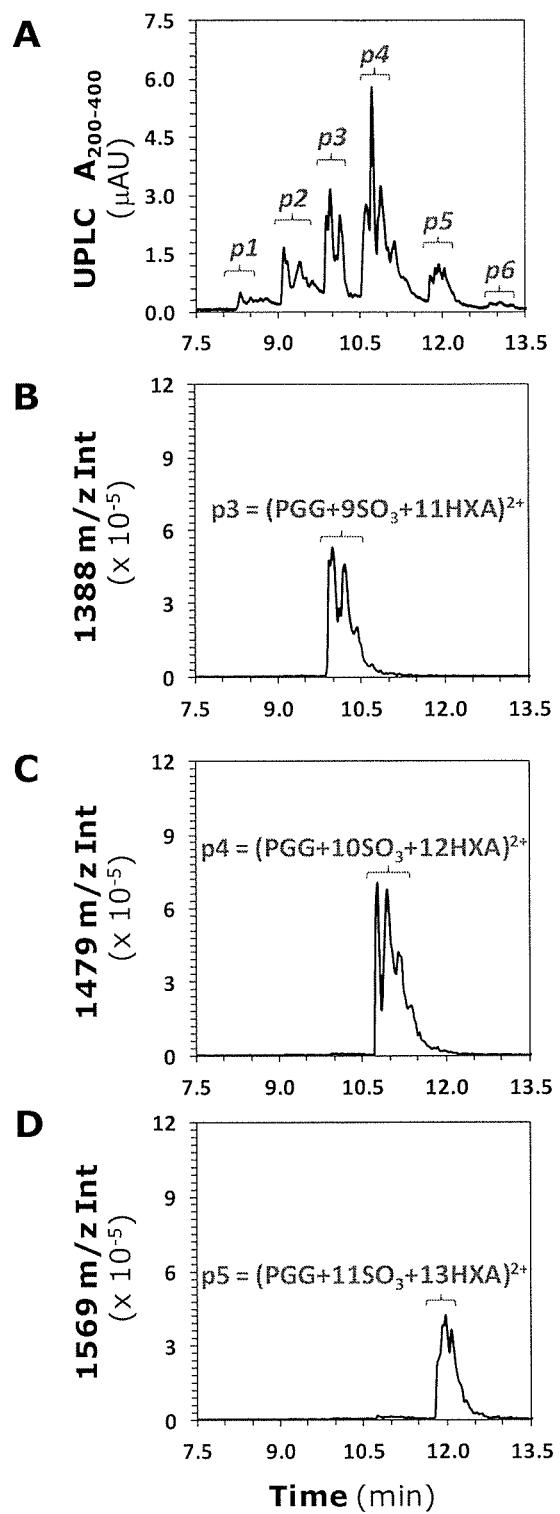
FIG. 2A-D. UPLC-MS analysis of the structure of SPGG. (A) shows UPLC resolution of SPGG into six peaks (p1 to p6), which arise from variable sulfation of the PGG scaffold. (B)-(D) show SIR monitoring of SPGG at 1388, 1479 and 1569 m/z to identify the peaks corresponding to 9, 10 and 11 sulfated PGG species. Similar SIR profiles were measured for 7, 8 and 12 sulfated species.

To identify the origin of multiple components observed within peaks p1 through p6, we utilized selective ion recording (SIR)-MS. In this technique, the spectrometer is tuned to monitor a specific ion, e.g., 1478.99 m/z corresponding to [M+10 SO$_3$+12 hexylamines]$^{2+}$ ion, resulting in the identification of all peaks that contain this molecular ion. FIG. 2 shows three SIR profiles of SPGG. Monitoring at 1388.43 m/z gave a SIR profile that essentially mimicked p3 of the UV chromatogram suggesting that each component present in the p3 peak contained nine sulfate groups. More importantly, the ion corresponding to 1388.43 was not present in any peak other than p3. Likewise, monitoring at 1478.99 or 1569.90 m/z resulted in a profile equivalent to chromatographic peaks p4 or p5, respectively. This was also found to be the case for peaks p1, p2 and p6 (not shown). To further confirm the consistency of this assignment, the synthesis of SPGG was repeated twice. An essentially similar composition of major peaks was obtained as identified by UPLC-MS and SIR analysis (not shown).

In combination, UPLC-MS coupled with SIR analysis suggested that SPGG is a mixture of septa-(p1), octa-(p2), nona-(p3), deca-(p4), undeca-(p5) and dodeca-(p6) sulfated species, which further contain sub-species with an identical number of sulfate groups. We predict that the sub-species arise due to variably positioned sulfate groups within each family of peaks. This enhances the structural diversity of SPGG. Analysis of the UPLC profile gave a composition of 6%, 17%, 21%, 45%, 11% and 3% p1 through p6, respectively (FIG. 2). Using these and their associated molecular weights, the weight-average molecular weight of SPGG was calculated to be 2178 (Na$^+$ form).

Figure 3:
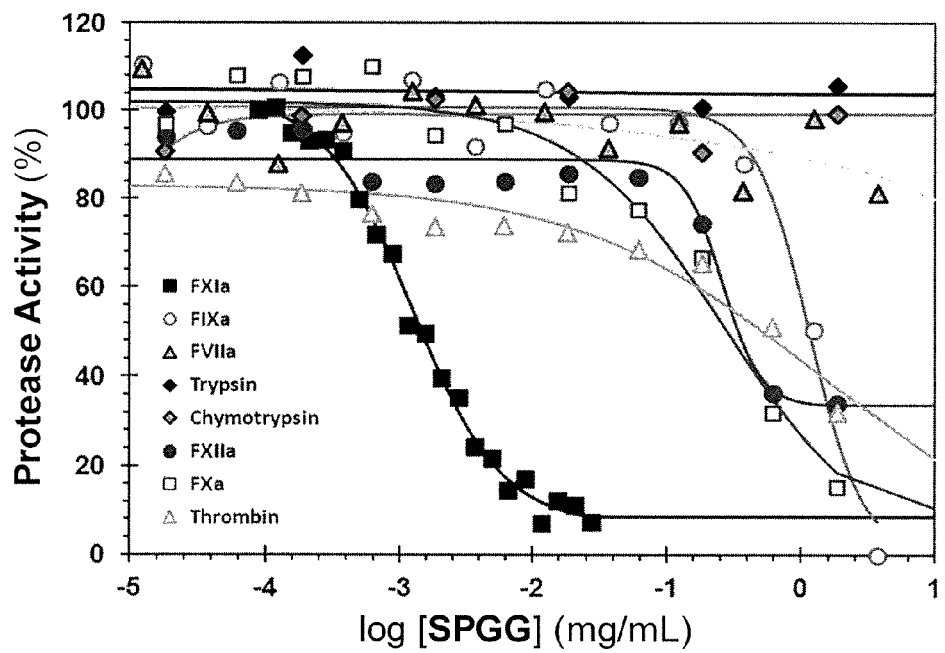
FIG. 3. Direct inhibition of coagulation and digestive proteases by SPGG. The inhibition of factor XIa (■), factor Xa (□), thrombin (Δ), factor XIIa (●), factor IXa (○), factor VIIa (▲), chymotrypsin (◇), and trypsin (◆) by SPGG was studied as described in "Experimental Procedures". Solid lines represent sigmoidal dose-response fits to the data to obtain the values of $IC_{50}$, ΔY, and HS.

Factor XIa Inhibition Potential of Synthetic, Sulfated Heparin Mimetics. Each sulfated molecule of the library was evaluated for its potential to inhibit FXIa hydrolysis of S-2366, a chromogenic small peptide substrate, at pH 7.4 and 37° C. as reported earlier.[13] Whereas the presence of SPGG resulted in a dose-dependent reduction in FXIa activity, none of the other sulfated derivatives 2, 4 or 7-14 demonstrated any effect at concentrations as high as 250 µM. The dose-dependence of FXIa activity could be fitted using the logistic equation 1, which resulted in an IC$_{50}$ of 1.2±0.1 µg/mL with an efficacy of 97% and Hill slope of 1.3 (FIG. 3, Table 1). The IC$_{50}$ values for SPGG prepared in two independent synthetic efforts was essentially identical. Taking into consideration the average molecular weight of SPGG deduced above (2178 g/mol), the IC$_{50}$ translates to 551±32 nM, which makes it the most active FXIa inhibitor reported in literature to date. The lack of inhibition potential for the SS, SCA and sulfated THIQ derivatives suggests a selective interaction between FXIa and SPGG.

TABLE 1

Inhibition profile of SPGG against coagulation and digestive proteases.$^{a,d}$

| Protease | IC$_{50}$, (µg/mL) | HS | ΔY |
|---|---|---|---|
| Factor XIa | 1.2 ± 0.03 | 1.3 ± 0.1 | 97.1 ± 3.2 |
| Factor Xa | 266 ± 31 | 0.8 ± 0.2 | 101.9 ± 3.5 |
| Factor IXa | 1141 ± 141d | 2.2 ± 0.6 | 100.6 ± 5.8 |
| Factor XIIa | 256 ± 28 | 3.0 ± 1.8 | 55.7 ± 5.9 |
| Thrombin | 1219 ± 202 | 0.5 ± 0.1 | 83 ± 10 |
| Factor VIIa | NI$^b$ | na | na |
| Trypsin | NI | na$^c$ | na |
| Chymotrypsin | NI | na | na |

$^a$The IC$_{50}$, HS, and ΔY values were obtained following non-linear regression analysis of direct inhibition of the protease. Inhibition was monitored by spectrophotometric measurement of residual proteases activity (see Experimental Procedures).
$^b$No inhibition was observed up to concentrations as high as 1.8 mg/mL for trypsin and chymotrypsin and 3.7 mg/mL for factor VIIa.
$^c$Not applicable.
$^d$Errors represent ±1 S.E.

To assess the importance of sulfate groups in SPGG, its polyphenolic precursor 5 was evaluated for inhibition of FXIa proteolytic activity. Molecule 5 was found to be completely inactive at the highest concentration tested (300 µM) highlighting the significance of sulfate groups. The result supports the idea that SPGG's heparin mimicking action is likely to be the basis for its interaction with FXIa.

Figure 4:
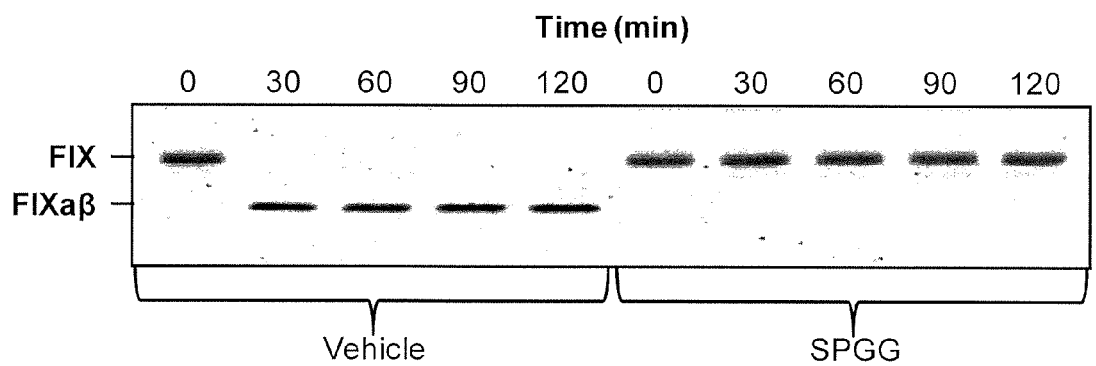
FIG. 4. Time course of FIX activation by FXIa in the presence and absence of SPGG. FIX (500 nM) in the assay buffer was incubated with FXIa (3 nM) and SPGG (0 or 3 µM) and aliquots of the reaction analyzed using standard denaturing polyacrylamide gel electrophoresis followed by Western blotting.

SPGG Inhibits Activation of Physiologically Relevant Substrate FIX by FXIa. Although SPGG inhibits FXIa hydrolysis of chromogenic substrate S-2366, FIX is the more relevant substrate of FXIa. During coagulation, FXIa activates FIX through cleavages at two sites (Arg145-Ala146 and Arg180-Val181) in rapid succession so as to generate FIXαβ, which helps form the intrinsic tenase complex eventually accelerating thrombin production. FIX binds to the A3 domain of FXIa followed by cleavages at these two sites. Such exosite-mediated associations can bring about widespread conformational changes in either proteins raising concern about the translation of SPGG inhibition of tripeptidyl substrate hydrolysis to physiological macromolecules. Hence, we measured FXIa activation of FIX in the presence and absence of SPGG using Western blotting. FIG. 4 shows the time profile of FXIa incubated with a high concentration of FIX (0.5 µM) under pseudo-first order conditions with 3 µM SPGG. The profile reveals that even after 120 min of incubation, formation of FIXαβ was not detectable, while control experiments show nearly quantitative activation of FIX within less than 30 min. Although densitometric analysis was not attempted, the study shows nearly 100% efficacy of inhibition of FIX activation by FXIa in the presence of SPGG, which is similar to that observed in hydrolysis of chromogenic substrate.

SPGG Selectively Inhibits Factor XIa Over Other Coagulation and Digestive Proteases. The inhibition profiles of SPGG against the coagulation factors IIa, VIIa, IXa, Xa, and XIIa as well as against related serine proteases of digestive system, such as trypsin and chymotrypsin, were studied using the substrate hydrolysis assays, as described earlier.[13] In these assays, the inhibition potential was determined by spectrophotometric measurement of the residual protease activity in the presence of varying concentrations of SPGG. FIG. 3 displays the decrease in the protease activity over the range of 0.01-10,000 µg/mL, which was fitted using equation 1 to calculate the IC$_{50}$ (Table 1). SPGG inhibits human factors IIa, IXa, Xa, and XIIa, although the potency (265-1219 µg/mL) is much weaker than that for FXIa. Particularly, SPGG demonstrated selectivity of 200-fold over factor XIIa, 221-fold over factor Xa, 950-fold over factor IXa, and 1016-fold over thrombin. In contrast, no inhibition was observed up to concentrations as high as 1.8 mg/mL for trypsin and chymotrypsin, and 3.7 mg/mL for factor VIIa. These results suggested that SPGG is a selective inhibitor for human FXIa.

Figure 5:
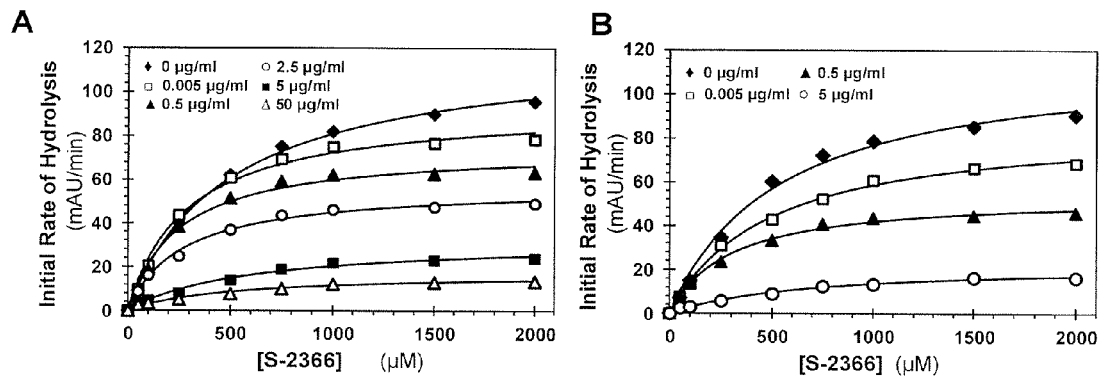
FIGS. 5A and B. Michaelis-Menten kinetics of S-2366 hydrolysis by factor XIa in the presence of SPGG. The initial rate of hydrolysis at various substrate concentrations was measured in pH 7.4 buffer as described in "Experimental Procedures" using FXIa wild type (FXIa-WT) (A) and FXIa catalytic domain (FXIa-CD) (B). The concentrations of SPGG chosen in the study were in (A) 0 (♦), 0.005 (□), 0.5 (▲), 2.5 (○), 5 (■), 50 µg/mL (Δ) and in (B) 0 (♦), 0.005 (□), 0.5 (▲), 5 µg/mL (○). Solid lines represent nonlinear regressional fits into the data by the Michaelis-Menten equation.

SPGG is an Allosteric Inhibitor of Factor XIa. To understand the mechanistic basis of inhibition, Michaelis-Menten kinetics of S-2366 hydrolysis by recombinant wild type, full-length FXIa was performed in the presence of SPGG at pH 7.4 and 37° C. In addition, a FXIa species containing only the catalytic domain, i.e., FXIa-CD, was also studied. FIG. 5 shows the initial rate profiles in the presence of 0-50 μg/mL SPGG. Each profile displays a characteristic rectangular hyperbolic dependence, which could be fitted to give the apparent $K_M$ and $V_{MAX}$ (Table 2). With wild-type FXIa, the $K_M$ for S-2366 remained essentially unchanged in the presence or absence of SPGG at ~0.5 μM, while the $V_{MAX}$ decreased steadily from 120.9 mAU/min in the absence of SPGG to 17.2 mAU/min at 50 μg/mL SPGG. Likewise, the FXIa-CD displayed an essentially similar profile. The $K_M$ for S-2366 hydrolysis in the absence of SPGG was found to be 0.53 μM, which remained invariant in the presence of SPGG (0.005 to 5.0 μg/mL). In contrast, $V_{MAX}$ decreased nearly 5-fold from 117.3 mAU/min to 22.6 mAU/min (FIG. 5, Table 2). Thus, SPGG brings about structural changes in the active site of FXIa, which does not affect the formation of Michaelis complex, but induces a significant dysfunction in the catalytic apparatus. This indicates that SPGG is an allosteric inhibitor of human FXIa. Further, the study also shows that SPGG binds to the catalytic domain to induce allosteric dysfunction.

TABLE 2

Hydrolysis of the chromogenic substrate S-2366 by human factor XIa in the presence of SPGG.[a]

|  | [SPGG] (μg/mL) | $K_M$ (mM) | $V_{MAX}$ (mAU/min) |
|---|---|---|---|
| FXIa Wild Type | 0 | 0.50 ± 0.04[b] | 120.9 ± 3.1 |
|  | 0.005 | 0.30 ± 0.03 | 93.7 ± 3.2 |
|  | 0.5 | 0.25 ± 0.03 | 74.6 ± 2.6 |
|  | 2.5 | 0.30 ± 0.03 | 56.9 ± 1.5 |
|  | 5.0 | 0.60 ± 0.10 | 32.3 ± 2.1 |
|  | 50.0 | 0.50 ± 0.10 | 17.2 ± 1.2 |
| FXIa Catalytic Domain | 0 | 0.53 ± 0.07 | 117.3 ± 5.3 |
|  | 0.005 | 0.49 ± 0.04 | 87.0 ± 2.2 |
|  | 0.5 | 0.29 ± 0.03 | 53.9 ± 1.4 |
|  | 5.0 | 0.67 ± 0.10 | 22.6 ± 1.4 |

[a] $K_M$ and $V_{MAX}$ values of S-2366 substrate hydrolysis by human factor XIa were measured as described under (Experimental Procedures). mAU indicates milliabsorbance units.
[b] Error represents ±1 S.E.

SPGG Binds in the Heparin Binding Site of Factor XIa. To assess whether SPGG is a heparin mimetic, we measured SPGG inhibition of FXIa in presence of unfractionated heparin (UFH). As discussed in the introduction, FXIa possesses two binding sites for UFH—one on the A3 domain and the other in the catalytic domain. To study competition between SPGG and UFH, we first measured the affinity of UFH to FXIa through the change in the intrinsic fluorescence of FXIa. UFH induces a saturable decrease of tryptophan fluorescence by ~15% which gave the $K_D$ of UFH-FXIa complex (1.5±0.2 μM).

Figure 6:
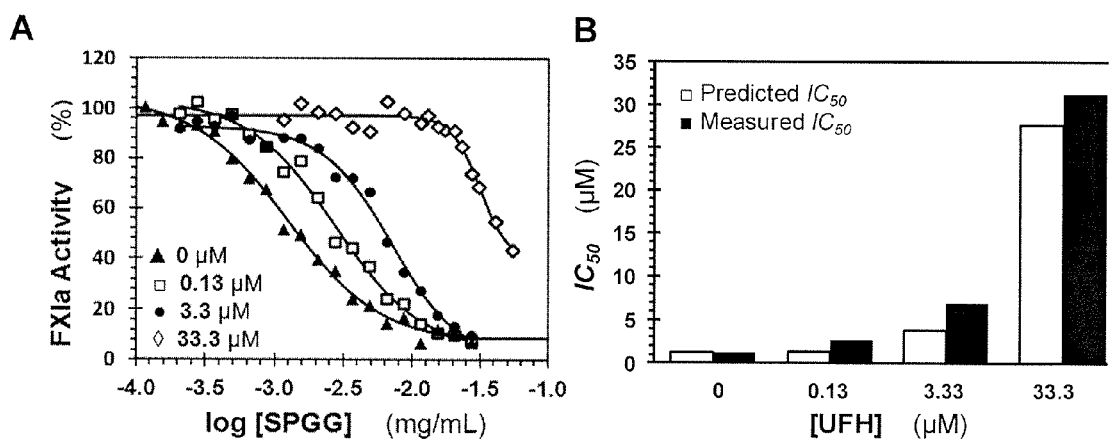
FIGS. 6A and B. Competitive direct inhibition of factor XIa by SPGG in the presence of UFH (A) and comparison of the predicted and experimentally measured $IC_{50}$ (B). Shown in A is the inhibition of factor XIa by SPGG in the presence of UFH which was determined spectrophotometrically at pH 7.4 and 37° C. Solid lines represent fits by the dose-response Eq. 1 to obtain the $IC_{50}$, predicted. The concentrations of UFH selected for the study were 0 (▲), 0.13 (□), 3.3 (●), 33.3 µM (◇). Shown in B is a comparison of the predicted and experimentally measured $IC_{50}$ values of SPGG inhibition of FXIa in the presence of UFH. Open bars represent the measured values, whereas closed bars are the values predicted using the Dixon-Webb equation.

FIG. 6A shows the change in dose-response profiles of SPGG inhibiting FXIa in the presence of UFH at pH 7.4 and 37° C. As the concentration of UFH increased from 0.13 μM to 33.3 μM, the $IC_{50}$ of FXIa inhibition increased from 1.2 μg/mL to 31.4 μg/mL (Table 3). A more quantitative test of competitive binding is the Dixon-Webb relationship, which predicts the effect of an ideal competitor on a measured parameter, e.g. $K_D$ or $IC_{50}$. Using this equation the $IC_{50, predicted}$ for SPGG inhibition of FXIa at each UFH was calculated (Table 3). FIG. 6B shows a comparison of the measured and predicted $IC_{50}$'s. Thus, SPGG inhibition of FXIa stems from binding to or in the vicinity of heparin binding site on the enzyme's catalytic domain. This implies that SPGG is an allosteric inhibitor and a small molecule heparin mimetic.

TABLE 3

Inhibition of human FXIa by SPGG in the presence of UFH at pH 7.4 and 37° C.[a]

| UFH (μM) | $IC_{50}$ (μg/mL) | HS | ΔY | $IC_{50}$, predicted (μg/mL) |
|---|---|---|---|---|
| 0 | 1.2 ± 0.03[b] | 1.3 ± 0.1 | 97.1 ± 3.2 | 1.2 |
| 0.13 | 2.7 ± 0.1 | 1.4 ± 0.2 | 99.7 ± 5.0 | 1.3 |
| 3.33 | 7.0 ± 0.3 | 1.7 ± 0.2 | 92.7 ± 6.4 | 3.9 |
| 33.3 | 31 ± 1.0 | 4.0 ± 0.9 | 58.2 ± 6.6 | 27.8 |

[a] The $IC_{50}$, HS, and ΔY values were obtained following non-linear regression analysis of direct inhibition of human factor XIa in 50 mM Tris-HCl buffer, pH 7.4, containing 150 mM NaCl, 0.1% PEG8000, and 0.02% Tween ®80 at 37° C. Inhibition was monitored by spectrophotometric measurement of residual factor XIa activity (see Experimental Procedures).
[b] Errors represent ±1 S.E.

Figure 7:
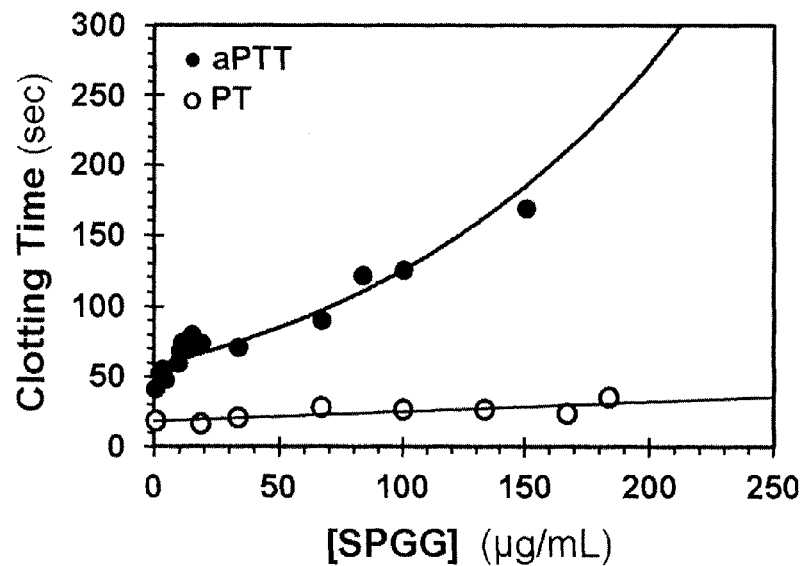
FIG. 7. Effect of SPGG on the clotting times of PT and APTT in human plasma. Prolongation of clotting time as a function of SPGG concentration in either prothrombin time assay (PT) (○) or activated partial thromboplastin time assay (APTT) (●). Solid lines are trend lines from which the concentration necessary to double clotting time was deduced.

SPGG is an Effective Anticoagulant in Human Plasma. Plasma clotting assays, prothrombin and activated partial thromboplastin time (PT and APTT, respectively), are routinely used to assess the anticoagulation potential of new enzyme inhibitors in an in vitro setting. Whereas PT measures the effect of an inhibitor on the extrinsic pathway of coagulation, APTT measures the effect on the intrinsic pathway. The concentrations of SPGG required to double PT and APTT were measured, as described earlier.[13-16] FIG. 7 shows the variation in PT and APTT in the presence of varying concentrations of SPGG. A 2-fold increase in PT required 298 μg/mL from SPGG. Likewise, a 2-fold increase in the APTT required 96 μg/mL of SPGG, only 18-fold less than that of enoxaparin, which displayed doubling of clottin time at 5.4 μg/mL in a similar assay.[13] In comparison, the APTT and PT values for molecules 2 and 4 were much higher (not shown). At molar levels, SPGG turns out to be 36-fold less effective than enoxaparin. These results indicate that chemically synthesized SPGG has good anticoagulation properties in human plasma.

Figure 8:
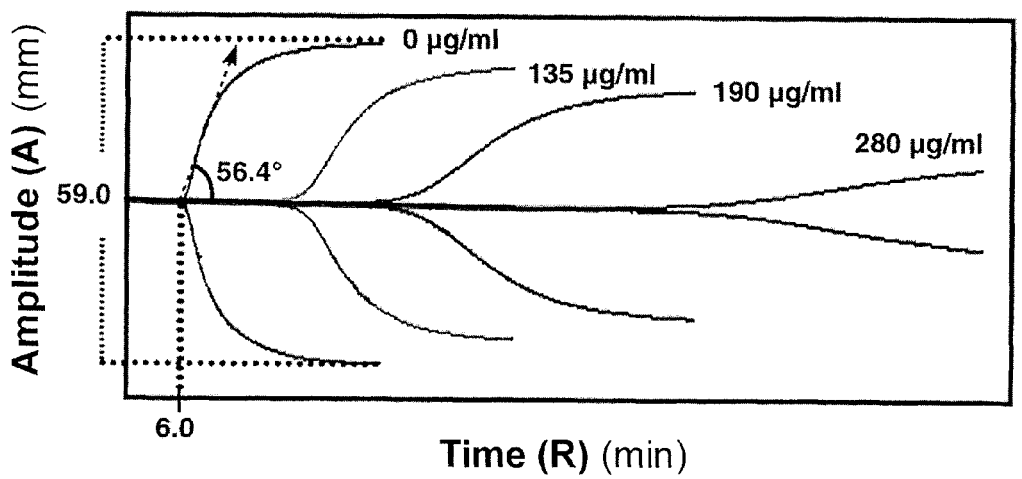
FIG. 8. Thromboelastography analysis of clot formation in the presence of SPGG. Comparison of the effect of SPGG and enoxaparin on clot formation in whole blood using thromboelastography analysis. A typical thromboelastogram expected of any anticoagulant is described by R, α, MA, and G parameters.

SPGG is an Effective Anticoagulant in Human Whole Blood as Indicated by Thromboelastography. To assess the anticoagulation properties of SPGG in human whole blood, thromboelastography was employed. This technique is an ex vivo protocol often utilized to evaluate the anticoagulant activity of low molecular weight heparins (LMWHs) in whole blood.[13-16] Thromboelastography monitors the thrombodynamic properties of blood as it is induced to clot under a low shear environment resembling sluggish venous flow. These thrombodynamic properties are expected to dramatically change in presence of anticoagulant in blood. The blood clot formation is recorded as a force transduced on a pin at the center of a blood-containing cup. The kinetics of clot formation and growth as well as the strength and stability of the formed clot are measured through parameters such as maximum amplitude (MA) of clot formation; shear elastic modulus strength (G) of clot; the reaction time (R) for the start of clotting; and the angle α, which is a measure of fibrin build-up and cross-linking (FIG. 8).

Table 4 shows the effects of SPGG and enoxaparin in human whole blood with respect to the changes in R, α, MA, and G parameters. For both anticoagulants, increasing the concentration increases R and decreases a, MA, and G parameters. Briefly, R increases from 6.0 min to 87.1 min as the concentration of SPGG increases from 0 μg/mL to 280 μg/mL, while α decreases from 56.4° to less than 9.4° suggesting a significant decrease in the fibrin polymerization and network formation. Enoxaparin demonstrates similar effect on R and a parameters, except it exhibits such effects at a range of 0 to 4.5 µg/mL.[13] Over the same range, enoxaparin decreases MA and G measurements by about 1.5- and 2-fold, respectively. In similar fashion, SPGG reduces MA and G by ~4- to 8-fold over the concentration range of 0-280 µg/mL. These results suggest that SPGG is a good anticoagulant in human whole blood.

TABLE 4

Human whole blood clotting parameters of SPGG by thromboelastography.[a]

|  | Concentration (µg/mL) | $R^b$ (min) | $\alpha^b$ (degs) | $MA^b$ (mm) | $G^b$ (kDynes/cm$^3$) |
| --- | --- | --- | --- | --- | --- |
| SPGG | 0 | 6.0[c] | 56.4 | 59 | 7.2 × 10$^3$ |
|  | 20[d] | 6.6 | 51.4 | 62 | 8.2 × 10$^3$ |
|  | 135 | 22.8 | 30.6 | 49.8 | 5.0 × 10$^3$ |
|  | 190 | 37.8 | 9.4 | 43.5 | 3.8 × 10$^3$ |
|  | 280 | 87.1 | ND[e] | 15.1 | 0.9 × 10$^3$ |
| Enoxaparin | 0 | 7.0 | 59.0 | 56.5 | 6.5 × 10$^3$ |
|  | 1.35 | 8.0 | 49.0 | 51.0 | 5.2 × 10$^3$ |
|  | 2.7 | 11.5 | 43.0 | 47.0 | 4.4 × 10$^3$ |
|  | 3.4 | 14.0 | 41.0 | 46.0 | 4.3 × 10$^3$ |
|  | 4.5 | 17.0 | 31.5 | 42.0 | 3.6 × 10$^3$ |

[a]Thromboelastography parameters were obtained in an automated manner from the TEG Coagulation Analyzer. See Experimental Procedures for a description of the setup.
[b]Parameters obtained from this analysis were R (Reaction time which is the time interval between the initiation of coagulation and the appearance of first detectable signal of no less than 2 mm in amplitude), α (Angle which is the acute angle between an extension of the R value tracing and the tangent of the maximum slope produced by the TEG tracing), MA (Maximum amplitude which is the maximum distance the pin of TEG moves at the end), and G (The shear elastic modulus strength which is a calculated parameter (G = 5000 × MA/(100 − MA) and is a measure of clot strength).
[c]The reported values are the mean of two independent experiments which were recorded automatically. SD in each case was less than 10%.
[d]This concentration of SPGG is not graphically plotted in FIG. 6.
[e]Not determined.

Figure 9:
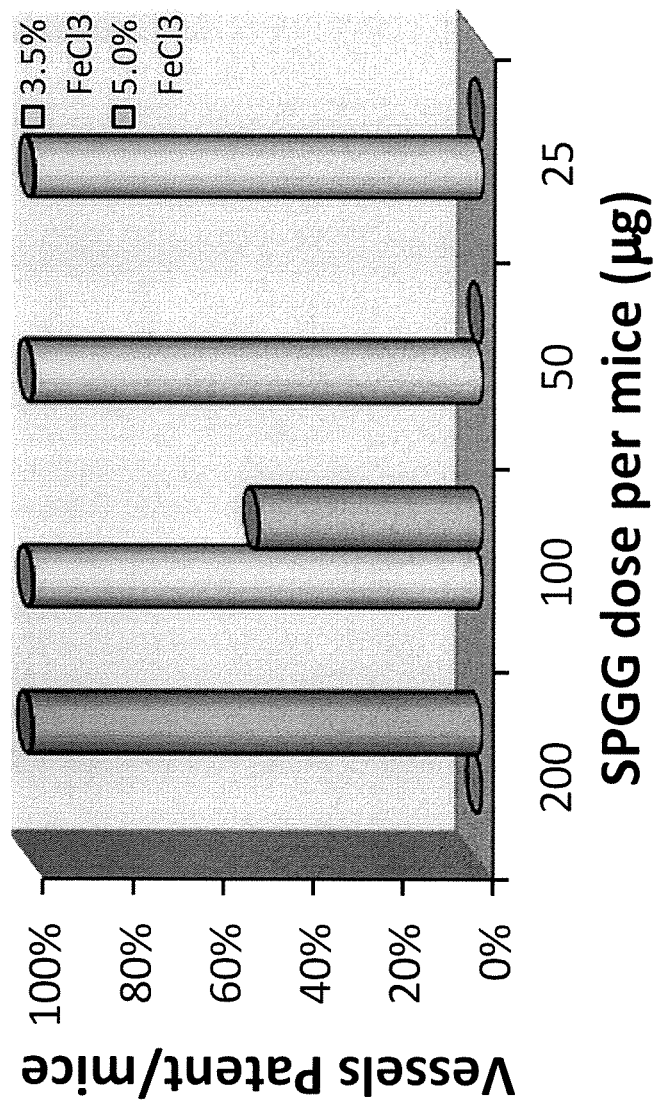
FIG. 9. In vivo antithrombotic activity of SPGG in murine carotid artery model.

SPGG is Antithrombotic in Murine Carotid Artery Thrombosis Model To assess whether the ex vivo activity of these molecules is translated into in vivo systems, we studied SPGG as a representative potent factor XIa inhibitor. The antithrombotic effect of SPGG was tested in well-characterized arterial thrombosis models[22,23]. Exposure of the carotid artery of C57Bl/6 mice to FeCl$_3$ (either 3.5% or 5.0%) results in formation of an occlusive platelet-rich thrombus within 15 minute. A 0.025 to 0.2 mg dose of SPGG injected 10 min before application of FeCl$_3$ prevents arterial occlusion in a dose dependent manner (FIG. 9). At doses of 0.025 to 0.2 mg, thrombosis was prevented in ~100% arteries at 3.5% FeCl$_3$, while a dose of 0.2 mg protected all vessels from occlusion at 5.0% FeCl$_3$.

This demonstrates that SPGG exhibits potent in vivo anti-thrombotic activity.

Discussion

SPGG is thus a potent anticoagulant in vitro, ex vivo and in vivo. SPGG selectively inhibits FXIa with an excellent in vitro potency of 1.2 µg/mL (~550 nM). Importantly, SPGG inhibition of small molecule hydrolysis remains true also for FXIa's physiological substrate, FIX, which forms the foundation for the anticoagulant activity observed in human plasma and blood.

A unique and important advantage of SPGG is that it is readily synthesizable. In this work, SPGG was chemically synthesized in one step from the commercially available polyphenolic precursor, pentagalloyl glucoside. This precursor can be easily isolated from natural sources in good yields[18, 19] or could be prepared by methanolysis of the naturally abundant tannic acid.[20, 21] Thus, SPGG can be obtained on a large scale in relatively inexpensive manner.

Michaelis-Menten kinetics revealed a classic allosteric inhibition mechanism, a mechanistic aspect that adds significantly to clinical viability is allostery, advantageously offering a unique opportunity of highly selective recognition. In addition, an interesting advantage of allosteric inhibitors is the ability to develop tunable modulation. Because allostery involves coupling of two distant sites, i.e., the ligand binding site and the biological response site, the nature, extent and mechanism of coupling is significantly dependent on the structure of the ligand. Whereas some allosteric modulators may induce nearly 100% inhibition, others may only be partially efficacious. The efficacy of SPGG inhibition of hydrolysis of chromogenic substrate as well as FIX by FXIa is nearly 100%. SPGG derivatives that display variable efficacy may be synthesized.

Overall, SPGG is the first allosteric inhibitor of factor XIa that displays good potency in ex vivo and in vivo anticoagulation assays/model systems. It possesses many advantages including relatively easy synthesis, allosteric recognition, and high specificity of targeting FXIa.

REFERENCES FOR EXAMPLE 1

1. Baglia, F. A.; Gailani, D.; López, J. A.; Walsh, P. N. Identification of a binding site for glycoprotein Ibalpha in the Apple 3 domain of factor XI. J. Biol. Chem. 2004, 279, 45470-45476.
2. Baglia, F. A.; Shrimpton, C. N.; Emsley, J.; Kitagawa, K.; Ruggeri, Z. M.; López, J. A.; Walsh, P. N. Factor XIainteracts with the leucine-rich repeats of glycoprotein Ibaipha on the activated platelet. J Biol Chem. 2004, 279, 49323-49329.
3. Ho, D. H.; Badellino, K.; Baglia, F. A.; Walsh, P. N. A binding site for heparin in the apple 3 domain of factor XI. J. Biol. Chem. 1998, 273, 16382-16390.
4. Zhao, M.; Abdel-Razek, T.; Sun, M. F.; Gailani, D. Characterization of a heparin-binding site on the heavy chain of factor XI. J. Biol. Chem. 1998, 273, 31153-31159.
5. Badellino, K. O.; Walsh, P. N. Localization of a heparin binding site in the catalytic domain of FXIa. Biochemistry 2001, 40, 7569-7580.
6. Sinha, D.; Badellino, K. O.; Marcinkiewicz, M.; Walsh, P. N. Allosteric modification of factor XIa functional activity upon binding to polyanions. Biochemistry 2004, 43, 7593-7600.
7. Yang, L.; Sun, M. F.; Gailani, D.; Rezaie, A. R. Characterization of a heparin-binding site on the catalytic domain of factor XIa: mechanism of heparin acceleration of factor XIa inhibition by the serpins antithrombin and C1-inhibitor. Biochemistry 2009, 48, 1517-1524.
8. Sun, M. F.; Zhao, M.; Gailani, D. Identification of amino acids in the Factor XIapple 3 domain required for activation of factor IX. J. Biol. Chem. 1999, 274, 36373-36378.
9. Al-Horani, R. A.; Liang, A.; Desai, U. R. Designing nonsaccharide allosteric activators of antithrombin for accelerated inhibition of factor Xa. J. Med. Chem. 2011, 54, 6125-6138.
10. Al-Horani, R. A.; Desai, U. R. Electronically rich N-substituted tetrahydroisoquinoline-3-carboxylic acid esters: Concise synthesis and conformational studies. Tetrahedron, 2012, 68, 2027-2040.
11. Raghuraman, A.; Riaz, M.; Hindle, M.; Desai, U. R. Rapid, high-yielding microwave-assisted per-sulfation of organic scaffolds. Tetrahedron Lett. 2007, 48, 6754-6758.

12. Henry, B. L.; Thakkar, J. N.; Liang, A.; Desai U. R. Sulfated, low molecular weight lignins inhibit a select group of heparin-binding serine proteases. Biochem. Biophys. Res. Commun. 2012, 417, 382-386.
33. Henry, B. L.; Thakkar, J. N.; Martin, E. J.; Brophy, D. F.; Desai, U. R. Characterization of the plasma and blood anticoagulant potential of structurally and mechanistically novel oligomers of 4-hydroxycinnamic acids. Blood Coagul. Fibrin. 2009, 20, 27-34.
14. Correia-da-Silva, M.; Sousa, E.; Duarte, B.; Marques, F.; Carvalho, F.; Cunha-Ribeiro, L. M.; Pinto, M. M. Flavonoids with an oligopolysulfated moiety: a new class of anticoagulant agents. J. Med. Chem. 2011, 54, 95-106.
15. Correia-da-Silva, M.; Sousa, E.; Duarte, B.; Marques, F.; Carvalho, F.; Cunha-Ribeiro, L. M.; Pinto, M. M. Polysulfated xanthones: multipathway development of a new generation of dual anticoagulant/antiplatelet agents. J. Med. Chem. 2011, 54, 5373-5384.
16. Correia-da-Silva, M.; Sousa, E.; Duarte, B.; Marques, F.; Cunha-Ribeiro, L. M.; Pinto, M. M. Dual anticoagulant/antiplatelet persulfated small molecules. Eur. J. Med. Chem. 2011, 46, 2347-2358.
17. Gunnarsson, G. T.; Desai, U. R. Designing small, non-sugar activators of antithrombin using hydropathic interaction analyses. J. Med. Chem. 2002, 45, 1233-1243.
18. Haslam, E. Plant Polyphenols: Vegetable Tannins Revisited; Cambridge University Pres: Cambridge, U.K., 1981; pp. 1-13, 90-153.
19. Xu, S.-J.; Yang, L.; Zeng, X.; Zhang, M.; Wang, Z.-T. Characterization of compounds in the Chinese herbal drug Mu-Dan-Pi by liquid chromatography coupled to electrospray ionization mass spectrometry. Rapid Commun. Mass Spectrom. 2006, 20, 3275-3288.
20. Hagerman, A. E.; Zhao, Y.; Johnson, S. Methods for determination of condensed and hydrolysable tannins. In: Antinutrients and Phytochemicals in Foods. (Shahadi, F. ed.) ACS, Washington D.C., 1997; pp. 209-222.
21. Chen, Y.; Hagerman, A. E. Characterizing soluble noncovalent complexes between bovine serum albumin and β-1,2,3,4,6-penta-O-galloyl-D-glucopyranose by MALDI-TOF mass spectroscopy. J. Agric. Food Chem. 2004, 52, 4008-4011.
22. Wang, X.; Cheng, Q.; Xu, L.; Feuerstein, G. Z.; Hsu, M. Y.; Smith, P. L.; Seiffert, D. A.; Schumacher, W. A.; Ogletree, M. L.; Gailani, D. J Thromb Haemost 2005, 3, 695-702.
23. Cheng, Q.; Tucker, E. I.; Pine, M. S.; Sisler, I.; Matafonov, A.; Sun, M. F.; White-Adams, T. C.; Smith, S. A.; Hanson, S. R.; McCarty, O. J.; Renné, T.; Gruber, A.; Gailani, D.; Blood 2010, 116, 3981-3989.

Example 2

Allosteric Modulators of Factor XIa that Target Hydrophobic Domains Adjacent to its Heparin-Binding Site: Sulfated Quinazolinones Glycosaminoglycan (GAG)-binding proteins (GBPs) play critical roles in a number of physiological and pathological responses such as coagulation, immune regulation, angiogenesis, morphogenesis, viral infection and cancer. The modulation of these responses by GAGs such as heparin, heparan sulfate (HS) and chondroitin sulfate offers major opportunities for discovering a large number of therapeutic agents considering that GAGs present a wide range of structures for protein recognition. Yet, only one interaction, the heparin-antithrombin interaction, has yielded a clinically useful agent.

A major problem in discovering GAG-based molecules, e.g., heparin oligomers, as drugs is the rather poor specificity of their interaction with proteins. Although the presence of certain rare residues in heparin/heparan sulfate (H/HS) chains, such as 3-O-sulfated glucosamine or 2-O-sulfated glucuronic acid, is believed to indicate specificity, the majority of HS-protein interactions are likely to be non-selective because the nature of forces that govern these interactions is primarily electrostatic, which is non-directional and operational over long distances. This implies that H/HS recognize practically any collection of electropositive residues, i.e., a group of arginines and lysines, which severely limits the discovery of highly selective modulators. The art suffers severely from the lack of a generalizable strategy for the rational design of modulators of GAG-protein interactions. In fact, no real 'design' has been utilized in developing the polymeric polyanions, while the computational design of sulfated, small molecule antithrombin activators is highly case-specific. A rational, more broadly applicable strategy would greatly help in developing selective sulfated modulators of GBPs.

Figure 10:
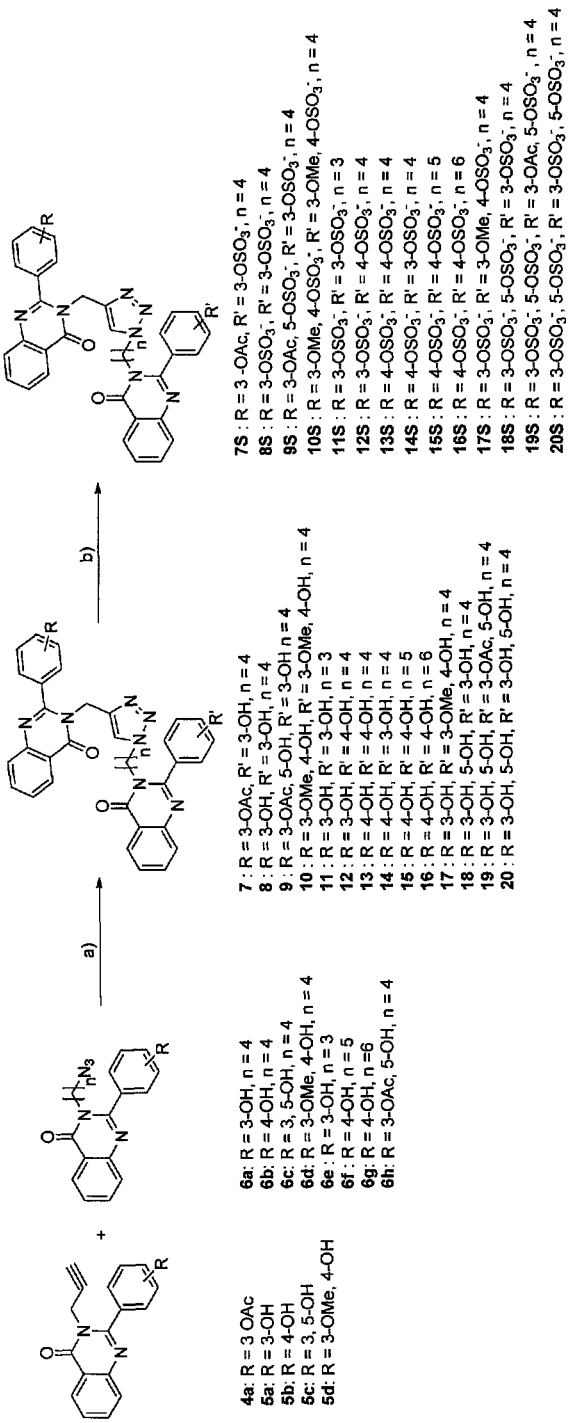
FIG. 10. Scheme 2 of Example 2. Synthesis of sulfated QAOs 7S-20S.
Figure 11:
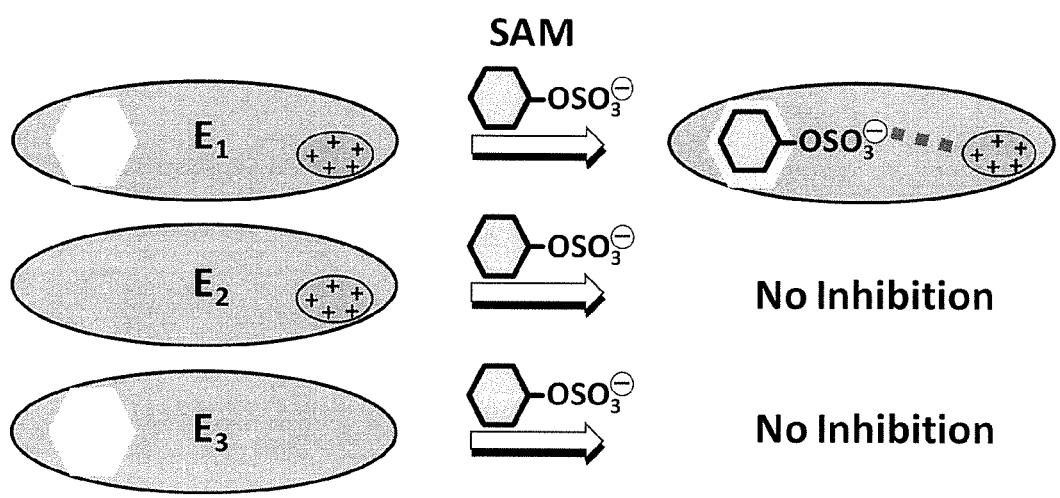
FIG. 11. Strategy for the design of a sulfated allosteric modulator (SAM) of a glycosaminoglycan-binding protein (GBP) exploiting the difference in hydrophobicity (hP, shown as light colored patch) on the periphery of a heparin-binding site (HBS, shown as blue ellipse with positive charges). A SAM binds an enzyme (shown by red dashed line), e.g., E1, only if it contains both hP and HBS. E2 and E3 do not recognize the SAM because of an absence of either hP or HBS. This generates selectivity of recognition.

Certain aspects of the invention are based on the design of molecules that specifically target the hydrophobic domain surrounding the heparin-binding site (HBS) of proteins. In fact, coagulation enzymes possess hP domains of varying sizes around their strongly electropositive HBSs. For example, thrombin contains two clusters of hP residues near its HBS, while the corresponding site in factor XIa is significantly different. Herein is described the development of molecules, herein called sulfated allosteric modulators (SAMs), by exploiting differential recognition of hP patches around the HBS. The strategy involves 1) initial attraction of an anionic sulfate group present on a SAM to one or more arginines/lysines present in the HBS of a heparin-binding protein (HBP) followed by 2) recognition of an adjacent hP patch on the HBP to form a complex (FIG. 10). Enzymes devoid of either the HBS or the hP domain would not bind the SAM, and hence escape inhibition. Only enzymes possessing the HBS and an appropriate hP domain will be targeted by SAMs. The potency of inhibition will be dependent on the complementarity of SAM's hydrophobic scaffold with the hP domain on the enzyme. In essence, this strategy revolves around electronic steering of a small molecule to the HBS of the protein due to non-directionality of an initial, weak ionic bond followed by filtering and tight locking of an optimal hydrophobic SAM scaffold. This work describes the discovery of SAMs of human factor XIa.

Experimental Procedures

Chemicals, Reagents and Analytical Chemistry. Anhydrous $CH_2Cl_2$, THF, $CH_3CN$, DMF, DMA and acetone were purchased from Sigma-Aldrich (Milwaukee, Wis.) or Fisher (Pittsburgh, Pa.) and used as such. Other solvents used were of reagent gradient and used as purchased. Analytical TLC was performed using UNIPLATE™ silica gel GHLF 250 um pre-coated plates (ANALTECH, Newark, Del.). Column chromatography was performed using silica gel (200-400 mesh, 60 Å) from Sigma-Aldrich. Chemical reactions sensitive to air or moisture were carried out under nitrogen atmosphere in oven-dried glassware. Reagent solutions, unless otherwise noted, were handled under a nitrogen atmosphere using syringe techniques. Flash chromatography was performed using Teledyne ISCO (Lincoln, Nebr.) Combiflash RF system and disposable normal silica cartridges of 30-50μ particle size, 230-400 mesh size and 60 Å pore size.

The flow rate of the mobile phase was in the range of 18 to 35 ml/min and mobile phase gradients of ethyl acetate/hexanes and $CH_2Cl_2/CH_3OH$ were used to elute compounds. Proteins and Chromogenic Substrates were as described for Example 1, and trypsin substrate (S-2222, Benzyl-Ile-Glu(—OH and —$OCH_3$)-Gly-Arg-p-nitroanilide.HCl) was obtained from Diapharma (West Chester, Ohio).

Chemical Characterization of Compounds. $^1H$ and $^{13}C$ NMR were carried out as described for Example 1. For HRMS measurements, a Perkin Elmer AxION 2 TOF MS was used in negative ion mode. Ionization conditions on both instruments were optimized for each compound to maximize the ionization of the parent ion. Generally, the extractor voltage was set to 3 V, the Rf lens voltage was 0.1 V, the source block temperature was set to 150° C., and the desolvation temperature was about 250° C. The purity of each final compound was greater than 95% as determined by uPLC-MS.

General Procedure for Synthesis of Sulfated Quinazolin-4(3H)-Ones. Sulfation of phenolic precursors was achieved using microwave assisted chemical sulfation as described earlier.[4,5] Briefly, to a stirred solution of polyphenol in anhydrous $CH_3CN$ (1-5 mL) at room temperature $Et_3N$ (10 equvi per —OH group) and $Me_3N:SO_3$ complex (6 equvi per —OH) was added. The reaction vessel was sealed and micro-waved (CEM Discover, Cary, N.C.) for 30 min at 90° C. The reaction mixture was cooled and transferred to a round bottom flask and volume reduced as much as possible under low pressure conditions at 25° C. The reaction mixture was then directly loaded on to a flash chromatography column and purified using dichloromethane and methanol solvent system (5-20%) to obtain the sulfated QAOs. The samples were concentrated and re-loaded onto a SP Sephadex C-25 column for sodium exchange. Appropriate fractions were pooled, concentrated in vacuo, and lyophilized to obtain a white powder. Nuclear magnetic resonance spectral characteristics of all the sulfated compounds 3aS-3gS, 7S-20S, and 25S-29S were consistent with the proposed formulas.

Direct Inhibition of Factor XIa by Sulfated QAOs was performed as described in Example 1.

Inhibition of Proteases of the Coagulation and Digestive Systems by 16S. The inhibition potential of 500 μM SAM (16S, 15S, 13S) against coagulation enzymes including thrombin and factor Xa and digestive enzymes including trypsin and chymotrypsin was evaluated using chromogenic substrate hydrolysis assays reported in the literature.[2,3,6] These assays were performed using substrates appropriate for the enzyme being studied under conditions closest to the physiological condition (37° C. and pH 7.4), except for thrombin, which was performed at 25° C. and pH 7.4. The concentrations of enzymes and substrates in microplate wells, respectively, were: 6 nM and 50 μM for thrombin; 1.09 nM and 125 μM for factor Xa, 2.5 ng/ml and 80 μM for bovine trypsin; and 500 ng/ml and 240 μM for bovine chymotrypsin. The ratio of the proteolytic activity of an enzyme in the presence of the sulfated QAO to that in its absence was used to calculate percent inhibition (%).

Michaelis-Menten Kinetics of Substrate Hydrolysis in Presence of 14S was performed as in Example 1. The initial rate was measured as a function of various concentrations of the substrate (0.01-1.6 mM) in the presence of fixed concentration of 14S in 50 mM TrisHCl buffer, pH 7.4, containing 150 mM NaCl, 0.1% PEG8000, and 0.02% Tween®80 at 37° C.

Thermodynamics of Sulfated QAOs Binding to Human Factor XIa. Fluorescence experiments were performed using a QM4 spectrofluorometer (Photon Technology International, Birmingham, N.J.) in 50 mM Tris-HCl buffer of pH 7.4 containing 150 mM NaCl and 0.1% PEG8000 at 37° C. Fluorescence emission spectra of active site labeled FXIa, i.e., FXIa-DEGR (250 nM), in the absence and presence of saturating concentrations of sulfated QAOs (13S, 14S, 15S, and 16S) were recorded using an excitation wavelength of 345 nm. The emission scan range was set to 350-600 nm in increments of 1 nm. The excitation and emission slit widths were set at 1 mm and 1.5 mm, respectively. The equilibrium dissociation constant ($K_D$) of sulfated QAOs-FXIa complex was measured using the change in the fluorescence of the active site dansyl group due to binding. Titrations were performed by adding aliquots of a solution of sulfated QAOs (13S, 14S, 15S, and 16S) in the above buffer to a fixed concentration of FXIa-DEGR (250 nM) and monitoring the change in the fluorescence of FXIa-DEGR at 547 nm ($\lambda_{EX}$=345 nm). The slit widths on the excitation and emission side were 1 and 1.5 mm, respectively. The change in fluorescence at 547 nm was fitted using the standard Hill equation for ligand binding for cooperative binding to obtain the apparent dissociation constant ($K_{D,app}$) of binding. In this equation, ΔF represents the change in fluorescence following addition of sulfated QAO from the initial fluorescence ($F_0$), while $\Delta F_{MAX}$ represents the maximal change in fluorescence. Hill coefficient 'n' is a measure of the cooperativity of binding. Each measurement was performed at least twice.

Prothrombin Time (PT) and Activated Partial Thromboplastin Time (APTT) were assessed as described in Example 1.

Mutagenesis and Expression of Recombinant Factor XIa. Mutations in the FXIa 170 helix were introduced into a modified human FXI cDNA (FXI-Ser-362,482), which contains serine substitutions for Cys362 and Cys482 (FXI numbering), as described earlier in several papers.[7,8] A disulfide bond between these residues connects the heavy chains and catalytic domains after cleavage at the activation site, and eliminating the bond allows the catalytic domain of FXIa (FXIa-CD) to separate from the heavy chain. The basic residues of the FXIa 170-helix, Lys529, Arg530, Arg532, Lys535 and Lys539 in the FXI numbering system (correspond to residues 170, 171, 173, 175 and 179 in the chymotrypsinogen numbering system), were changed to alanine individually and as a group using a Quick Change kit (Stratagene, La Jolla, Calif.). cDNAs in expression vector pJVCMV were used to transfect HEK-293 cells as described. Stably expressing clones were expanded in 175 cm² flasks, and serum free media (Cellgro Complete, Mediatech, Herndon, Va.) was collected every 48 hours, supplemented with benzamidine (5 mM) and stored at −80° C. pending purification. Recombinant FXI was purified from conditioned media on an anti-fXI IgG 1G5.12 affinity column. After loading, the column was washed with 25 mM Tris-HCl, pH 7.4, 100 mM NaCl, and eluted with 2M NaSCN in the same buffer. Protein containing fractions were pooled, concentrated and dialyzed, and protein concentrations were determined by dye-binding assay (Bio-Rad). Recombinant wild-type FXI or FXI-CD (~200-300 μg/ml) was activated with 5 μg/ml FXIIa at 37° C. Completion of activation was confirmed by SDS-PAGE. Activated preparations were passed over a 1G5.12 column to separate the protease from FXIIa. In the case of proteins prepared in FXI-Ser-362,482, the catalytic domains bind to the column, while the heavy chain passes through.

Results and Discussion

Synthesis of the Library of QAOs. To put the dual element hypothesis of FIG. 10 to test, we synthesized a library of 26 quinazolin-4(3H)-ones (QAOs) including 7 monomers and 19 dimers containing one to four sulfate groups. The QAO core structure is a well-known hP scaffold with three-dimensional similarity to the flavonoid scaffold studied earlier as a HBS ligand. The QAO core scaffold was synthesized using a condensation reaction between anthranilamide and suitably substituted benzaldehyde[9] to obtain QAO monomers 3a-3g containing one or two phenolic groups (Scheme 1 of this Example). This is a fairly well-established thermal cyclo-dehydration reaction. Yet, the reaction yields decrease as the number of phenolic groups increase restricting the library diversity to two phenolic groups on the scaffold. Monomers 3a-3g were sulfated under microwave conditions[4,5] to yield the corresponding sulfated derivatives 3aS-3gS in 85-90% yields. Sulfation changes the physicochemical characteristics of QAO scaffold by introducing significant water solubility. Water-soluble sulfated molecules have been previously purified using size exclusion chromatography.[4,5] However, the considerable hydrophobicity of the QAO scaffold allowed for the use of traditional dichloromethane-methanol solvent system using flash chromatography. This greatly eased handling of these highly polar compounds. The sulfated QAOs were characterized using $^1H$ and $^{13}C$ NMR, and ESI MS techniques.

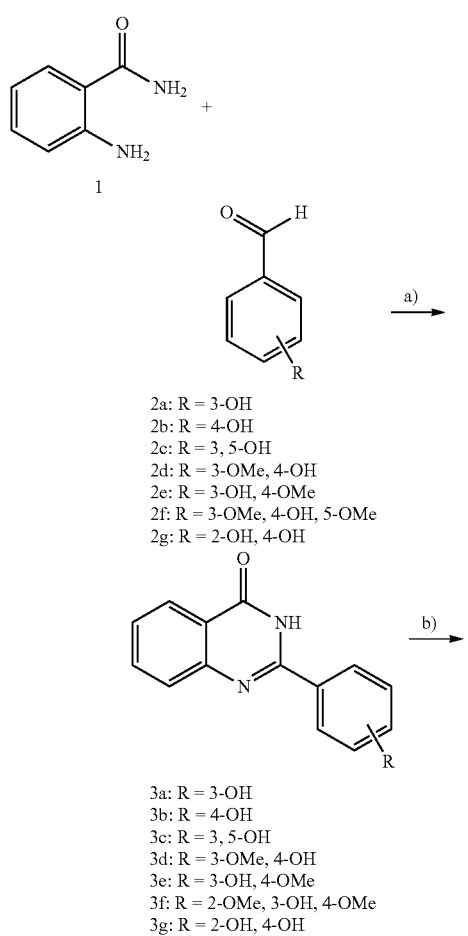

Scheme 1 of Example 2. Synthesis of monomeric sulfated quinazolin-4(3H)-ones (QAOs).

2a: R = 3-OH
2b: R = 4-OH
2c: R = 3, 5-OH
2d: R = 3-OMe, 4-OH
2e: R = 3-OH, 4-OMe
2f: R = 3-OMe, 4-OH, 5-OMe
2g: R = 2-OH, 4-OH

3a: R = 3-OH
3b: R = 4-OH
3c: R = 3, 5-OH
3d: R = 3-OMe, 4-OH
3e: R = 3-OH, 4-OMe
3f: R = 2-OMe, 3-OH, 4-OMe
3g: R = 2-OH, 4-OH

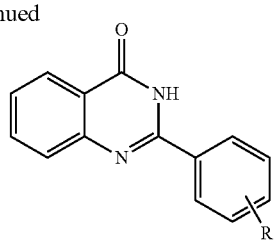

3aS: R = 3-$OSO_3^-$
3bS: R = 4-$OSO_3^-$
3cS: R = 3, 5-$OSO_3^-$
3dS: R = 3-OMe, 4-$OSO_3^-$
3eS: R = 3-$OSO_3^-$, 4-OMe
3fS: R = 3-OMe, 3-$OSO_3^-$, 5-OMe
3gS: R = 2-$OSO_3^-$, 4-$OSO_3^-$ a) $NaHSO_3$, DMA, reflux/overnight, 65-80%; b) $SO_3:Me_3N$, TEA, $CH_3CN$, microwave/30min, 85-90%

To develop a more diverse library, dimerization of the monomeric scaffold was desirable. A rather simple tool for generating a dimeric equivalent is the copper-catalyzed azide-alkyne cycloaddition (CuAAC) reaction.[10] Thus, QAO alkynes 4a-5d and azides 6a-6h (Scheme 2, presented in FIG. 10) were synthesized from corresponding monomers 3a-3d using acetylation of phenolic group followed by standard nucleophilic displacement strategy and deacetylation in excellent yields, as described below:

General Procedure for Synthesis of Substituted Phenyl Quinazolin-4(3H)-One (3a-3g): To a stirred solution of anthranilamide 1 (1.0 equiv) in anhydrous N, N'-dimethylacetamide, substituted benzaldehyde 2a-2g (1.1 equiv) and sodium bisulfate (1.5 equiv) was added in a single neck flask attached with a reflux condenser. The reaction mixture was vigorously stirred at 145° C. for 12 h; the reaction mixture was diluted with EtOAC (25 mL) and water (25 mL). The organic layer was separated and the aqueous phase was extracted with EtOAc (2×25 mL). The organic extracts were combined, washed with saturated NaCl solution (25 mL), and dried over anhydrous $Na_2SO_4$. Removal of the solvent under reduced pressure fallowed by the purification of the crude by flash chromatography on silica gel (10-80% ethyl acetate in hexanes) afforded 2-aryl quinazolin-4(3H)-one 3a-3g. Spectral (e.g. $^1H$ NMR) characteristics of all the following quinazolinone compounds were consistent with their predicted formulas:

2-(3-hydroxylphenyl) quinazolin-4(3H)-one (3a);

2-(4-hydroxylphenyl)quinazolin-4(3H)-one (3b);

2-(3, 5-dihydroxyphenyl)quinazolin-4(3H)-one (3c);

2-(4-hydroxy-3-methoxyphenyl)quinazolin-4(3H)-one (3d);

2-(3-hydroxy-4-methoxyphenyl)quinazolin-4(3H)-one (3e);

2-(4-hydroxy-3, 5-dimethoxyphenyl)quinazolin-4(3H)-one (30; and 2-(2, 4-dihydroxyphenyl)quinazolin-4(3H)-one (3g).

Synthesis of Propargylated Quinazolinones.

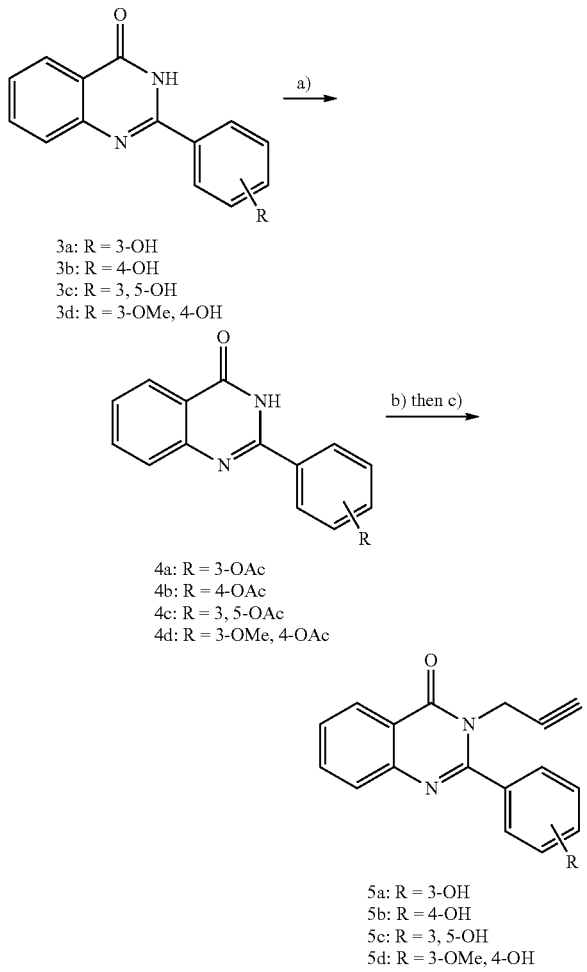

Scheme 3 of Example 2.

3a: R = 3-OH
3b: R = 4-OH
3c: R = 3, 5-OH
3d: R = 3-OMe, 4-OH

4a: R = 3-OAc
4b: R = 4-OAc
4c: R = 3, 5-OAc
4d: R = 3-OMe, 4-OAc

5a: R = 3-OH
5b: R = 4-OH
5c: R = 3, 5-OH
5d: R = 3-OMe, 4-OH a) Ac$_2$O, TEA, DCM, rt/2 h, 80-90%, b) K$_2$CO$_3$, Propargyl bromide, DMF, rt/3 h, 85-90%, c) Li(OH):H$_2$O, THF, rt/overnight, 85-95%

General Procedure for Protection of Hydroxyls in Phenyl Quinazolin-4(3H)-One Core Structure (4a-4d): To a solution of phenyl quinazolin-4(3H)-one in dry DCM was added pyridine (2.0 equiv per hydroxyl group) and acetic anhydride (1.0 equiv per hydroxyl group). After stirring for 2 h, the reaction mixture was diluted with EtOAC (25 mL) and water (25 mL). The organic layer was separated and the aqueous phase was extracted with EtOAc (2×25 mL). The organic extracts were combined, washed with saturated 3N HCl (25 mL) solution to remove excess pyridine and dried over anhydrous Na$_2$SO$_4$. Removal of the solvent under reduced pressure afforded crude product and purified using flash chromatography on silica gel (10-50% ethyl acetate in hexanes) to give 4a-4d. Spectral (e.g. $^1$H NMR) characteristics of the following protected compounds were consistent with their predicted formulas:
3-(4-oxo-3, 4-dihydroquinazolin-2-yl)phenyl acetate (4a);
4-(4-oxo-3, 4-dihydroquinazolin-2-yl)phenyl acetate (4b);
5-(4-oxo-3,4-dihydroquinazolin-2-yl)-1,3-phenylene diacetate (4c);
and 2-methoxy-4-(4-oxo-3, 4-dihydroquinazolin-2-yl)phenyl acetate (4d).

General Procedure for Synthesis of the Propargylated Quinazolinone Monomer (5a-5d): To a solution of 4a-4d in N, N'-dimethylformamide was added K$_2$CO$_3$ (1.5 equiv) and allowed this reaction mixture to stir for 2 minutes fallowed by the addition of propargybromide (1.5 equiv). After stirring for 3 h, the reaction mixture was diluted with EtOAC (25 mL) and water (25 mL). The organic layer was separated and the aqueous phase was extracted with EtOAc (2×25 mL). The organic extracts were combined, washed with saturated NaCl solution (25 mL), and dried over anhydrous Na$_2$SO$_4$. Removal of the solvent under reduced pressure afforded the desired propargylated compounds in quantitative yield and sufficient purity (as indicated by TLC) to be directly used in the next reaction without any further purification. The crude recation mixture was then subjected to deacetylation by solubilizing in THF followed by addition of lithium hydroxide monohydrate Li(OH).H$_2$O (2 equvi). After stirring for overnight, the reaction mixture was diluted with EtOAC (25 mL) and water (25 mL) The organic layer was separated and the aqueous phase was extracted with EtOAc (2×25 mL) and removal of the solvent under reduced pressure afforded crude deacetylated compounds 5a-5d which were further purified using flash chromatography on silica gel (20-35% ethyl acetate in hexanes). Spectral ($^1$H NMR) characteristics of the following propargylated compounds 5a-5d were consistent with their predicted formulas:
2-(3-hydroxyphenyl)-3-(prop-2-yn-1-yl)quinazolin-4(3H)-one(5a);
2-(4-hydroxyphenyl)-3-(prop-2-yn-1-yl)quinazolin-4(3H)-one (5b);
2-(3, 5-dihydroxyphenyl)-3-(prop-2-yn-1-yl)quinazolin-4 (3H)-one (5c); and
2-(4-hydroxy-3-methoxyphenyl)-3-(prop-2-yn-1-yl)quinazolin-4(3H)-one (5d).

Synthesis of N$^3$-azide alkyl quinazolinon-4(3H)-one.

Scheme 4 of Example 2.

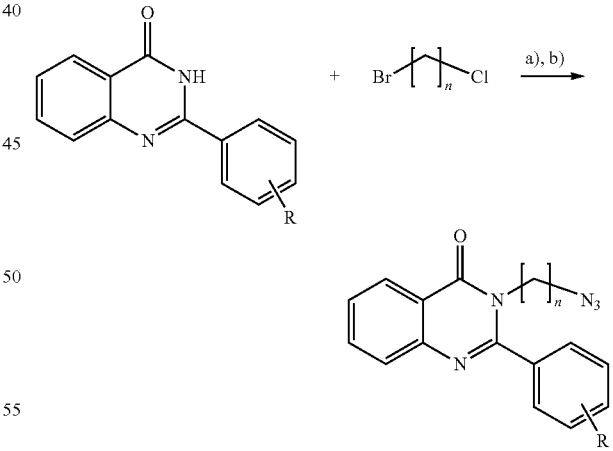

4a: R = 3-OAc
4b: R = 4-OAc
4c: R = 3, 5-OAc
4d: R = 3-OMe, 4-OAc

6a: R = 3-OH, n = 4
6b: R = 4-OH, n = 4
6c: R = 3, 5-OH, n = 4
6d: R = 3-OMe, 4-OH, n = 4
6e: R = 4-OH, n = 3
6f: R = 4-OH, n = 5
6g: R = 4-OH, n = 6
6h: R = 3-OAc, 5-OH, n = 4 a) K$_2$CO$_3$, DMF, rt/12 h, 85-90%, b) NaN$_3$, DMF, 60° C./overnight, 90-95%

General Procedure for Two Steps Synthesis of $N^3$-Azide Alkyl Quinazolinon-4(3H)-One 6a-6h: To a solution of 4a-4d (1.0 equiv) in N, N-dimethylformamide was added $K_2CO_3$ (1.5 equiv) and stirred for two minutes. This was followed by addition of 1-bromo-n-chloroalkane (1.0 equiv) and stirred vigorously for 12 hours. After the reaction completed as indicated from TLC the reaction mixture was diluted with EtOAC (25 mL) and water (25 mL). The organic layer was separated and the aqueous phase was extracted with EtOAc (2×25 mL) and removal of the solvent under reduced pressure afforded crude chloro compounds which were directly used for next step without further purification. The chloro compound was then solubilized in IV, N-dimethylformamide in a flask attached to a reflux condenser and sodium azide (1.5 equiv) was added to it. After stirring for overnight at 60° C., the reaction mixture was diluted with EtOAC (25 mL) and water. The organic layer was separated and the aqueous phase was extracted with EtOAc (2×25 mL). The organic extracts were combined, washed with saturated NaCl solution (25 mL), and dried over anhydrous $Na_2SO_4$. Removal of the solvent under reduced pressure afforded the desired crude azides 6a-6h which was further purified using flash chromatography on silica gel (20-35% ethyl acetate in hexanes). The formation of 6a-6h was confirmed using IR as azides show characteristic IR peak at 2100 $cm^{-1}$ In case of 4c two products were obtained, one with completely deprotected 6c and partially deprotected 6h. Spectral (e.g. $^1$H NMR) characteristics of the following azide compounds were consistent with their predicted formulas:

3-(4-azidobutyl)-2-(3-hydroxyphenyl)quinazolin-4(3H)-one (6a);

3-(4-azidobutyl)-2-(4-hydroxyphenyl)quinazolin-4(3H)-one (6b);

3-(4-azidobutyl)-2-(3,5-dihydroxyphenyl)quinazolin-4 (3H)-one(6c);

3-(4-azidobutyl)-2-(4-hydroxy-3-methoxyphenyl)quinazolin-4(3H)-one (6d);

3-(3-azidopropyl)-2-(4-hydroxyphenyl)quinazolin-4(3H)-one (6e);

3-(5-azidopentyl)-2-(4-hydroxyphenyl)quinazolin-4(3H)-one (6f);

3-(6-azidohexyl)-2-(4-hydroxyphenyl)quinazolin-4(3H)-one (6g); and 3-(3-(4-azidobutyl)-4-oxo-3, 4-dihydroquinazolin-2-yl)-5-hydroxyphenyl acetate (6h).

General Procedure for Copper-Catalyzed Azide Alkyne Cycloaddition 7-20: To a solution of terminal alkyne (1.0 equiv) and azide (1.0 equiv) were suspended in 1:1 mixture of $H_2O$ and N, N-dimethylformamide. Freshly prepared sodium ascorbate solution in water (5 mole %) was added fallowed by $CuSO_4.5H_2O$ solution in water (1 mole %) was added. The heterogeneous reaction mixture was stirred vigorously for 12 h, at which point it cleared and TLC analysis indicated complete consumption of the reactants. To this reaction mixture, 2 mL of 3% ammonia solution was added for quenching of excess $CuSO_4.5H_2O$ and stirred for further 10 min. The reaction mixture was diluted with EtOAC (25 mL), stirred for another 10-15 min and then filtered through a Celite bed. The combined reaction mixture was extracted with EtOAc (2×25 mL) and removal of the solvent under reduced pressure afforded crude compound which was further purified using flash chromatography. Spectral (e.g. $^1$H NMR characteristics of the following homodimer compounds 7-20 were consistent with their predicted formulas:

3-(3-(4-4-((2-(3-hydroxyphenyl)-4-oxoquinazolin-3(4H)-yl) methyl)-1H-1, 2, 3-triazol-1-yl) butyl)-4-oxo-3, 4-dihydroquinazolin-2-yl) phenyl acetate (7);

2-(3-hydroxyphenyl)-3-((1-(4-(2-(3-hydroxyphenyl)-4-oxoquinazolin-3(4H)-yl)butyl)-1H-1, 2, 3-triazol-4-yl) methyl) quinazolin-4(3H)-one (8);

3-hydroxy-5-(3-(4-(4-((2-(3-hydroxyphenyl)-4-oxoquinazolin-3(4H)-yl)methyl)-1H-1,2,3-triazol-1-yl)butyl)-4-oxo-3, 4-dihydroquinazolin-2-yl)phenyl acetate (9);

2-(4-hydroxy-3-methoxyphenyl)-3-((1-(4-(2-(4-hydroxy-3-methoxyphenyl)-4-O-quinazolin-3(4H)-yl)butyl)-1H-1,2, 3-triazol-4-yl)methyl)quinazolin-4(3H)-one (10);

2-(3-hydroxyphenyl)-3-(3-(4-((2-(3-hydroxyphenyl)-4-oxoquinazolin-3(4H)-yl)methyl)-1H-1,2, 3-triazol-1-yl)propyl)quinazolin-4(3H)-one (11);

2-(4-hydroxyphenyl)-3-((1-(4-(2-(3-hydroxyphenyl)-4-oxoquinazolin-3(4H)-yl)butyl)-1H-1,2,3-triazol-4-yl)methyl) quinazolin-4(3H)-one (12);

2-(4-hydroxyphenyl)-3-((4-(4-(2-(4-hydroxyphenyl)-4-oxoquinazolin-3(4H)-yl)butyl)-1H-1,2,3-triazol-4-yl)methyl) quinazolin-4(3H)-one (13);

2-(3-hydroxyphenyl)-3-((1-(4-(2-(4-hydroxyphenyl)-4-oxoquinazolin-3(4H)-yl)butyl)-1H-1,2,3-triazol-4-yl)methyl) quinazolin-4(3H)-one (14);

2-(4-hydroxyphenyl)-3-(5-(4-((2-(4-hydroxyphenyl)-4-oxoquinazolin-3(4H)-yl) methyl)-1H-1,2,3-triazol-1-yl)pentyl)quinazolin-4(3H)-one (15);

2-(4-hydroxyphenyl)-3-((1-(6-(2-(4-hydroxyphenyl)-4-oxoquinazolin-3(4H)-yl)hexyl)-1H-1,2,3-triazol-4-yl) methyl)quinazolin-4(3H)-one (16);

2-(4-hydroxy-3-methoxyphenyl)-3-((1-(4-(2-(3-hydroxyphenyl)-4-oxoquinazolin-3(4H)-yl)butyl)-1H-1,2,3-triazol-4-yl)methyl)quinazolin-4(3H)-one (17);

2-(3,5-dihydroxyphenyl)-3-(4-(4-((2-(3-hydroxyphenyl)-4-oxoquinazolin-3(4H)-yl) methyl)-1H-1, 2, 3-triazol-1-yl) butyl)quinazolin-4(3H)-one (18);

3-(3-(4-4-((2-(3,5-dihydroxyphenyl)-4-oxoquinazolin-3 (4H)-yl)methyl)-1H-1,2,3-triazol-1-yl)butyl)-4-oxo-3,4-dihydroquinazolin-2-yl)-5-hydroxyphenyl acetate (19); and 2-(3,5-dihydroxyphenyl)-3-((1-(4-(2-(3,5-dihydroxyphenyl)-4-oxoquinazolin-3(4H)yl)butyl)-1H-1,2,3-triazol-4-yl)methyl)quinazolin-4(3H)-one (20).

Quercetin Protection. Synthesis of Compounds 21a and 21b:

Scheme 5 of Example 2.

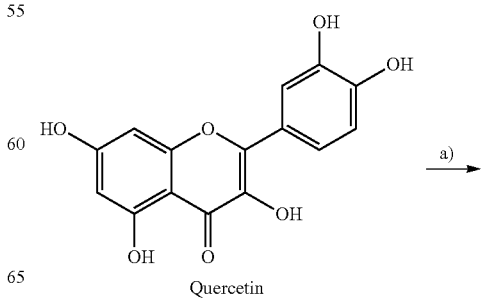

Quercetin

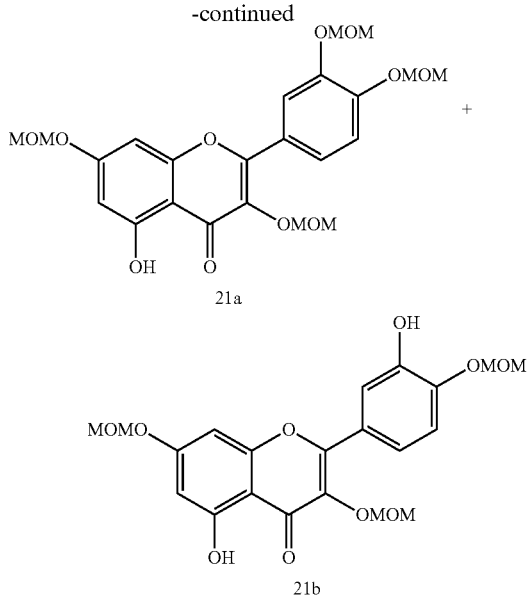

a) MOMCl, DCM, N, N'-diisopropylethylamine, rt/overnight, 65-70% overall yield

To a solution of quercetin (1.0 equiv) in DCM, N, N-diisopropylethylamine (8.0 equiv) and MOM chloride (3.5 equiv) was added under nitrogen. After vigorous stirring at 0° C. for 1 h, the reaction mixture was allowed to warm to room temperature over 2 h and the stirring was maintained for 12 h. The resulting mixture was diluted with water (100 ml), extracted with EtOAC (200 ml), and then the organic layer was washed with water (100 ml) and dried over $NaSO_4$. The residue obtained after removal of the solvent was purified by flash column chromatography to afford two products: the tri protected ether 21a (50% yield) and tetra protected ether 21b (50% yield). Spectral (e.g. $^1H$ NMR) characteristics of the following compounds were consistent with their predicted formulas: 2-(3,4-bis(methoxymethoxy)phenyl)-5-hydroxy-3,7-bis(methoxymethoxy)-4H-chromen-4-one (21a); and 5-hydroxy-2-(3-hydroxy-4-(methoxymethoxy)phenyl)-3,7-bis(methoxymethoxy)-4H-chromen-4-one(21b).

Synthesis of Intermediate 22: To a solution of 21b in N, N'-dimethylformamide was added $K_2CO_3$ (1.5 equiv) and allowed this reaction mixture to stir for 2 minutes fallowed by the addition of propargybromide (1.0 equiv). After stirring for 12 h at room temperature, the reaction mixture was diluted with EtOAC (25 mL) and water (25 mL). The organic layer was separated and the aqueous phase was extracted with EtOAc (2×25 mL). The organic extracts were combined, washed with saturated NaCl solution (25 mL), and dried over anhydrous $Na_2SO_4$. Removal of the solvent under reduced pressure fallowed by purification using flash column chromatography afforded the desired propargylated compound 24 in quantitative yield. Spectral (e.g. $^1H$ NMR) characteristics of the compound 5-hydroxy-3, 7-bis(methoxymethoxy)-2-(4-(methoxymethoxy)-3-(prop-2-yn-1-yloxy)phenyl)-4H-chromen-4-one (22) were consistent with its predicted formula.

Synthesis of Intermediate 23: To a solution of 22 in N, N'-dimethylformamide was added $K_2CO_3$ (1.5 equiv) and allowed this reaction mixture to stir for 2 minutes fallowed by the addition of methyliodode (1.0 equiv). After stirring for 6 h, the reaction mixture was diluted with EtOAC (25 mL) and water. The organic layer was separated and the aqueous phase was extracted with EtOAc (2×25 mL). The organic extracts were combined, washed with saturated NaCl solution (25 mL), and dried over anhydrous $Na_2SO_4$. Removal of the solvent under reduced pressure fallowed by purification using flash column chromatography afforded 23 in quantitative yield. Spectral (e.g. $^1H$ NMR) characteristics of the compound 5-methoxy-3,7-bis(methoxymethoxy)-2-(4-(methoxymethoxy)-3-(prop-2-yn-1-yloxy)phenyl)-4H-chromen-4-one(23) were consistent with its predicted formula.

Synthesis of Intermediate 24: The compound 23 was solubilized in acetone in a flask attached to a reflux condenser and 3N HCl was added to it. After stirring for 12 h at reflux temperature, the reaction mixture was neutralized with $NaHCO_3$ solution and diluted with EtOAC (25 mL). The organic layer was separated and the aqueous phase was extracted with EtOAc (2×25 mL). The organic extracts were combined, washed with saturated NaCl solution (25 mL), and dried over anhydrous $Na_2SO_4$. Removal of the solvent under reduced pressure afforded the desired crude 26 which was further purified using flash chromatography. Spectral (e.g. $^1H$ NMR) characteristics of the compound 3,7-dihydroxy-2-(4-hydroxy-3-(prop-2-yn-1-yloxy)phenyl)-5-methoxy-4H-chromen-4-one(24) were consistent with its predicted formula.

General Procedure for Copper-Catalyzed Azide Alkyne Cycloaddition 25-27: Synthesis of polyphenolic heterodimers was achieved as described above for the polyphenolic homodimers and is depicted in Scheme 6 of this Example (below). Spectral characteristics of heterodimers 25-27 were consistent with their predicted formulas.

Synthesis of Intermediate 28: To a solution of alkyne 5b (2.0 equiv) and bis-azide (1.0 equiv) were suspended in 1:1 mixture of $H_2O$ and N, N-dimethylformamide. Freshly prepared sodium ascorbate solution in water (10 mole %) was added fallowed by $CuSO_4.5H_2O$ solution in water (2 mole %) was added. The heterogeneous reaction mixture was stirred vigorously for 12 h, at which point it cleared and TLC analysis indicated complete consumption of the reactants. To this reaction mixture, 2 mL of 3% ammonia solution was added for quenching of excess $CuSO_4.5H_2O$ and stirred for further 10 min. The reaction mixture was diluted with EtOAC (25 mL), stirred for another 10-15 min and then filtered through a Celite bed. The combined reaction mixture was extracted with EtOAc (2×25 mL) and removal of the solvent under reduced pressure afforded crude compound which was further purified using flash chromatography. Spectral characteristics of the bis-triazole compound 28 were consistent with its predicted formula.

Synthesis of Polyphenolic Homodimer 29: A solution of azide 6b (100 mg, 0.3619 mmol) and alkyne 5b (121 mg, 0.3619 mmol) in 0.5 mL of dioxane was added to Cp*RuCl$(PPh_3)_2$ (5.76 mg, 2 mole %) dissolved in 2.5 mL of dioxane. The vial was purged with nitrogen, sealed, and heated in an oil bath at 60° C. for 12 h, at which point TLC indicated complete consumption of the alkyne and the azide starting materials. The mixture was adsorbed on to silica and chromatographed with hexanes/ethyl acetate to elute the product 29 in 80% yield (177 mg). Spectral characteristics of polyphenolic homodimer 29 were consistent with its predicted formula.

Varying the linker length (n=3-6) in the azide 6 scaffold afforded an opportunity of expanding the diversity of the library. CuAAC in the presence of aqueous $CuSO_4$ (1 mole %) and sodium ascorbate (5 mole %) gave 1,2,3-triazoles 7-20 (Scheme 2, presented in FIG. 10). The high reaction yields (80-95%) observed for the QAO series coupled with an essentially single product suggested 1,4-substitution of the triazole, as established in the literature.[10] Intermediates 7-20 were sulfated using the microwave conditions developed for monomers to obtain sulfated QAOs 7S-20S (Scheme 2 of Example 2, presented in FIG. 10). The reaction resulted in sulfation of each available —OH group to give a single per-sulfated product, which simplified purification resulting in 80-90% yields.

Compounds 7S-20S contain an identical QAO unit at either end and will be referred to herein as homo 'click' dimers, although these are not truly symmetric. To explore further structural dependence, inhibitors 25S-27S were synthesized (Scheme 6 of Example 2). These contain a flavonoid core on one end and a QAO core on the other (hetero 'click' dimers). The major structural difference between the two types of click dimers is the higher sulfation level of the flavonoid scaffold. Utilizing an intramolecular H-bond dependent protection-deprotection strategy, flavonoid 21b was transformed into propargyl derivative 24, which gave 25-27 upon CuAAC with azide 6a, 6d, and 6h (Scheme 6 of Example 2). Sulfation of these molecules resulted in flavonoid-QAO hetero 'click' dimers 25S-27S.

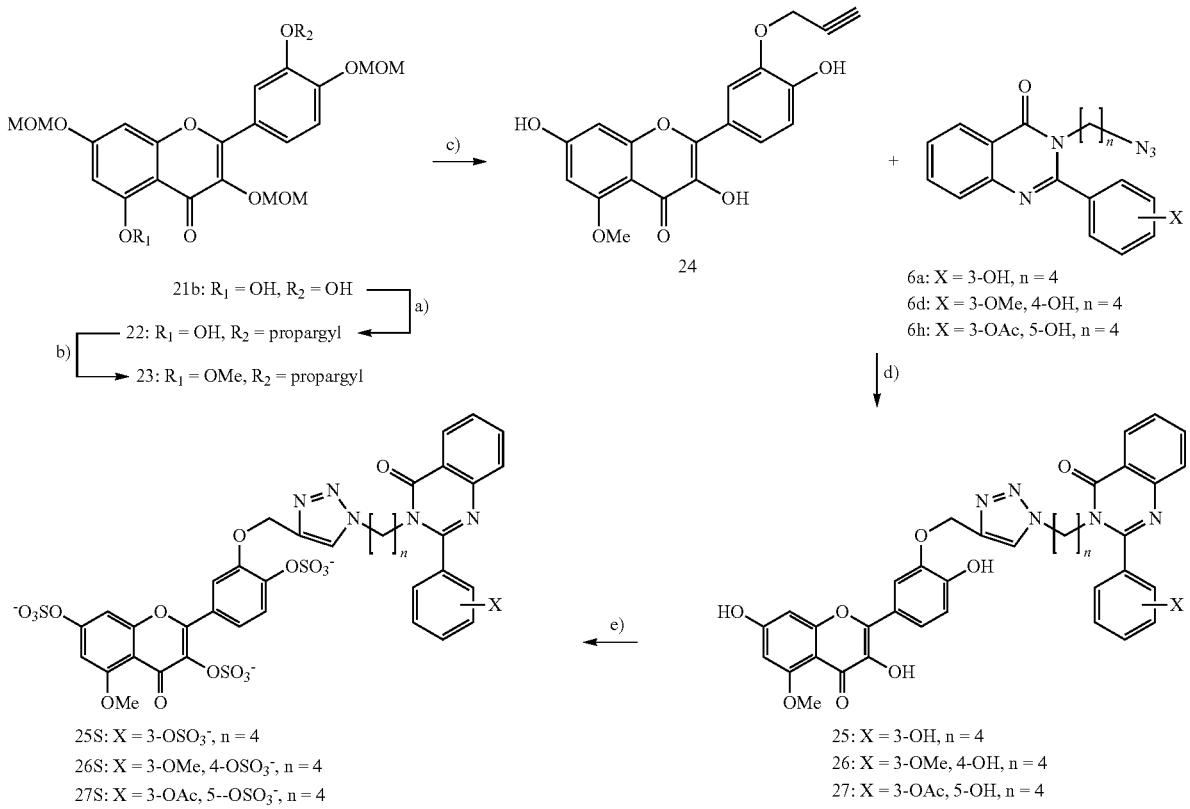

Scheme 6 of Example 2. Synthesis of sulfated QAOs 25S-27S.

a) K$_2$CO$_3$, propargyl bromide, DMF, rt/2 h, 85-90%, b) K$_2$CO$_3$, MeI, DMF, rt/4 h, 85-90%, c) 3N HCl, acetone, reflux/overnight, 55-60%, d) CuSO$_4$·5H$_2$O (1 mol %), sodium ascorbate (5 mol %), DMF/H$_2$O (1:1), rt/overnight, 80-95%, e) SO$_3$:Me$_3$N, Et$_3$N, CH$_3$CN, microwave/30 min, 85-90%.

To study the dependence of inhibition on the geometry of the linker, a double click sulfated QAO dimer 28S was synthesized using a slight modification of the strategy developed for homo click dimers (Scheme 7 of Example 2). Inhibitor 28S contains two 1,4-triazole units, instead of one 1,4-triazole moiety in 7S-21S and 25S-27S. Finally, geometric isomerism in the linker was also studied. Whereas all click dimers contained a 1,4-substituted triazole moiety, 29S contained a 1,5-substituted triazole moiety. Inhibitor 29S was synthesized from phenolic precursor 29, which was synthesized in high yields using a ruthenium-catalyzed cycloaddition[11] of azide 6f and alkyne 5B (Scheme 8 of Example 2). Comparison of $^1$H NMR spectra of regioisomers 15 and 29 shows that the methylenic protons attached to the triazole moiety in each case was significantly different. Whereas 1,4-substituted triazole 15 showed the CH$_2$ at 5.81 δ, 29 displays the corresponding signal at 5.96 δ confirming the difference in geometries.

Scheme 7 of Example 2. Synthesis of sulfated QAO 28S.

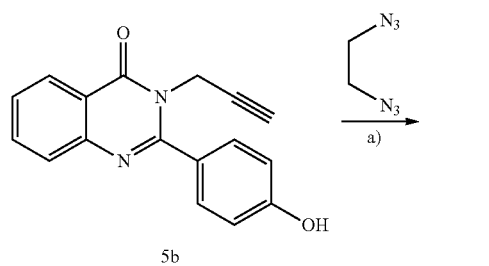

5b

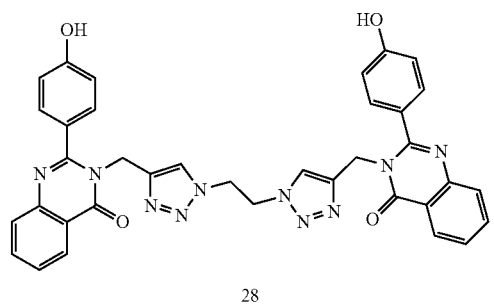

28

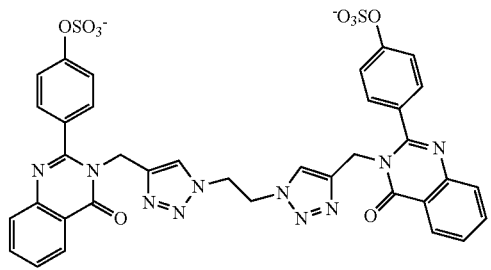

28S a) CuSO₄·5H₂O (2 mol%), sodium ascorbate (10 mol%), DMF/H₂O (1:1), rt/overnight, 80%, b) SO₃:Me₃N, Et₃N, CH₃CN, microwave/30 min, 90%

Scheme 8 of Example 2. Synthesis of sulfated QAO 29S.

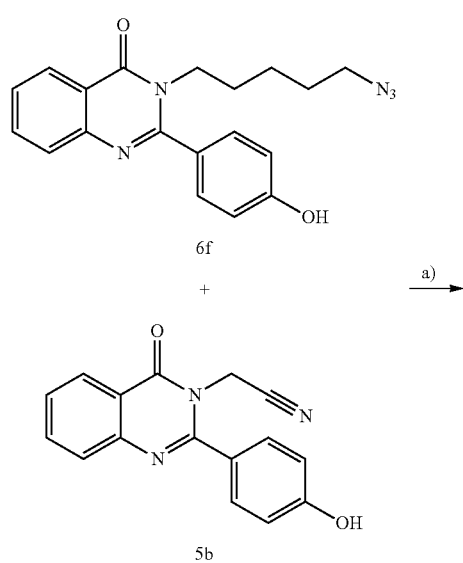

6f

+

5b

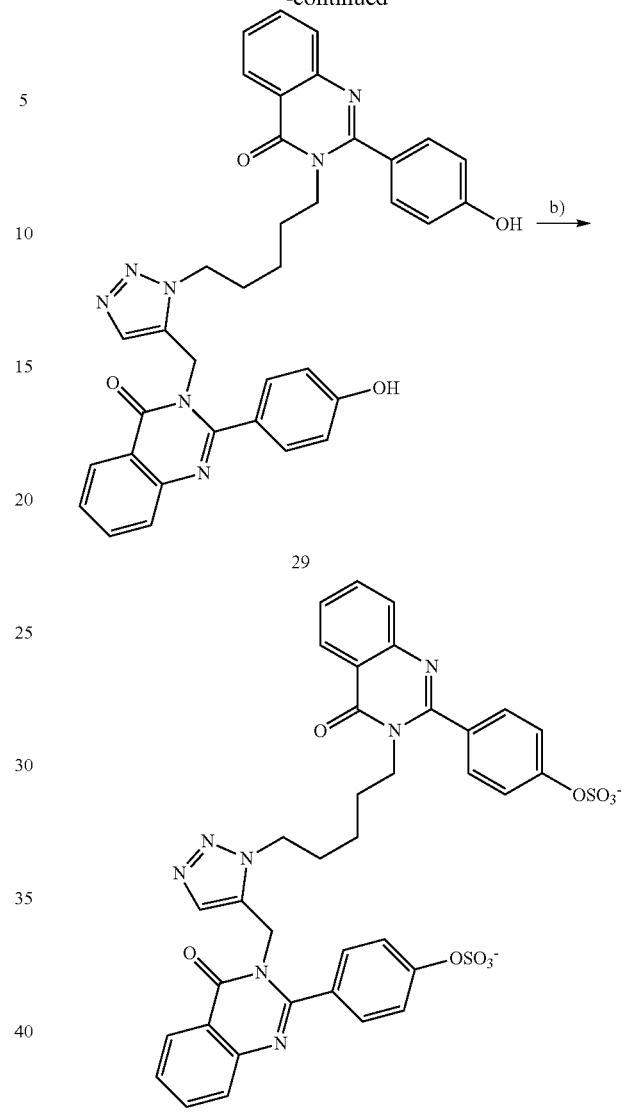

29

29S a) CpRuCl(PPh₃)₂, dioxane, 60° C./overnight, 80%, b) SO₃:Me₃N, Et₃N, CH₃CN, microwave/30 min, 90%

In combination, the library of 26 sulfated QAOs was synthesized through the use of simple synthetic tools in generally high yields. Structural diversity in this family of sulfated hydrophobic small molecules arises from the number of sulfate groups on the core scaffold (1 to 4), the position of sulfate groups (either 2, 3, 4 or 5 on aromatic ring), the type of core scaffolds (QAO or flavonoid), the type of linker (one or two triazoles), the length of linker (8-11 intervening atoms), and the geometry of the linker (1,4- or 1,5-triazole). This is a first small library of potential GAG mimetics that is based on a fully synthetic, heterocyclic scaffold. The success of this synthetic venture indicates the feasibility of the development of other novel GAG mimetics based on a sulfated hydrophobic scaffold.

Inhibition of Human Factor XIa by Sulfated QAOs. The library of sulfated QAOs was screened for inhibition of human FXIa and other coagulation enzymes using chromogenic substrate hydrolysis assay, as described earlier.[1,3,6] The sigmoidal decrease in the initial rate of protease activity (on a semi-log plot) as a function of ligand concentration was fitted using the logistic dose-response equation to calculate the $IC_{50}$. Of the 26 sulfated QAOs studied, 16 exhibited inhibition of factor XIa at pH 7.4 and 37° C. (FIG. 12A) suggesting a good 'hit' ratio arising from the novel SAM discovery strategy. Most importantly, the un-sulfated precursors of the 26 sulfated molecules did not inhibit factor XIa at all highlighting the importance of the anionic group ($—OSO^{3-}$) as a recognition element.

The range of inhibitory potency was found to be reasonable (50 to >1000 μM), while the efficacy for nearly all inhibitors was very high (>85%). Inhibitor 26S displayed an efficacy of approximately 50%, which supports the possibility of structure-dependent 'allosteric modulation'. Molecules with only one sulfate group, i.e., all monomeric sulfated QAOs and dimeric 7S, were found to be inactive. Molecules containing two sulfate groups (8S-17S, 28S and 29S) were most active (52-320 μM), while those with three or more sulfate groups (18S-20S and 25S-27S) were progressively less potent (Tables 5 and 6). Among the inhibitors that contain two sulfate groups, those with $—OSO_3—$ at meta position on both rings are less potent than those with meta/para sulfate substitution, which in turn are less potent than para/para sulfate substitution. Comparative examples of the three categories include 9S, 14S and 13S, respectively, with affinities of 153, 91 and 82 μM (Table 5). That a sulfate group at the para position is favored is also borne out by comparison of 25S, 26S and 27S (Table 6). The observation that para substitution is more favored than either meta or ortho substitution is not unusual considering steric influence.

TABLE 5

Inhibition of human factor XIa by sulfated QAOs 7S-20S.[a]

| Inhibitor | $R_1$ | $R_2$ | $R_3$ | $R_1'$ | $R_2'$ | $R_3'$ | n | $IC_{50}$ (μM) | ΔY % |
|---|---|---|---|---|---|---|---|---|---|
| 7S | —OAc | —H | —H | —$OSO_3^-$ | —H | —H | 4 | >1000 | NA[b] |
| 8S | —$OSO_3^-$ | —H | —H | —$OSO_3^-$ | —H | —H | 4 | 102 ± 2[c] | 100 ± 6 |
| 9S | —OAc | —H | —$OSO_3^-$ | —$OSO_3^-$ | —H | —H | 4 | 153 ± 1 | 96 ± 1 |
| 10S | —$OCH_3$ | —$OSO_3^-$ | —H | —$OCH_3$ | —$OSO_3^-$ | —H | 4 | 139 ± 1 | 95 ± 1 |
| 11S | —$OSO_3^-$ | —H | —H | —$OSO_3^-$ | —H | —H | 3 | 320 ± 2 | 91 ± 4 |
| 12S | —$OSO_3^-$ | —H | —H | —H | —$OSO_3^-$ | —H | 4 | 159 ± 2 | 88 ± 3 |
| 13S | —H | —$OSO_3^-$ | —H | —H | —$OSO_3^-$ | —H | 4 | 82 ± 1 | 91 ± 2 |
| 14S | —H | —$OSO_3^-$ | —H | —$OSO_3^-$ | —H | —H | 4 | 91 ± 2 | 103 ± 5 |
| 15S | —H | —$OSO_3^-$ | —H | —H | —$OSO_3^-$ | —H | 5 | 59 ± 1 | 89 ± 2 |
| 16S | —H | —$OSO_3^-$ | —H | —H | —$OSO_3^-$ | —H | 6 | 52 ± 1 | 97 ± 1 |
| 17S | —$OSO_3^-$ | —H | —H | —$OCH_3$ | —$OSO_3^-$ | —H | 4 | 182 ± 1 | 88 ± 5 |
| 18S | —$OSO_3^-$ | —H | —$OSO_3^-$ | —$OSO_3^-$ | —H | —H | 4 | 213 ± 2 | 93 ± 2 |
| 19S | —$OSO_3^-$ | —H | —$OSO_3^-$ | —OAc | —H | —$OSO_3^-$ | 4 | 273 ± 3 | 91 ± 2 |
| 20S | —$OSO_3^-$ | —H | —$OSO_3^-$ | —$OSO_3^-$ | —H | —$OSO_3^-$ | 4 | >1000 | NA |

[a]The $IC_{50}$, HS, and ΔY values were obtained following non-linear regression analysis of direct inhibition of factor Xa. Inhibition was monitored by spectrophotometric measurement of residual proteases activity (see Experimental Procedures).

[b]Not applicable.

[c]Errors represent ± 1 S.E.

TABLE 6

Inhibition of human factor XIa by sulfated QAOs 25S-29S.[a]

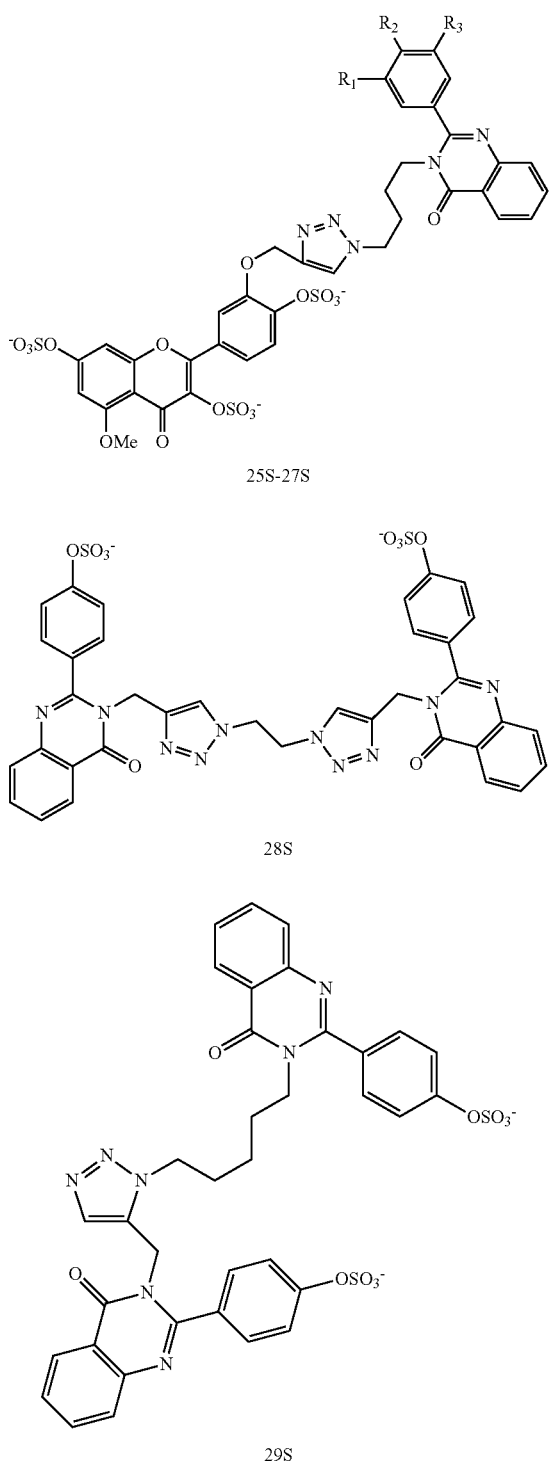

| Inhibitor | $R_1$ | $R_2$ | $R_3$ | $IC_{50}$ (μM) | ΔY % |
|---|---|---|---|---|---|
| 25S | —$OSO_3^-$ | —H | —H | >1000 | NA[b] |
| 26S | —$OCH_3$ | —$OSO_3^-$ | —H | 216 ± 27[c] | 50 ± 13 |
| 27S | —OAc | —H | —$OSO_3^-$ | 407 ± 10 | 90 ± 6 |
| 28S | — | — | — | 305 ± 3 | 98 ± 3 |
| 29S | — | — | — | 90 ± 0.2 | 94 ± 1 |

[a]The $IC_{50}$, HS, and ΔY values were obtained following non-linear regression analysis of direct inhibition of factor Xa. Inhibition was monitored by spectrophotometric measurement of residual proteases activity (see Experimental Procedures).
[b]Not applicable.
[c]Errors represent ± 1 S.E.

Within the para/para disubstituted series, increasing the length of the linker from four (13S) to five (15S) to six methylenes (16S) increases the potency gradually (~80→~50 μM). The trend is also shown by the meta/meta disubstituted inhibitors 11S (3 atom linker) and 8S (4 atoms), which display $IC_{50}$s of 102 and 320 μM, respectively. This is an unusual observation. Typically conformational flexibility reduces the potency of inhibition. The result suggests that an extended linker probably serves to place the two QAO scaffolds better in two hydrophobic regions of FXIa. Comparision of 28S and 16S also supports this conclusion. Whereas 28S contains two triazole rings, 15S contains only one triazole moiety on an otherwise identical base scaffold. Both inhibitors contain a minimum of 10 linker atoms, yet the additional triazole of 28S is likely to impart significant rigidity to the linker in comparison to that for 15S. Inhibitor 28S is approximately 6-fold less potent than 15S (Tables 5 and 6).

Another factor that appears to play a role is the geometry of the triazole ring. Whereas 1,4-triazole containing 15S displayed a potency of 59 μM, the potency dropped to 94 μM with 29S, which contained a 1,5-triazole moiety. Likewise, non-sulfate substitutions, such as acetyl (e.g., 9S and 19S) or methoxy (e.g., 17S and 26S), also introduce variations in inhibitor potency suggesting a small, but significant, contribution of these positions in binding.

To assess whether the sulfated QAOs inhibited serine proteases related to human FXIa, we screened the inhibitors against thrombin, factor Xa, trypsin and chymotrypsin. Screening was performed using appropriate chromogenic substrates, as described earlier.[3,6] Essentially no inhibition was observed at concentrations as high as 500 μM (FIG. 12B). This suggested high selectivity of sulfated QAOs for targeting human FXIa. This is not completely unexpected as the design strategy (FIG. 10) should inherently engineer selectivity. Both the HBS and hP domain(s) are expected to be structurally different even on related enzymes, thus engineering enhanced selectivity. In comparison, enzymes that possess only on one type of binding site (either HBS or hP) should not be targeted by sulfated QAOs.

Overall, the work led to identification of six inhibitors (8S, 13S, 14S, 15S, 16S and 28S) that displayed $IC_{50}$ less than 100 μM (Tables 5 and 6). All six molecules bear one sulfate group at either end of the molecule in a rather symmetric location. Molecules that are either more or less sulfated than these six are much less potent. The inhibition potency was significantly dependent on the substitution pattern of the sulfated QAO scaffold.

Comparison of Inhibition Potency of Sulfated QAOs with GAGs and GAG Mimetics. The best SAM discovered in this study, 16S, displayed an $IC_{50}$ of 52 μM (Table 5). This potency compares favorably to several sulfated molecules described in the literature or available naturally.

Inhibition Potency of Sulfated QAOs in Human Plasma. To assess whether the chromogenic substrate-based inhibition of human factor XIa by sulfated QAOs translates into activity against macromolecular substrates, we studied anticoagulant activity in human plasma. Two assays, the prothrombin and activated partial thromboplastin time assay (PT and APTT, respectively), are typically utilized to identify an inhibitor's ability to retard the extrinsic and intrinsic coagulation signal. A dose-dependent prolongation of APTT is observed in the presence of sulfated QAOs 13S, 15S and 16S (FIG. 13). A 2-fold increase in APTT was observed in the range of 0.95-1.06 mM for the three molecules (Table 7), which is about 12-18-fold less active in comparison to the potency in buffer. This is typical of many anticoagulants and arises primarily from binding to human serum albumin. In the PT assay, 13S appears to exhibit reasonable dose-dependent prolongation of clotting time with a 2-fold increase calculated to occur at about 1.12 mM. The results observed for 15S and 16S support the selective inhibition of FXIa, while 13S affects both the APTT and PT.

TABLE 7

Effect of sulfated QAOs on human plasma clotting times.[a]

| Inhibitor | 2 × APTT (µM) | 2 × PT (µM) |
| --- | --- | --- |
| 13S | 979 | 1119 |
| 15S | 1062 | 1684 |
| 16S | 950 | >2000 |

[a]Prolongation of clotting time as a function of concentration of sulfated quinazolinones in either activated partial thromboplastin time assay (APTT) or prothrombin time assay (PT). Clotting assays were performed in duplicate (SE ≤ 10%) as described in Experimental Methods.

Mechanism of Inhibition of Sulfated QAOs. Inherent in the design strategy is the expectation that SAMs should function as allosteric modifiers of proteolytic activity. To assess this, the kinetics of chromogenic substrate S2366 hydrolysis by factor XIa in the presence of 14S was studied. The plot of initial rate as a function of Spectrozyme FXIa concentration displayed a characteristic hyperbolic profile (FIG. 14), which was fitted using the standard Michaelis-Menten equation to derive the $K_M$ and $V_{MAX}$ of factor XIa activity. The $K_M$ for Spectrozyme FXIa was found to be 0.31±0.03 mM, which did not change much as the concentration of 14S increased to 135 µM (0.30±0.07 mM). In constrast, the $V_{MAX}$ decreased from 43.3±1.5 mAU/min to 5.1±0.5 mAU/min as the concentration of 14S increased from 0 to 135 µM. Thus, while the affinity of small chromogenic substrate remains unaffected by 14S binding, the proteolytic activity decreases. This is characteristic of a non-competitive mechanism of factor XIa inhibition and most H/HS mimetics reported in the literature to date, such as sulfated low molecular weight lignins and sulfated benzofurans, have exhibited such a mechanism.

Sulfated QAOs Engage Residues of the HBS Present on the Catalytic Domain of Factor XIa.

Figure 15:
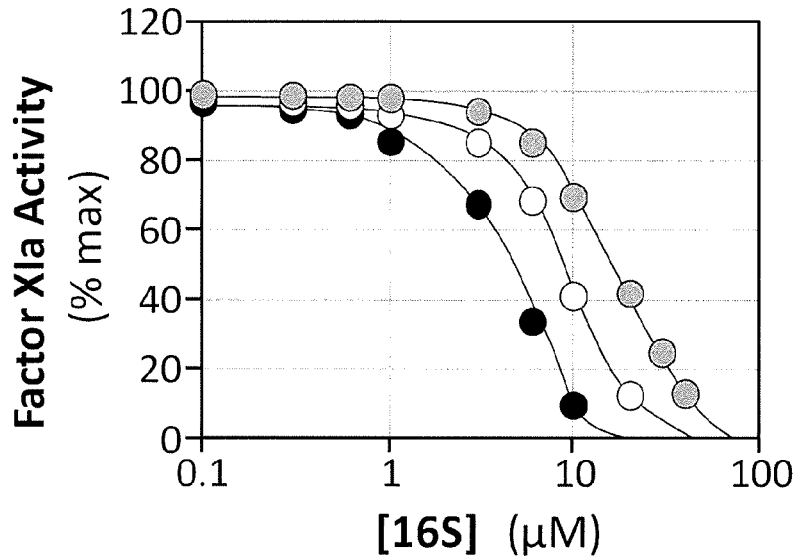
FIG. 15. Dose-response profiles for 16S inhibition of recombinant wild type FXIa catalytic domain (FXIa-CD, solid circles), Arg530Ala FXIa-CD single mutant (open circles) and Lys529Ala,Arg530Ala,Arg532Ala FXIa-CD triple mutant (shaded circles) in 50 mM TrisHCl buffer pH 7.4 containing 150 mM NaCl, 0.1% PEG8000, and 0.02% Tween80 at 37° C. Solid lines represent sigmoidal dose-response fits.

Heparin binds to FXIa in two sites—in the A3 domain (Lys252, Lys253, and Lys255) and in the catalytic domain (Lys529, Arg530, Arg532, Lys535, and Lys539). To identify whether sulfated QAOs engage the A3 domain or the catalytic domain, we studied inhibition of human FXIa containing only the catalytic domain. This domain and all site-directed mutants were expressed and purified, as described earlier.[32,33] The catalytic domain alone (FXIa-CD) was inhibited by a sulfated QAO, 16S, as potently as the wild-type enzyme indicating that the A3 domain is not necessary for activity (not shown). Replacement of Arg530 alone by Ala in FXIa-CD resulted in an increase of 2-fold in the $IC_{50}$ (FIG. 15). Further replacement of Lys529, Arg530 and Arg532 to Ala each reduced the potency by approximately 5-fold (FIG. 15). At the same time, Lys535Ala and Lys539Ala exhibited no change in $IC_{50}$ of 16S from that of the wild-type FXIa-CD (not shown). This implies that one or more residues of the HBS present on the catalytic domain of FXIa is(are) involved in binding to 16S. The loss of affinity for 16S with the triple mutation is moderate. In comparison, replacement of a single arginine on thrombin (Arg173) introduced a defect of approximately 22-fold for a sulfated benzofuran, while for sulfated low molecular weight lignins the loss in potency was in the range of 2-8-fold. This implies that the loss in potency for sulfated QAOs is more similar to that of sulfated low molecular weight lignins than that for sulfated benzofurans. Sulfated lignins contain several sulfate groups, which bind to more than one arginine/lysine residues on thrombin. In a similar manner, the two sulfate groups of QAOs likely bind to two arginine/lysine loci on factor XIa. The site-directed mutagenesis data shows that one of these electropositive loci is the HBS. The other locus remains to be identified. In combination with the non-competitive mechanism of inhibition, the results suggest that sulfated QAOs recognize an exosite on FXIa away from the active site or allosterically inhibit the enzyme.

Figure 16:
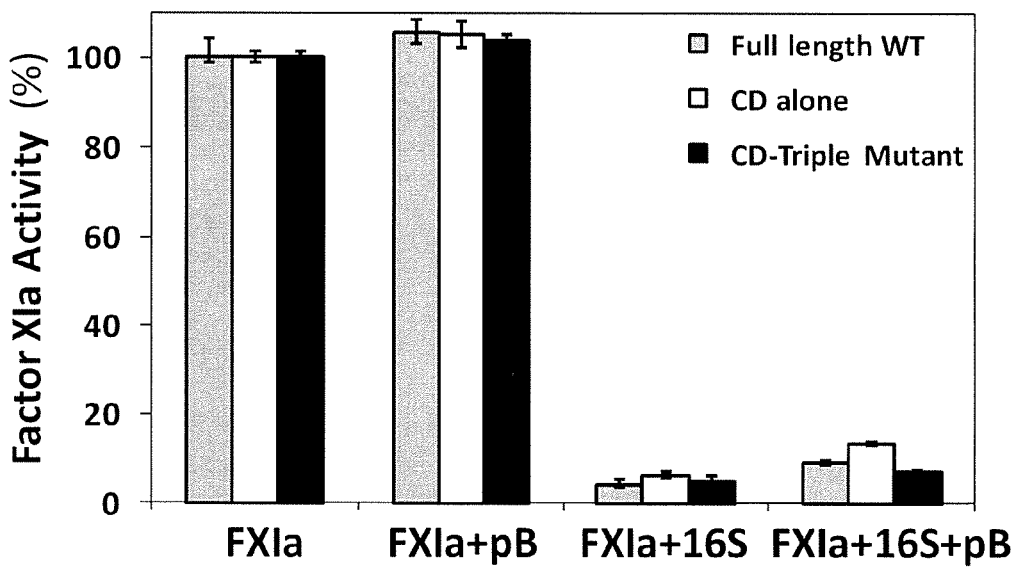
FIG. 16. The effect of polybrene on the proteolytic activity of full-length wild type factor XIa (shaded bars), FXIa-CD (open bars), and FXIa-CD containing Lys529Ala, Arg530Ala,Arg532Ala triple mutations (solid bars). The proteolytic activity of each enzyme in the presence of 30 µM polybrene and 3 M 16S was measured using S2366 hydrolysis.
Figure 18:
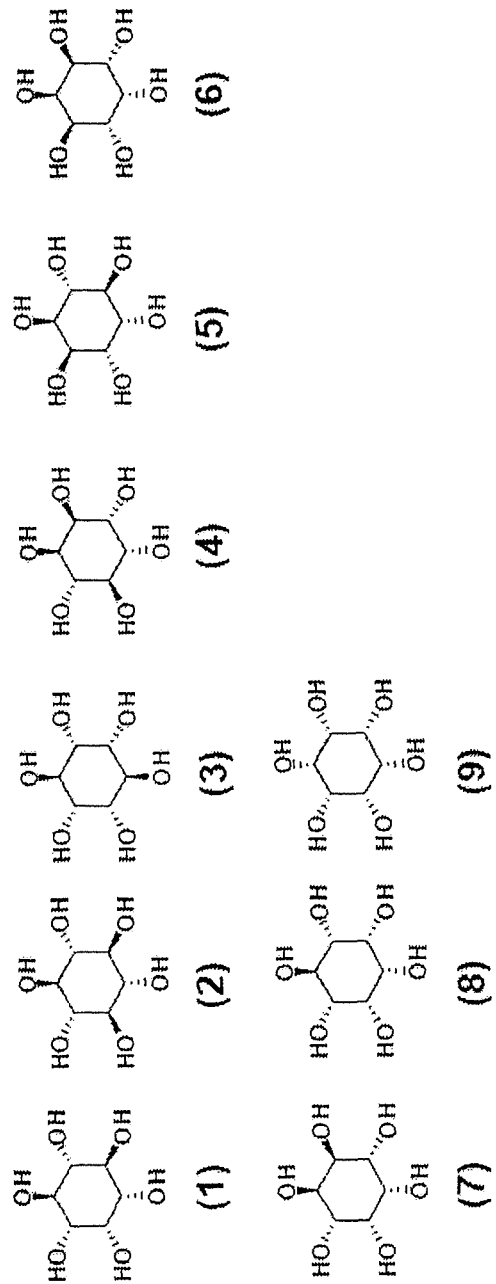
FIG. 18. Exemplary steroisomeric inositol core structures of inositol-based Factor XIa inhibitors.

Factor XIa Inhibition by Sulfated QAOs is not Neutralized by a Competing Electropositive Polymer. A critical element of the proposed design principle is that hP domain (s) on the target enzyme are involved in selective inhibition. To assess this aspect, we studied the effect of polybrene on the proteolytic activity of factor XIa. Polybrene has been regularly used to neutralize heparin since the early 1990s. Basically, the multiple positive charges of polybrene neutralize the numerous sulfate and carboxylate groups of heparin resulting in an antidote effect. If sulfated QAOs bind to factor XIa only through electrostatic sulfate-arginine/ lysine forces, and not through significant hydrophobic forces, then polybrene should neutralize their inhibitory effects. FIG. 16 shows the 16S inhibition of the catalytic activity of wild-type FXIa, FXIa-CD, and FXIa-CD containing triple mutation (Lys529Ala, Arg530Ala, Arg532Ala) in the presence of polybrene. The proteolytic activity of both the full length wild-type FXIa, FXIa-CD, and FXIa-CD containing triple mutations is reduced to approximately 4, 6 and 5%, respectively, in the presence of 16S. This is as expected due to saturation of FXIa by 16S. Addition of 30 µM polybrene, which rapidly neutralizes heparin's anticoagulant effect, changes the inhibition level to 9.2±1.0% (FXIa-WT), 13.1±0.7% (FXIa-CD), and 7.1±1.2% (FXIa-CD with triple mutations). The reduction in inhibition shows that the antidote does affect FXIa-16S interaction, but the influence is mostly marginal. A primarily electrostatic interaction between FXIa and 16S should have been essentially reversed by the high concentration of polybrene. Thus, 16S appears to utilize primarily hydrophobic forces in binding to FXIa. This is a key element invoked in the design principle and is likely to contribute to the selectivity of targeting only FXIa observed above. Yet, these results should be tempered with the recognition that polybrene is not selective for sulfated QAO. Unfortunately, no agent is currently available that can selectively compete with such sulfated and, yet, hydrophobic molecules. The best avenue for establishing the proposed dual-element design strategy is likely to be X-ray structure determination of a FXIa-SAM co-complex.

Sulfated QAOs Bind to Factor XIa in a Classic, Direct Allosteric Manner. The studies performed so far indicate that sulfated QAO inhibit human FXIa by utilizing an allosteric site. However, the HBS on the catalytic domain of FXIa, although allosteric, is within 22 Å of the active site. The molecular size of sulfated QAOs is also fairly large raising a minor concern whether the inhibition is truly through an allosteric, cooperative process. To test this possibility, we studied the interaction of sulfated QAOs with FXIa irreversibly blocked at the active site using a dansylated EGR peptide, i.e., FXIa-DEGR. FIG. 17A shows the fluorescence emission spectra of FXIa alone and in complex with a SAM (13S-16S). The fluorescence of the active site dansyl group increases in the presence of each sulfated QAO. The maximal increase in fluorescence is dependent on the type of sulfated QAO. In addition, the emission maximum of FXIa-DEGR shifts from approximately 550 nm in the absence of sulfated QAOs to ~505 nm in their presence suggesting a major blue shift. Both the increase in fluorescence intensity and blue shift in $\lambda_{EM}$ suggest strong perturbation of the electrostatic environment around FXIa's active site following interaction with sulfated QAOs.

To further investigate the interaction, FXIa-DEGR's fluorescence at ~550 nm was monitored as a function of sulfated QAO concentration. FIG. 17B shows the profiles of the titrations for the most potent sulated QAOs 13S-16S. The profiles reveal a characteristic sigmoidal dependence on the concentration of sulfated QAO. This is a striking observation and strongly suggestive of a cooperative binding process. The profile can be fitted well by the standard, three-parameter Hill equation, which gives the maximal fluorescence change ($\Delta F_{MAX}$), the Hill coefficient (n) and the apparent dissociation constant ($K_D$) of binding (Table 4). Using this equation, the four sulfated QAOs were found to bind with an affinity of 37-91 which compare favorably with the $IC_{50}$ measured above. The Hill coefficients were calculated to be in the range of 6.4-9.0, which support a strongly cooperative, allosteric interaction. Overall, the thermodynamic fluorescence study demonstrates that sulfated QAOs bind to FXIa through a classic, allosteric interaction process.

In summary, the sulfated QAOs discovered in this work are potent inhibitors of FXIa, an enzyme thought to be safe to target for inducing anticoagulation. As discussed above, inhibitor 26S displays 50% efficacy, while 13S-16S display efficacy greater than 85%, demonstrating that it is possible to design sulfated QAOs with variable levels of efficacies, and that offer fine control over the anticoagulation state of plasma.

Abbreviations for Example 2
APTT, activated partial thromboplastin time; CuAAC, Copper-catalyzed azide-alkyne cycloaddition reaction; DS, dermatan sulfate; FXI, factor XI; FXIa, factor XIa; FXIa-CD, catalytic domain of FXIa; FXIIIa, factor XIIIa; GAG, Glycosaminoglycan; GBP, GAG-binding protein; HBS, Heparin-binding site; hP, Hydrophobic; HS, Heparan sulfate; QAO, Quinazolin-4(3H)-ones; PEG, Polyethylene glycol; PT, prothrombin time; SAM, Sulfated allosteric modulator

REFERENCES FOR EXAMPLE 2

1. Gunnarsson, G. T.; Riaz, M.; Adams, J.; Desai, U. R. Synthesis of per-sulfated flavonoids using 2,2,2-trichloro ethyl protecting group and their factor Xa inhibition potential. *Bioorg. Med. Chem.* 2005, 13, 1783-1789.
2. Sidhu, P. S.; Liang, A.; Mehta, A. Y.; Abdel Aziz, M. H.; Zhou, Q.; Desai, U. R. Rational design of potent, small, synthetic allosteric inhibitors of thrombin. *J. Med. Chem.* 2011, 54, 5522-5531.
3. Abdel Aziz, M. H.; Mosier, P. D.; Desai, U. R. Identification of the site of binding of sulfated, low molecular weight lignins on thrombin. *Biochem. Biophys. Res. Commun.* 2011, 413, 348-352.
4. Al-Horani, R. A.; Desai, U. R. Chemical sulfation of small molecules-advances and challenges. *Tetrahedron* 2010, 66, 2907-2918.
5. Raghuraman, A.; Riaz, M.; Hindle, M.; Desai, U. R. Rapid and efficient microwave-assisted synthesis of highly sulfated organic scaffolds. *Tetrahedron Lett.* 2007, 48, 6754-6758.
6. Henry, B. L.; Thakkar, J. N.; Liang, A.; Desai, U. R. Sulfated, low molecular weight lignins inhibit a select group of heparin-binding serine proteases. *Biochem. Biophys. Res. Commun.* 2012, 417, 382-386.
7. Smith, S. B.; Gailani, D. Update on the physiology and pathology of factor IX activation by factor XIa. *Expert Rev Hematol.* 2008, 1, 87-98.
8. Emsley, J.; McEwan, P. A.; Gailani, D. Structure and function of factor XI. *Blood* 2010, 115 2569-2577.
9. Xia, Y; Yang, Z. Y.; Hour, M. J.; Kuo, S. C.; Xia, P.; Bastow, K. F.; Nakanishi, Y; Nampoothiri, P.; Hackl, T.; Hamel, E.; Lee, K. H. Antitumor agents. Part 204: Synthesis and biological evaluation of 2-aryl quinazolinones. *Bioorg. Med. Chem. Lett.* 2001, 11, 1193-1196.
10. Rostovtsev, V. V.; Green, L. G; Fokin, V. V.; Sharpless, K. B. A stepwise Huisgen cycloaddition process: Copper (II)-catalyzed regioselective "Ligation" of azides and terminal alkynes. *Angew. Chem., Int. Ed.* 2002, 41, 2596-2599.
11. Zhang, Li.; Chen, X.; Xue, P.; Sun, H. H. Y; Williams, I. D.; Sharpless, K. B.; Fokin, V. V.; Jia, G Ruthenium-catalyzed cycloaddition of alkynes and organic Azides. *J. Am. Chem. Soc.* 2005, 127, 15998-15999.

Example 3

Chemical Synthesis and Purification of the Inositol-Based FXIa Inhibitors

The invention also provides inositol-based inhibitors that can be quantitatively synthesized in three chemical steps of esterification, debenzylation, followed by microwave-assisted sulfonation[1] as illustrated in Scheme 1 of this Example, see below) and described below:

Chemical Synthesis and Purification of the Inositol-Based FXIa Inhibitor

Inositol-based inhibitors can be quantitatively synthesized in three chemical steps of esterification, debenzylation, followed by microwave-assisted sulfonation as follows (Scheme 1 of this Example):

Scheme 1. Synthesis of myo-inositol based FXIa inhibitors.

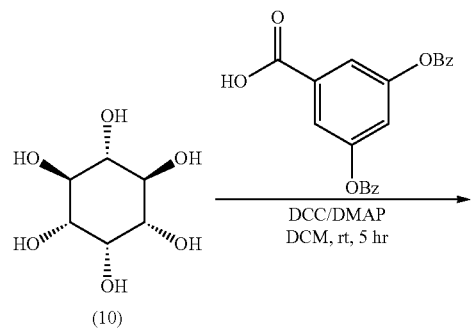

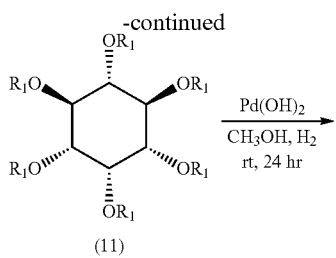

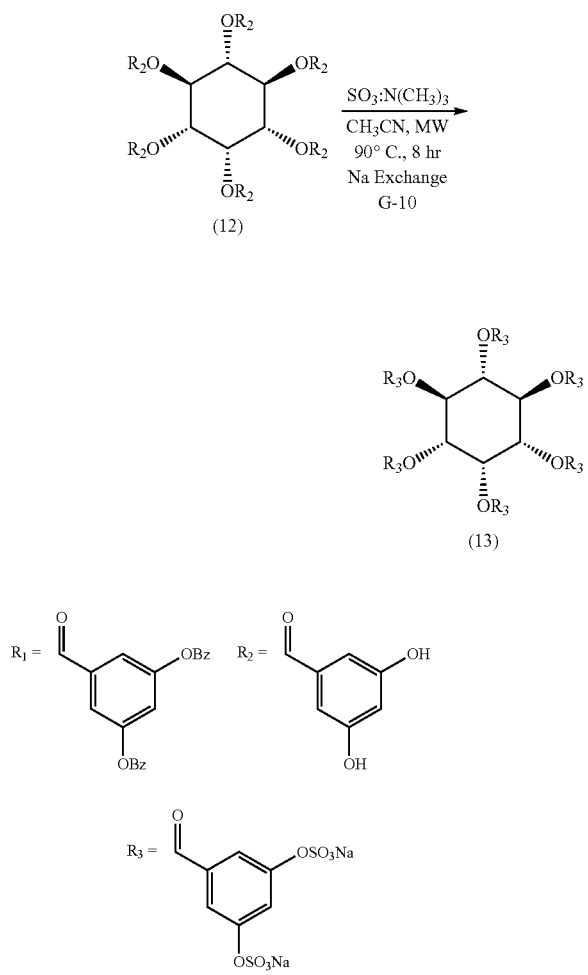

A) Esterification of Myo-Inositol:

Myo-inositol (1) (1.0 mmol) was added to a homogenous solution of 3,5-dibenzyloxy benzoic acid (6.0 mmol), 4-dimethylaminopyridine (DMAP) (6.0 mmol), and dicyclohexylcarbodiimide (DCC) (6.0 mmol) in dry $CH_2Cl_2$ (30 ml). The resulting solution was then refluxed overnight under nitrogen. After completion of reaction (as indicated by TLC), the reaction mixture was cooled and concentrated under vacuum to about 15 ml. The resulting organic phase was washed with 3 N HCl (10 ml), brine solution (2×10 mL), and dried over anhydrous $Na_2SO_4$. After filtration, the per-esterified myo-inositol containing solution was again concentrated and purified by flash chromatography. The flash chromatography was performed using Teledyne ISCO (Lincoln, Nebr.) Combiflash RF system and disposable normal silica cartridges of 30-50μ particle size, 230-400 mesh size and 60 Å pore size. The flow rate of the mobile phase was in the range of 18 to 35 ml/min and mobile phase gradient of EtOAc/hexanes was used to elute the desired product as white solid (11 in Scheme 1 of this Example). A mixture of 20% EtOAc/hexanes was particularly used for the TLC purposes. Analytical TLC was performed using UNIPLATE™ silica gel GHLF 250 um pre-coated plates (ANALTECH, Newark, Del.). The white solid product was confirmed by detailed $^1H$ and $^{13}C$ NMR as well as ESI-MS. The yield of DCC-mediated per-esterification of myo-inositol was about 85%.[2]

B) Debenzylation of Intermediate (11):

Deprotection of benzyl groups was promoted by mixing intermediate (11) and 10% $Pd(OH)_2$ on activated charcoal in $CH_3OH$ (10 ml). Hydrogen gas was then pumped into the mixture at RT. After stirring the solution overnight, the catalyst was filtered on Celite and the organic filtrate was concentrated in vacuuo to afford the corresponding polyphenol (12) in quantitative yields and sufficient purity (as indicated by TLC). The polyphenol structure (12) was confirmed by detailed $^1H$ and $^{13}C$ NMR as well as ESI-MS. This polyphenol was directly used in the subsequent reaction without any further purification.

C) Microwave-Assisted Sulfonation of Polyphenol (12):

Sulfated hexa-substituted myo-inositol (SMI, 13) was synthesized by a modified conditions of the microwave-assisted protocol developed earlier in our lab.[1] Briefly, the corresponding polyphenol precursor (12) (1.0 mmol) and $SO_3$—$N(CH_3)_3$ (60.0 mmol) were mixed in anhydrous $CH_3CN$ (2 ml) in microwave tube. The reaction tube was sealed and microwaved (CEM-discover microwave synthesizer) for 8 h at 90° C. The per-sulfated product (SMI, 13) was obtained in yields of >60% as fluffy while powder after size exclusion purification, sodium exchange, and lyophilization.

Generally, all sulfated molecules were purified using Sephadex G10 size exclusion chromatography. The quaternary ammonium counter-ions of sulfate groups present in the molecules were exchanged for sodium ions using SP Sephadex-Na cation exchange chromatography. Sephadex G10 and SP Sephadex-Na chromatographies were performed using Flex columns (KIMBLE/KONTES, Vineland, N.J.) of dimensions 170×1.5 cm and 75×1.5 cm, respectively. For regeneration of the cation exchange column, 1 L of 2 M NaCl solution was used. Water was used as eluent in both chromatographies. Five mL fractions were collected and analyzed by capillary electrophoresis (CE). CE experiments were performed using a Beckman P/ACE MDQ system (Fullerton, Calif.). Electrophoresis was performed at 25° C. and a constant voltage of 8 kV or a constant current of 75 μA using an uncoated fused silica capillary (ID 75 μm) with the total and effective lengths of 31.2 cm and 21 cm, respectively. A sequential wash of 1M HCl (10 min), water (3 min), 1M NaOH (10 min), and water (3 min) at 20 psi was used to activate the capillary. Before each run, the capillary was rinsed with the run buffer; 50 mM sodium phosphate buffer of pH=3, for 3 min at 20 psi. Sulfated compounds injected at the cathode (0.5 psi for 4 s) and detected at the anode (214 nm). The purity of each sulfated compound, as determined by CE, was greater than 95%. All sulfated structures were characterized by NMR as well as MS-ESI.

For synthesis of the carboxylate and phosphate congeners of sulfates-containing compounds the benzoic acid derivatives were prepared as follows (Scheme 2 of this Example, below):

Scheme 2. Synthesis of protected carboxylate and phosphate-containing starting materials.

A)

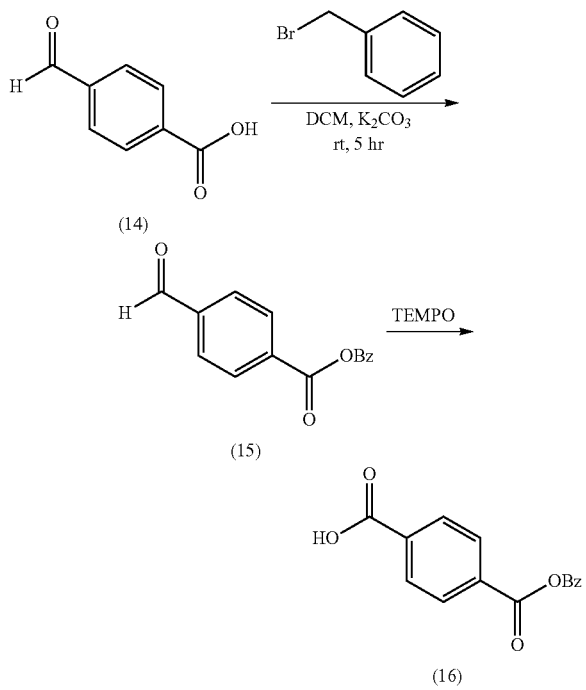

B)

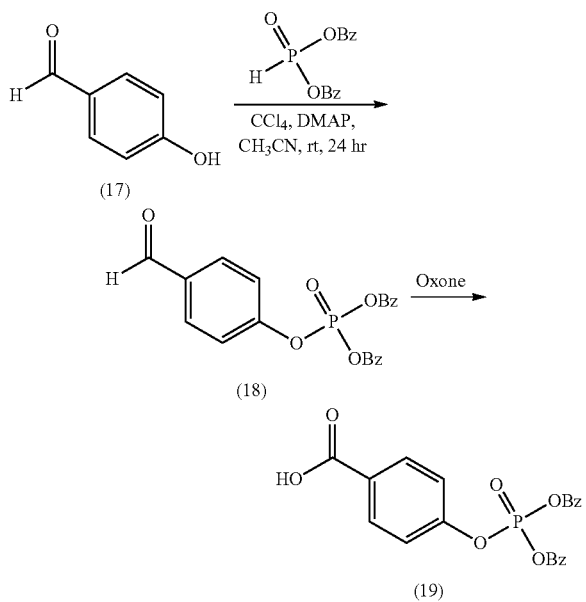

A) Preparation of Molecule (16), the Carboxylate Congener of Sulfate:

Benzylation of 4-formyl benzoic acid followed by aldehyde oxidation: To a stirred solution of 4-formyl benzoic acid (14) (1.0 mmol) in dry $CH_2Cl_2$ (4 ml), anhydrous $K_2CO_3$ (1.5 mmol) was added, followed by addition of benzyl bromide (1.2 mmol). The reaction mixture was then kept stirring for 5 hrs at RT. After the reaction completion (as indicated by TLC), the reaction mixture was diluted with $CH_2Cl_2$ (16 ml), washed with $H_2O$ (10 ml), dried over anhydrous $Na_2SO_4$, filtered and concentrated in vacuuo. Flash chromatography was used as described above to afford about 90% yield of benzylated 4-formyl benzoic acid (15) as colorless liquid. To form the corresponding acid (16), bis-acetoxyiodo benzene (BAIB) (2.2 mmol), (2,2,6,6-Tetramethyl-piperidin-1-yl)oxyl (TEMPO) (0.2 mmol), and benzylated 4-formyl benzoic acid (15) (1.0 mmol) were combined in a reaction vessel, and to this mixture was added a (1:1) $CH_3CN$—$H_2O$ mixture solution (2 ml).[3] The reaction mixture was stirred for 3 hrs at RT before the respective product (16) was obtained and purified. 4-Benzyloxycarbonyl benzoic acid (16) was obtained as white solid in yield of 70%. Both compounds (15 and 16) were structurally confirmed by NMR and ESI-MS techniques.

B) Preparation of Molecule (19), the Phosphate Congener of Sulfate:

Phosphorylation of 4-hydroxy benzaldehyde followed by aldehydes oxidation: To a stirred solution of 4-hydroxy benzaldehyde (17) (1.0 mmol) in dry $CH_3CN$ (10 ml), dibenzylphosphite (1.1 mmol) was added at $-10°$ C., followed by the addition of DIPEA (2.0 mmol), DMAP (0.1 mmol) and $CCl_4$ (5.0 mmol). The reaction mixture was then kept stirring for 24 hrs at RT. After the reaction completion (as indicated by TLC), the reaction mixture was diluted with EtOAc (16 ml), washed with $H_2O$ (10 ml), dried over anhydrous $Na_2SO_4$, filtered and concentrated in vacuuo. Flash chromatography was used as described above to afford about 78% yield of molecule (18) as colorless liquid.[4] To form the corresponding acid (19), the aldehyde (18) (1.0 mmol) was dissolved in DMF (10 ml). Oxone (1.0 mmol) was added in one portion and stirred at RT for 3 hrs. The reaction was monitored by TLC. 1N HCl was used to dissolve the salts and EtOAc was added to extract the products. The organic extract was washed with 1N HCl (3×5 ml) and brine, dried over $Na_2SO_4$, and the solvent was removed under reduced pressure to obtain the crude product. Product was purified by flash chromatography as described above affording white solid in a yield of about 68%.[5] Both compounds (18 and 19) were structurally confirmed by NMR and ESI-MS techniques.

The ability of the sulfated inositol analogs to inhibit factor XIa was studied using the in vitro assay described in Example 1. In this assay, the factor XIa enzyme is anticipated to hydrolyze a particular peptide linkage in the corresponding peptide substrate releasing p-nitroaniline which absorbs at wavelength of 405 nm giving a line slope corresponds to the enzyme activity. The line slope of no inhibitor status is considered as a reference slope and it depends on the relative concentrations of factor XIa enzyme and its substrate. Factor XIa enzyme concentration was decided to get appropriate reference slope of approximately 25-35, whereas the substrate concentration was set to be larger than its affinity to factor XIa enzyme under equilibrium condition, $K_m$. In presence of potential factor XIa inhibitor, the enzyme capacity to hydrolyze the designated peptide linkage in the substrate gets diminished or completely abolished depending on the inhibitor concentration and efficacy. Thus, the amount of p-nitroaniline released is consequently reduced or neglected giving a relatively lower slope than the reference slope of the no inhibitor status. Such decreased slope reflects a drop in the catalytic enzyme activity of factor XIa. Measuring the inhibitor potential to inhibit factor XIa enzyme in vitro assay can be most likely translated into anticoagulant activity under the pathological conditions of thrombotic diseases.

In order to numerically describe the potency of the potential inhibitor, the ratio of the slope in presence of the potential inhibitor to the reference slope of no inhibitor status was calculated. This ratio gives the residual factor XIa enzymatic activity which was measured at different concentrations of inhibitor. A concentration-dependent inhibition of factor XIa was noted for the claimed structures, which was fitted using the standard dose-response equation to calculate the concentration of the inhibitor required to 50% inhibit XIa activity. For per-sulfated molecule (SMI, 13), $FXIa\text{-}IC_{50}$ was 90 nM.

REFERENCES FOR EXAMPLE 3

1. Al-Horani, R. A.; Desai, U. R. *Tetrahedron,* 2010, 66, 2907-2918.
2. Arapitsas, P.; Menichetti, S.; Vincieri, F. F.; Romani, A. *J. Agric. Food Chem.* 2007, 55, 48-55.
3. Epp, J. B.; Widlanski, T. S. *J. Org. Chem.* 1999, 64, 293-295.
4. Huo, C.; Dou, Q. P.; Chan, T. H. *Tetrahedron Lett.* 2011, 52, 5478-5483.
5. Travis, B. R.; Sivakumar, G. M.; Hollist, O.; Borhan, B. *Org. Lett.* 2003, 5, 1031-1034.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound of Formula XI

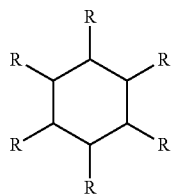

Formula XI wherein each R is independently selected from i)

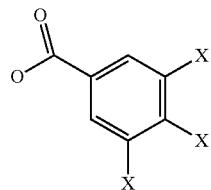

where each X is independently selected from —H, —OH, —OCH$_3$, —OSO$_3^-$, —OPO$_3^{-2}$, and —COO$^-$
and ii) Y, where each Y is independently selected from, —OH, —OSO$_3^-$, —OPO$_3^{-2}$ and —COO$^-$;

with the caveats that at least one R is

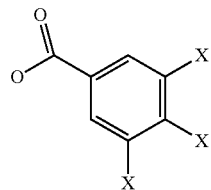

and at least one X or one Y is —OSO$_3^-$;

and stereoisomers and pharmaceutically acceptable salts thereof.

2. The compound of claim 1, wherein said pharmaceutically acceptable salts comprise monovalent salts, divalent salts and ammonium salts.

3. The compound of claim 2, wherein said monovalent salts include Na$^+$ and K$^+$ salts.

4. The compound of claim 2, wherein said divalent salts include Ca$^{2+}$ and Mg$^{2+}$ salts.

* * * * *